US009844456B2

(12) United States Patent
Ierulli

(10) Patent No.: US 9,844,456 B2
(45) Date of Patent: Dec. 19, 2017

(54) NASAL DILATOR AND METHODS OF FABRICATING MEDICAL DEVICES

(71) Applicant: Joseph Vincent Ierulli, Vancouver, WA (US)

(72) Inventor: Joseph Vincent Ierulli, Vancouver, WA (US)

(73) Assignee: CORBETT LAIR INC., Bradenton, FL (US)

( * ) Notice: Subject to any disclaimer, the term of this patent is extended or adjusted under 35 U.S.C. 154(b) by 593 days.

(21) Appl. No.: 14/139,619

(22) Filed: Dec. 23, 2013

(65) Prior Publication Data

US 2014/0194922 A1 Jul. 10, 2014

Related U.S. Application Data

(63) Continuation of application No. 12/964,746, filed on Dec. 10, 2010, now Pat. No. 8,641,852.

(51) Int. Cl.
*A61F 5/08* (2006.01)

(52) U.S. Cl.
CPC ....... *A61F 5/08* (2013.01); *A61M 2210/0618* (2013.01); *Y10T 156/1069* (2015.01); *Y10T 156/1074* (2015.01); *Y10T 156/1075* (2015.01); *Y10T 156/1085* (2015.01); *Y10T 156/1087* (2015.01)

(58) Field of Classification Search
CPC .............. A61F 5/08; A61M 2210/0618; Y10T 156/1074
USPC .................................................... 606/204.45
See application file for complete search history.

(56) References Cited

U.S. PATENT DOCUMENTS

| 3,072,123 | A | * | 1/1963 | Davis | A61F 13/496 604/366 |
| 4,862,574 | A | * | 9/1989 | Seidy | A61F 13/15723 156/252 |
| 5,476,091 | A | * | 12/1995 | Johnson | A61F 5/08 128/200.24 |
| 6,769,428 | B2 | * | 8/2004 | Cronk | A61F 5/08 128/200.24 |

* cited by examiner

*Primary Examiner* — Vy Bui
(74) *Attorney, Agent, or Firm* — Mersenne Law

(57) ABSTRACT

Methods are disclosed for converting on a mass scale elongated material webs into finished parts or devices. Slits form strands in a web, the strands comprising interconnected objects which correspond to parts of finished devices. Strands are combined with additional webs to form a material laminate from which finished devices are die cut. The methods are suitable for a range of converting applications including medical devices, particularly the external nasal dilator. Complex dilator devices produced from the methods are formed as a single body truss having horizontal regions adapted to engage outer wall tissues of first and second nasal passages of a nose. When in use the dilator stabilizes or expands nasal outer wall tissues and prevents the outer wall tissues from drawing inward during breathing. Methods of manufacture comprise separate steps for fabricating and assembling the elements and layers of finished dilator devices and for packaging finished devices individually or in groups. Waste material is incorporated into subsequent fabrication processes to produce the same or complementary devices.

18 Claims, 40 Drawing Sheets

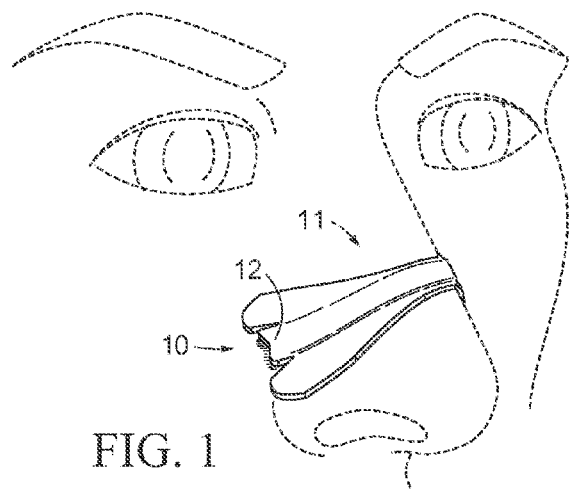
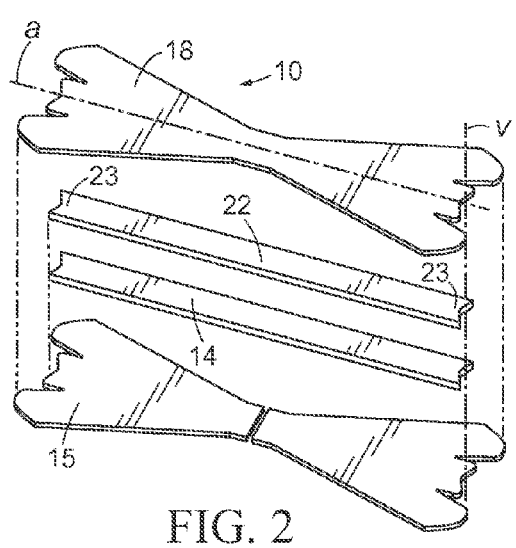
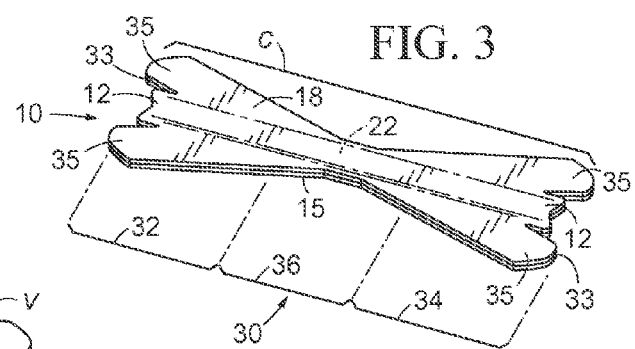
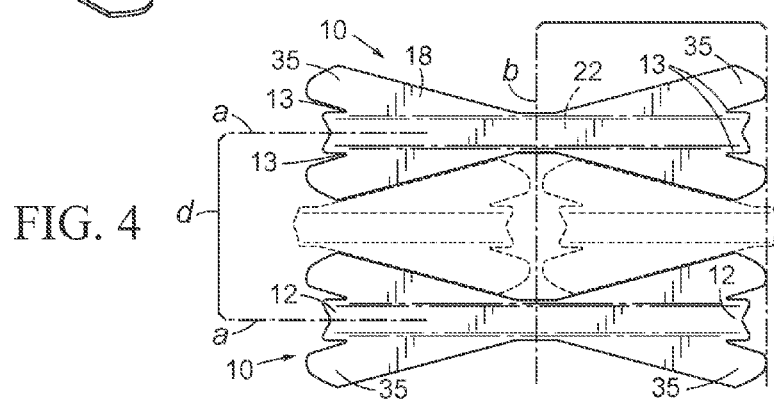

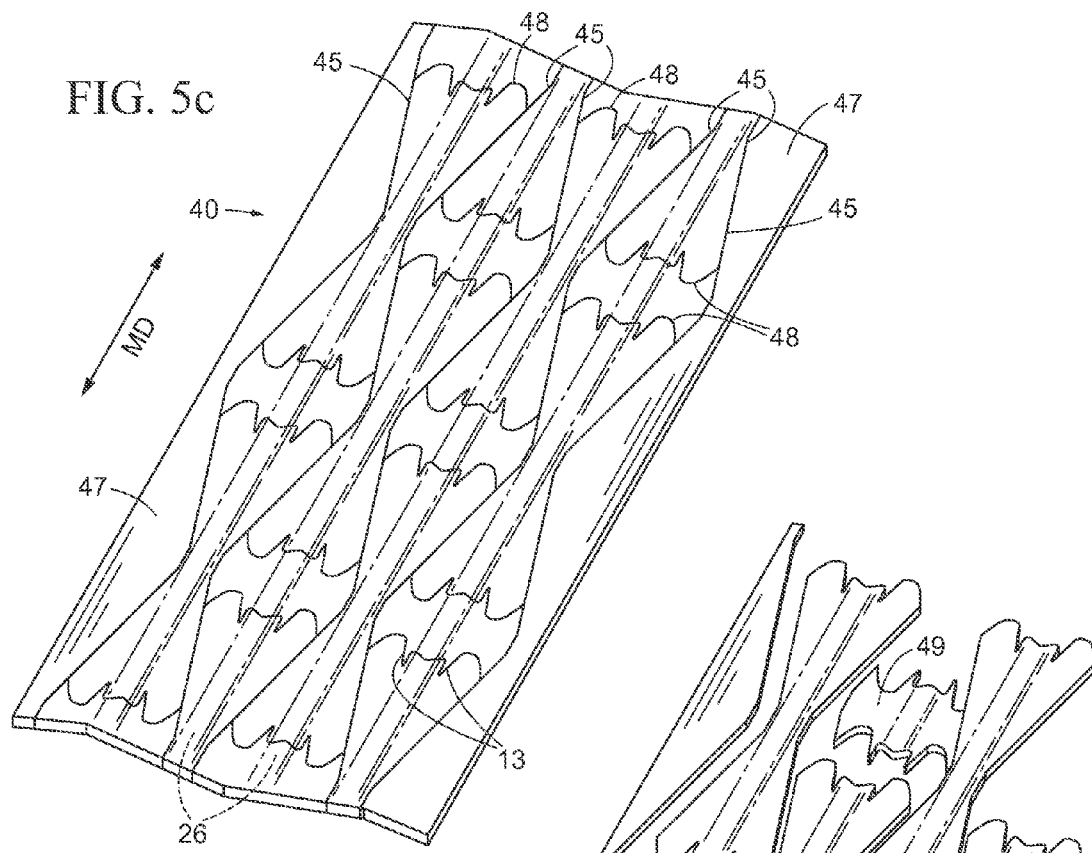
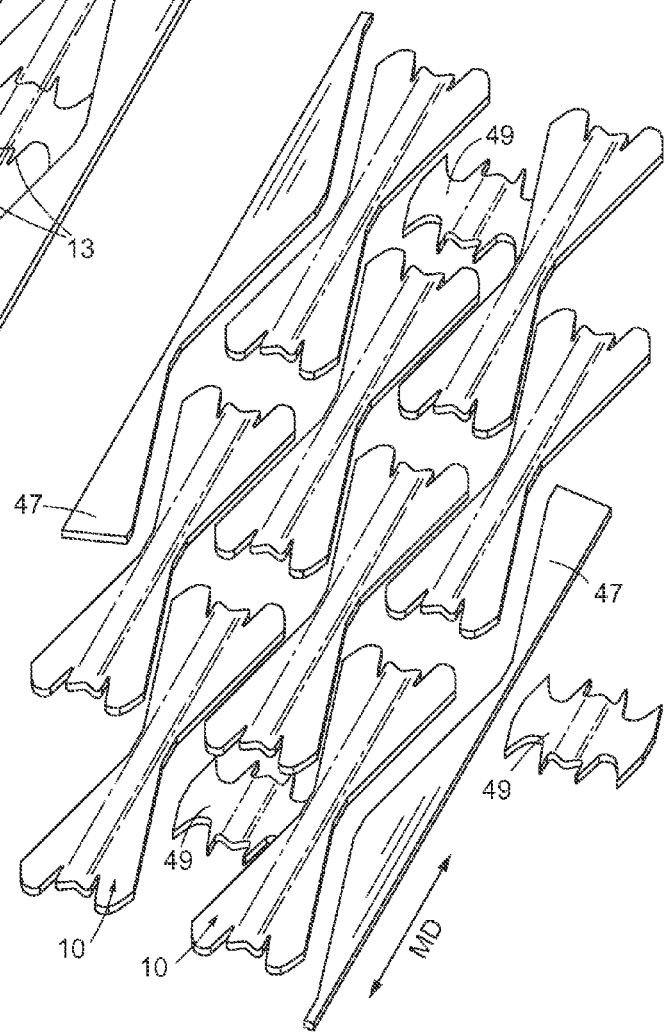

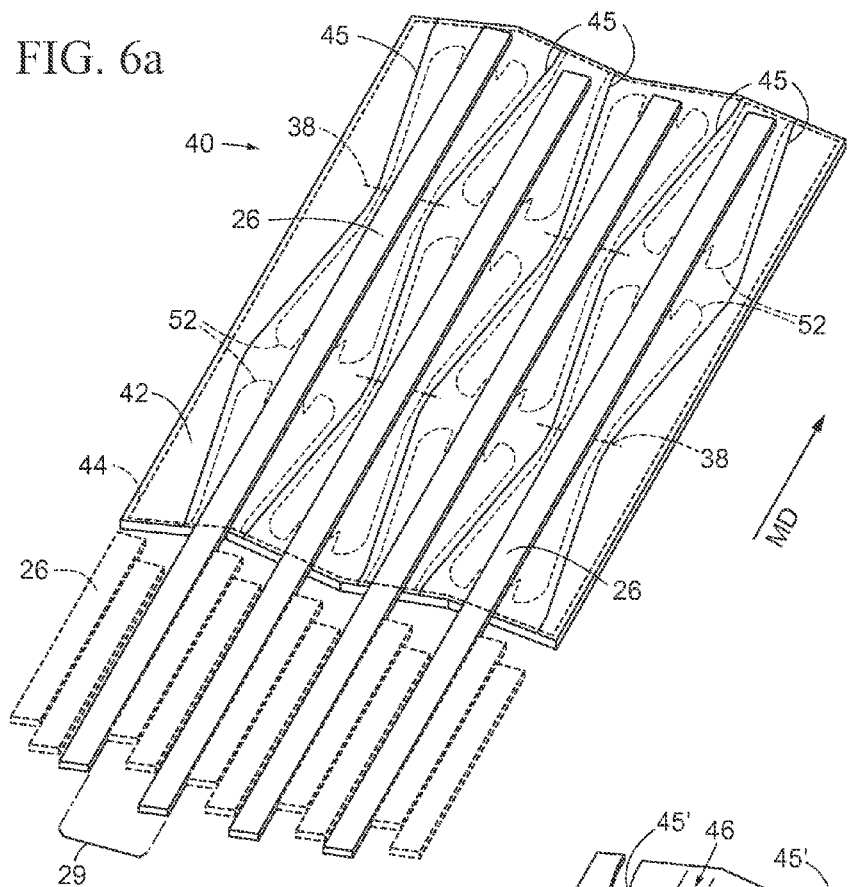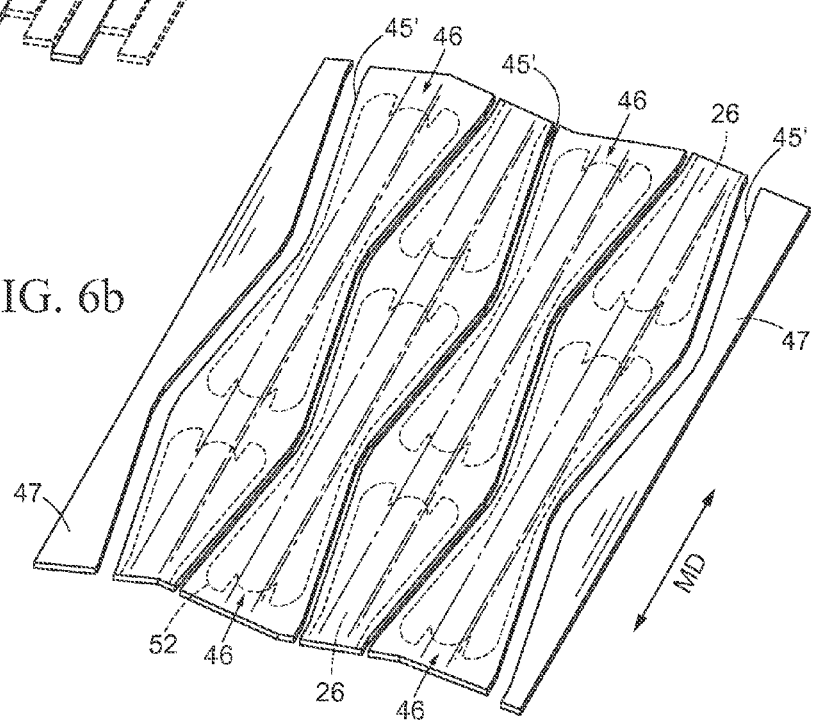

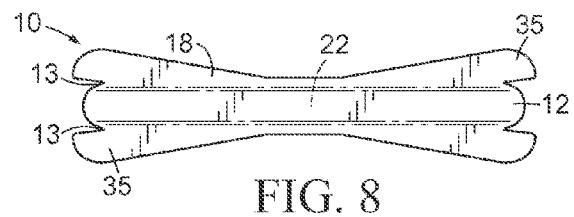
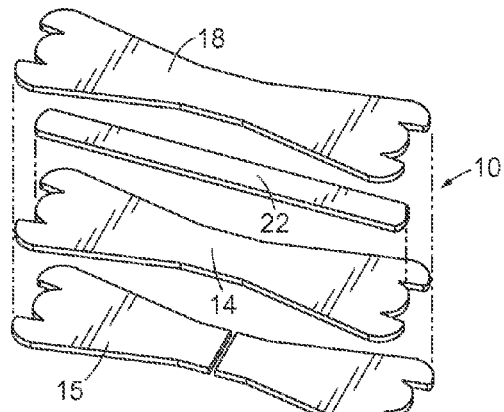
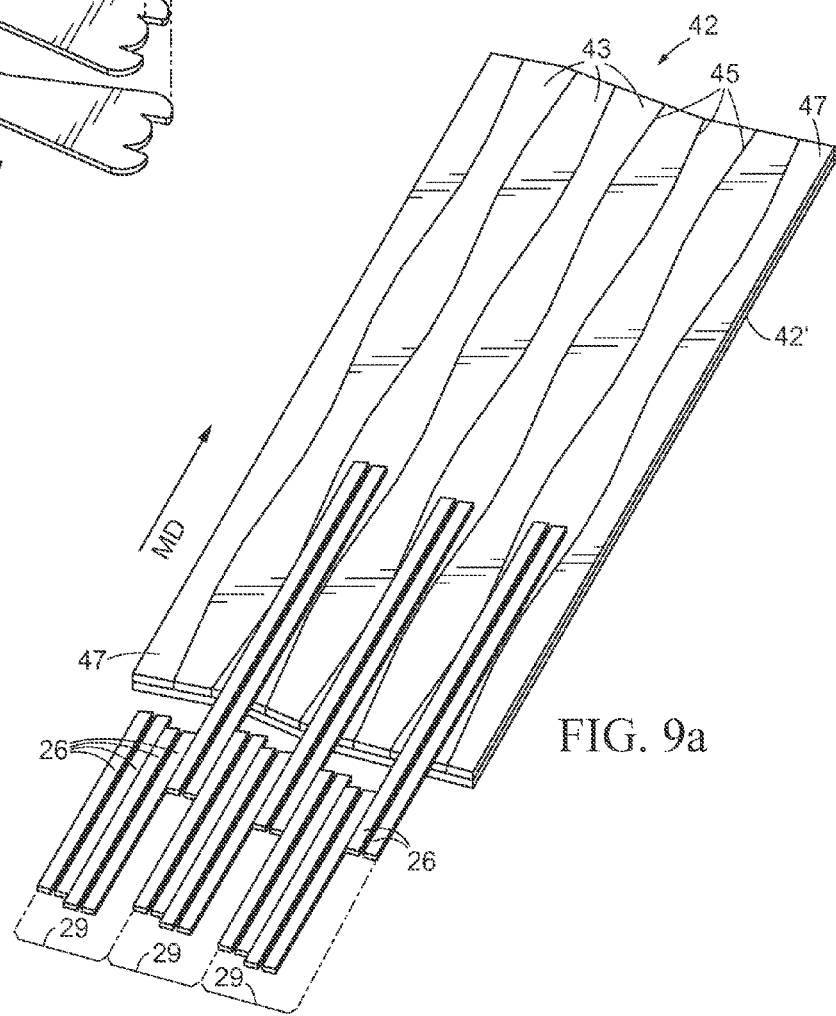

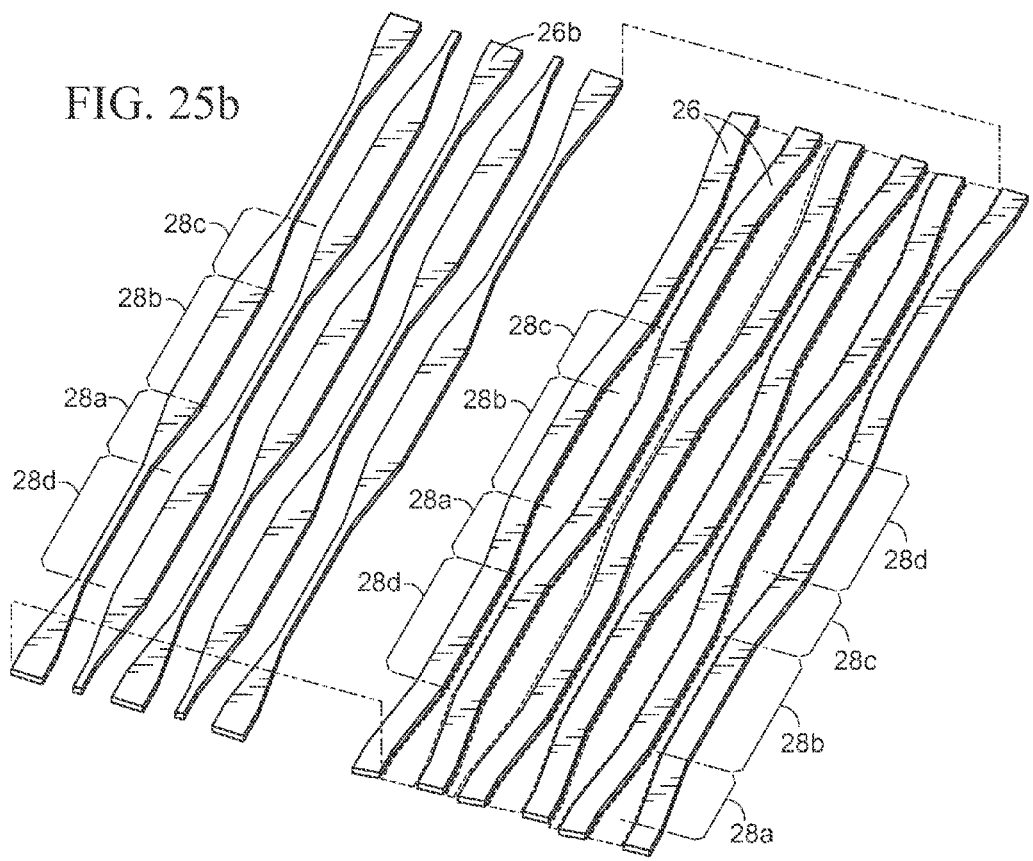
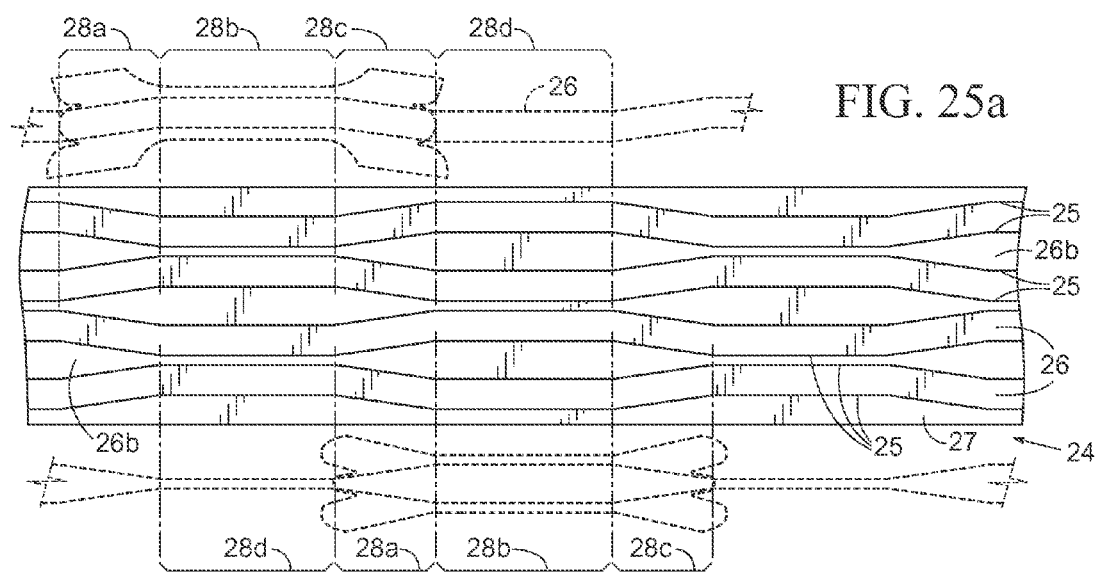

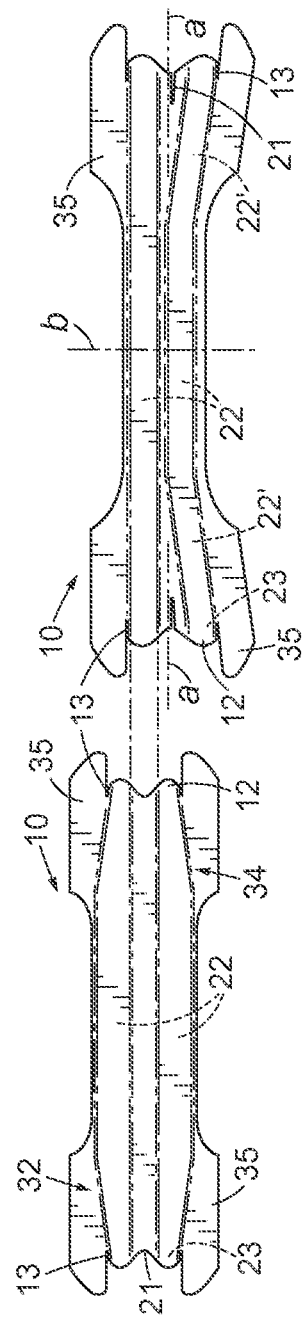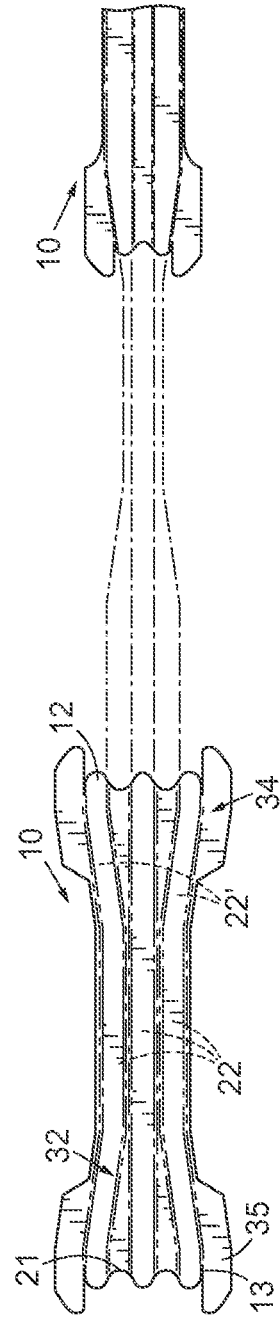

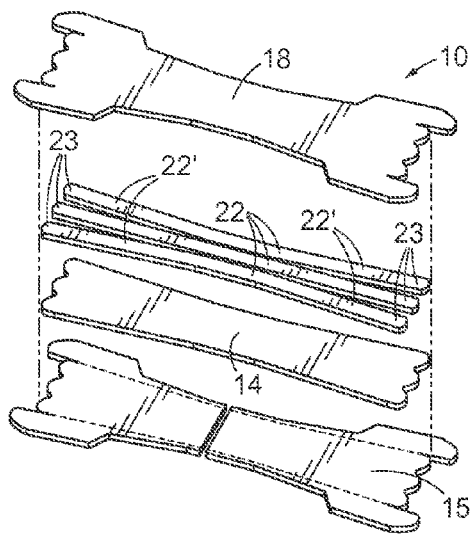
FIG. 39
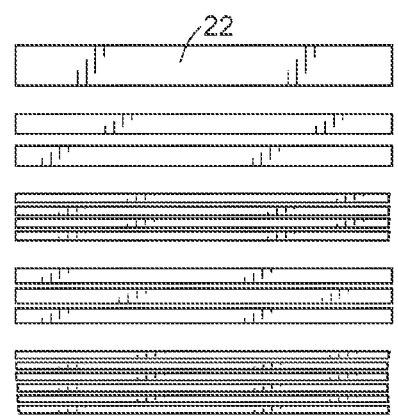
FIG. 40
FIG. 41
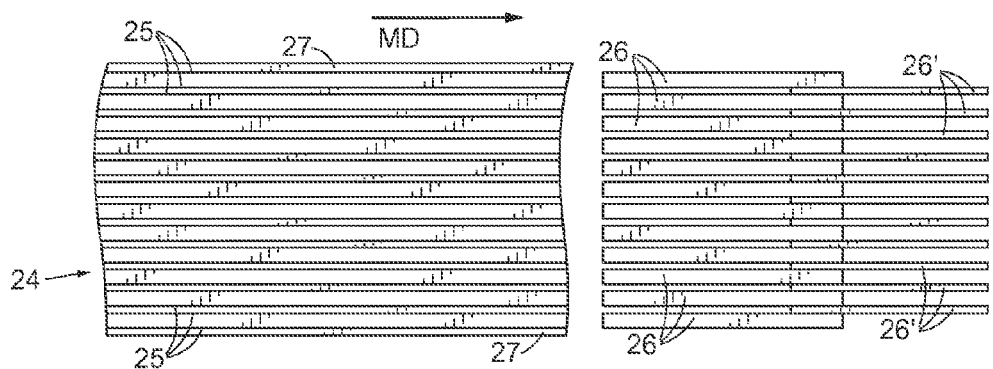

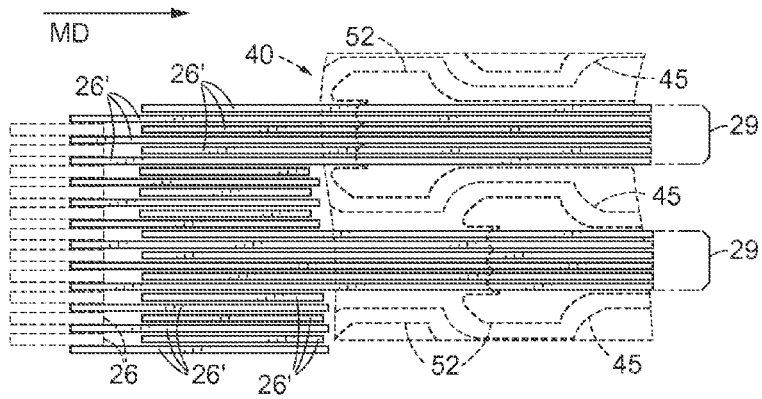
FIG. 43
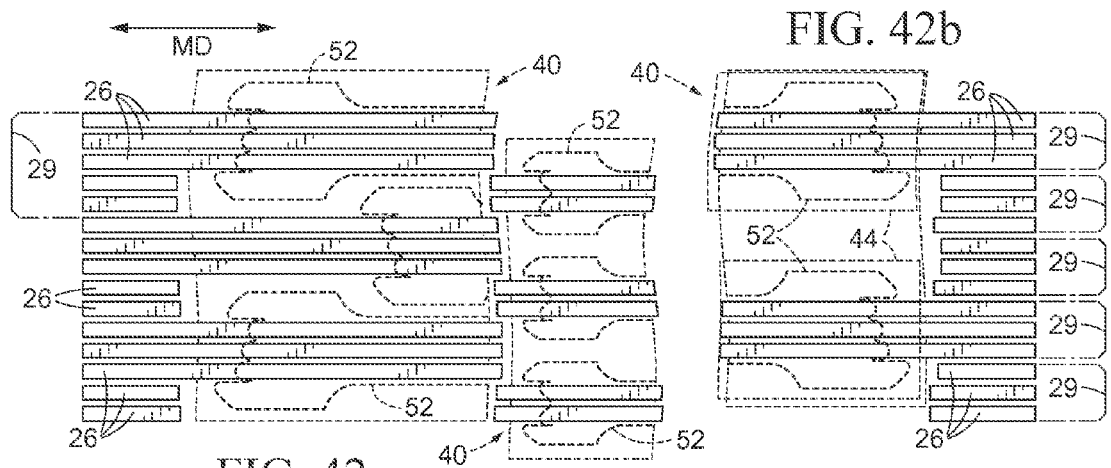
FIG. 42b
FIG. 42a
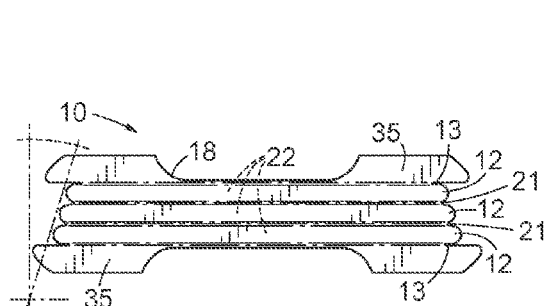
FIG. 44
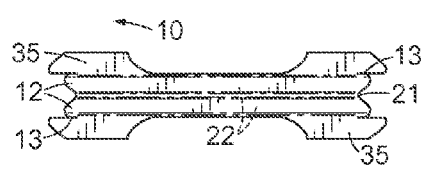
FIG. 45
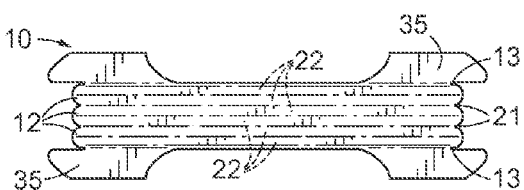
FIG. 46

NASAL DILATOR AND METHODS OF FABRICATING MEDICAL DEVICES

RELATED APPLICATIONS

This application is a Continuation of U.S. Non Provisional patent application Ser. No. 12/964,746 filed 10 Dec. 2010.

FIELD OF THE INVENTION

The present invention relates generally to converting elongated material webs into finished parts or devices such as may be used in the medical, high-technology, electronics, automotive or aerospace industries. The methods are particularly suited to the converting of elongated sheets or rolls of thin flexible materials such as papers, films, foils, tapes, synthetic fabrics and the like, including those having an adhesive substance disposed thereon, into mass produced medical devices such as electrodes, transdermal devices, wound care dressings and closures, etc. The present invention specifically relates to apparatus and methods of dilating external tissue in humans, including methods of fabricating tissue dilator devices. As disclosed and taught in the preferred embodiments, the tissue dilator devices and methods of fabricating medical devices and tissue dilators are particularly suitable for, and are directed primarily to, external nasal dilators for supporting, stabilizing, and dilating nasal outer wall tissues adjacent and overlying nasal airway passages of the human nose, including the nasal valve and the nasal vestibule areas thereof. The United States Food and Drug Administration classifies the external nasal dilator as a Class I Medical Device.

BACKGROUND OF THE INVENTION

A portion of the human population has some malformation of the nasal passages which interferes with breathing, including deviated septa, swelling due to infection or allergic reactions, or inflammation due to changes in atmospheric humidity. A portion of the interior nasal passage wall may draw in during inhalation to substantially block the flow of air. Blockage of the nasal passages as a result of malformation, symptoms of the common cold or seasonal allergies are particularly uncomfortable at night, and can lead to sleep disturbances, irregularities and general discomfort.

In use the external nasal dilator is flexed across the bridge of the nose, extending over the nasal passage outer wall tissues on each side of the bridge, and held thereto by an adhesive. A resilient member (also referred to as a spring member, resilient band, or spring band) is embedded in, or affixed to, the device. The resilient member may be bisected lengthwise into two closely parallel members. Flexure creates spring biasing forces in the resilient member, extending from the middle to the opposite end regions of the device, pulling outwardly to dilate or otherwise stabilize the outer wall tissues of the nasal airway passages. This decreases airflow resistance within the nasal passages and produces a corresponding ease or improvement in nasal breathing.

The resilient member typically produces between 15 grams and 35 grams of resiliency or spring biasing force. Constructing a nasal dilator with less than 15 grams of spring biasing force may not provide suitable stabilization or dilation, while greater than 35 grams would be uncomfortable for most users. Using a more aggressive adhesive, a greater amount of adhesive, or greater adhesive surface area so as to withstand greater spring biasing increases the likelihood of damage to the tissue upon removal of the device.

Examples of present external nasal dilators are disclosed in U.S. Pat. Nos. 6,453,901, D379513, D429332, D430295, D432652, D434146, D437641 and U.S. patent application Ser. Nos. 08/855,103, 12/024,763, 12/106,289, and 12/402,214, the entire disclosures of which are incorporated by reference herein. A minority of the external nasal dilator prior art is adaptable for mass production and thus commercialization in the present consumer retail market. Examples of commercialized nasal dilators, know collectively as nasal strips, include devices disclosed in U.S. Pat. Nos. D379513, 6,453,901, 5,533,503, 5,546,929, RE35408, 7,114,495 and certain devices based upon Spanish Utility Model 289-561 for Orthopaedic Adhesive.

While these example devices provide dilation or stabilization to nasal outer wall tissues in a majority of users, there is a need in the art both to provide variety and complexity in commercially feasible dilator devices and to overcome certain inherent limitations of nasal dilation, including: limited skin surface area adjacent the nasal passages to engage a dilator device; a limited range of spring biasing force that is both effective and comfortable; the dynamic relationship between adhesive engagement and spring biasing peel forces as affects efficacy, comfort and engagement duration; and economically producing complex dilator devices on a mass scale. The present invention discloses novel dilator devices and methods of manufacturing dilator devices which address unmet needs in the art and the limitations of nasal dilation.

A particular inherent limitation of the external nasal dilator is that spring biasing creates peel forces at its opposite end regions, together with some tensile forces, which act to disengage the device from the skin surface. Dilator devices disclosed in U.S. Pat. Nos. 5,533,503 and 6,453,901, and U.S. patent application Ser. No. 12/106,289 include design attributes to mitigate the effect of peel forces or to otherwise shift at least a portion of peel forces into sheer forces. Accordingly, a dynamic relationship exists between dilator design, its flexed spring biasing force, and its efficacy. The present invention builds upon the prior art to address this relationship and further enhance dilator function and comfort.

Nasal dilator devices in the prior art are typically symmetric on each side of the device centerline, which is aligned to the centerline of the bridge of the nose. Each half of the dilator on each side of the centerline is the mirror image of the other. Similarly, each long half of the device, bisected along its length, is typically the mirror image of the other. However, symmetry has not been generally incorporated into dilator design so as to gain manufacturing economy. Of limited exception is where a plurality of dilator devices are die cut on common lines corresponding to their long edges. However, this technique is facilitated by the device having a constant width along its length; a dilator design having wider end regions and a narrower mid section is generally more comfortable and more effective. The present invention discloses novel means of using symmetry in medical device design, and incorporates symmetry into methods of manufacturing dilator devices on common longitudinal lines.

There has also been a continuing need in the art to develop efficient ways of fabricating complex nasal dilator resilient members and incorporating them into mass produced nasal dilators. Complex resilient members are disclosed in the prior art, but not generally practiced in commercially available nasal strip products. For example, FIGS. 12, 17, 20 and 22 of U.S. Pat. No. 6,453,901 illustrate complex resilient member structures in dilator devices, including a method (illustrated in FIG. 16) of forming continuous interconnected resilient members. However, a significant quantity of material extending around and between the interconnected resilient members is lost. The preferred and commonly used material from which resilient members are fabricated carries a significantly greater cost per unit of measure than other materials used in the device. Accordingly, simple resilient member structures prevail in commercialized dilator devices. The present invention discloses means by which to economically mass produce complex resilient member structures with a material usage-to-waste ratio consistent with the fabrication of simpler structures.

The total cost of a medical device is generally the sum of the cost to manufacture (or convert) the device plus the cost of the material used. Material cost includes that which goes into the finished device plus that which is wasted in the converting process. A dynamic relationship exists between converting cost (setup, calibration, registration and alignment, material handling and fabrication time), and material cost; manufacturers (or converters) often obtain efficiency in one area at the expense of the other. Medical devices are typically die cut in cookie-cutter fashion to reduce converting time, but at the expense of material waste extending around and between finished parts. The present invention discloses various methods to reduce material waste while minimizing any additional converting time.

A common practice is to fabricate external nasal dilators having a material layer above as well as below the resilient member. The two layers are die cut simultaneously, largely to shorten converting time. Thus each material layer comprises about 1.66 square inches of material (based on average overall device dimensions of about 2.63"L×0.63"W), for a total of about 3.31 square inches of material per device. The present invention discloses means to reduce material in at least one of the layers with only a modest increase in corresponding converting time.

Similarly, nasal dilator resilient members are traditionally formed from a continuous strand of material equal to each member's finished width. A plurality of strands are slit along common long edges, then separated and repositioned laterally across the fabrication matrix. Repositioning may constitute a separate and additional converting operation, which carries a cost. The present invention discloses means whereby to slit and position strands in the converting process simultaneously, without a separate and additional operation. The present invention further discloses means to re-incorporate potentially unavoidable resilient member material waste into a subsequent fabrication process which yields additional or complementary dilator devices.

Where a nasal dilator resilient member is fabricated to be centered within the peripheral edges of the finished device, material waste can be up to 73%. This manufacturing technique (called island placement) simultaneously die cuts and registers a plurality of spaced apart components along a material strip, or across and along a material web, so that each component (i.e., the resilient member) is centered within the perimeter edges of another plurality of similarly registered components (material layers which form the rest of the dilator). Island placement requires additional material extending along each side of the finished resilient member plus material extending between successive devices fabricated lengthwise end to end. The additional material is used as a matrix by which to space the finished resilient members apart; the wider the matrix, the poorer the usage-to-waste ratio. Once the resilient members are die cut, the matrix is removed as a whole from around and between the spaced apart resilient members and discarded as necessary waste.

By example, a finished resilient member may be about 2.25" long×about 0.24" wide, for a total of 0.54 square inches of material. Where resilient members are formed from a continuous strip of material, adding 0.125" to each long edge of the strip increases strip width to 0.49". Individual resilient members must also be spaced apart lengthwise by about 3" from center to center to allow adequate perimeter space to form a finished dilator device being about 2.63" long. This means 1.47" sq. (3"×0.49") of material is used to fabricate and position a resilient member comprising 0.54" sq. of material. The resulting usage-to-waste ratio is nearly 1:4, where about 27% of the material is used for the finished resilient member and about 73% of the material is wasted. The present invention discloses means to improve resilient member material waste, particularly in the fabrication of complex resilient member structures, where the higher per unit material cost has the greatest impact on manufacturing economy.

Similar to the fabrication of island-placed components, finished nasal strip devices are typically manufactured in a continuous process which spaces one device from another by about 0.125" on all sides so that material not devoted to the device itself (the waste matrix) can be removed as a whole. Finished devices meant to be packaged in the same operation are spaced even farther apart to provide a suitable contact perimeter around each unit so that upper and lower packaging material webs may form an adequate seal. Again, material from which finished devices or device elements are fabricated is often used as the matrix by which to space finished devices apart. Nasal strips fabricated in closer proximity to each other in order to avoid that material waste are often packaged in a separate, dedicated operation, thus incurring a corresponding cost. The present invention discloses means to fabricate medical devices so as to reduce waste, and to simultaneously space finished devices apart so as to seal the devices between packaging webs, without incurring a separate operational cost or the traditional amount of material waste.

SUMMARY OF THE INVENTION

The present invention discloses methods for converting elongated material webs. The methods are particularly suited to mass producing medical devices, particularly the external nasal dilator. Methods are determined in part by device design and device design is shaped by methods so as to create efficiencies and extend material yield. While the manufacturing methods of the present invention are suitable or adaptable to a range of converting applications, and particularly to medical devices, the preferred embodiments are primarily directed to producing complex external nasal dilator devices economically on a mass scale.

Manufacturing methods of the present invention revolve around forming continuous slits in an elongated flexible material web. The slits alter the material web into a plurality of adjacent, or laterally contiguous, elongated strands. The strands are separated from the material web and combined with at least one additional material web in a continuous process which forms a material laminate. The strands may also be combined with other strands slit from a different material web and then combined with another material web to form a material laminate. The material laminate may be die cut into finished devices or it may be slit into laminate strands which are subsequently die cut into finished devices. Laminate strands may also be combined with another material web and then die cut into finished devices. The material laminate or laminate strands may be combined with upper and lower packaging material webs so as die cut and package the finished devices concurrently.

An elongated flexible material web generally consists of a single material layer with an adhesive substance disposed on one surface and a protective paper liner releasably secured to the adhesive. A material web may also comprise more than one material layer. The continuous slits extend vertically through at least a portion of the elongated material web and longitudinally along, or generally consistent with, the machine direction of the web without intersecting the outside long edges or an adjacent slit. Otherwise the slits may be straight or may have divergent, angled or curved segments. The slits may be parallel to each other or may diverge laterally from one another. Two adjacent slits define a strand, and the strand may thus be straight, divergent, have a gradient width or a varying width.

An elongated strand or laminate strand consists of a plurality of interconnected objects integrated into the strand. The objects correspond to an element, layer, member or component of a medical device. Accordingly, the continuous slits follow criteria determined by the design of the object and the design of the medical device to which the object is a part. That criteria includes: forming the object to dimensions appropriate to the element, layer, member, component or finished device; defining at least a portion of the peripheral dimensions of the object or finished device; pre-positioning or aligning objects to each other or to a registration point where the finished device will be die cut; and creating a predetermined lateral spacing between strands, and ultimately objects, as the strands are separated from a material web and combined into a material laminate. Predetermined spacing is a function of strand width and/or the collective width of a group of strands.

Since a strand or laminate strand consists of a plurality of interconnected objects, then each continuous slit in an elongated web or material laminate thus forms, as well as defines, at least a portion of one long edge of two objects adjacent each other (one to each side of the slit). At least portions of these long edges of adjacent objects or finished devices are thus formed on common lines. Again, the interconnected objects correspond to an element, layer, member or component of a medical device, or the device itself.

The interconnected objects of a strand or laminate strand are completed by severing, such as by cross slits extending between the long edges of a strand or laminate strand, or by die cut lines contained at least in part within the width of a strand or laminate strand, or by enclosed die cut lines formed in a material laminate or laminate strand. Die cut lines generally form finished or semi-finished devices in a material laminate or laminate strand, but die cut lines may also form, in whole or in part, elements, layers, members, or components of a finished device in a material web, a strand, or some combination of material webs and elongated strands.

One purpose of forming and combining strands and material webs into material laminates and laminate strands is to eliminate material waste and extend material yield without increasing converting time to the point of offsetting savings gained. Particularly effective is forming strands of the most expensive materials, then separating or dividing these strands into multiple material laminates consisting of less expensive materials. Forming strands in a material web and dividing them into multiple laminates is also an effective alternative to using the web as a matrix by which to space apart a plurality of components to be die cut therefrom.

The present invention discloses means for separating strands from a material web without having to reposition them in a separate, dedicated operation. Continuous slits form a plurality of adjacent, or laterally contiguous, strands in a material web such that the plurality consists of consecutive, or adjacent, groups of strands. One or more select strands is separated from each group (e.g., every other, every one-in-three, every two-in-eight, etc.) such that the separated strands are laterally spaced apart, and thus pre-positioned, or registered, when combined with other material webs. The individual widths of the separated strands and the collective width of one or more of the consecutive groups of strands defines the spacing between the separated strands. That spacing, together with strand width, corresponds to dimensions and other design attributes of finished devices or the objects which make up finished devices.

The present invention further teaches, depicts, enables, illustrates, describes and claims new, useful, and non-obvious apparatus for dilating external tissue. The present invention builds upon the prior art and addresses unmet needs in the art. The nasal dilator of the present invention comprises an engagement element, a functional element, and a directional element. The functional element of the dilator comprises resilient means including at least one resilient member extending along its length and which provides the spring biasing force of the device. In use, the engagement element affixes the dilator to the nose of a user through engagement means. The directional element affects, alters, directs or redirects the spring biasing properties of the dilator so as to increase its overall efficacy, useful duration, comfort, and ease of use.

Nasal dilators of the present invention comprise a laminate of vertically stacked material layers which form the dilator as a unitary, single body truss. Dilator layers are formed in whole or part from elongated material webs, elongated strands, material laminates or laminate strands. Dilator layers are preferably secured to one another by an adhesive substance disposed on at least portions of at least one flat surface side of at least one layer, and the resulting laminate forms a unitary, or single body, truss. Each layer includes one or more members, and a member may further include one or more components. Each of the engagement, functional, and directional elements is defined by at least a portion of at least one layer of the device.

The single body truss comprises horizontal regions, including first and second end regions adapted to engage outer wall tissues of first and second nasal passages, respectively, and an intermediate region adapted to traverse a portion of a nose located between the first and second nasal passages and joining the end regions. The truss is capable of resilient deformation such that when flexed it returns substantially to its pre-flexed state. In use the dilator stabilizes nasal outer wall tissues, and may further expand or dilate the nasal outer walls to prevent tissues thereof from drawing inward during breathing. The truss is configured to be comfortable on the skin surfaces engaged and to be easily removed with little or no stress thereto.

It is the principal objective of the present invention to provide novel methods of converting elongated flexible material webs so as to reduce manufacturing cost, to return a greater number of finished devices or parts thereof per a given quantity of material and to minimize the percentage of material discarded as waste. A more specific objective of the present invention is to fabricate at least portions of finished medical devices or portions thereof on common longitudinal lines in a continuous repeating process. A further objective of the present invention is to provide novel nasal dilator devices having complex functional element structures, manufactured using novel, and non-obvious methods having greater efficiency and economy than traditional methods.

It will be apparent to the skilled person in the art of medical device design or converting that the manufacturing methods of the present invention rely on well established rotary techniques for winding, unwinding, slitting, peeling, separating, laminating, etc., and the die cutting or punching of material webs using rotary or flat-bed machinery. It is understood that fluid or pneumatic modular automation for material feed or handling, including components and systems, and electronic or computerized controls may also be applicable.

The present invention is not limited to the illustrated or described embodiments as these are intended to assist the reader in understanding the subject matter of the invention. The preferred embodiments are examples of forms of the invention comprehended by that which is taught, enabled, described, illustrated and claimed herein. All structures and methods which embody similar functionality are intended to be covered hereby. The manufacturing methods depicted, taught, enabled and disclosed herein, while particularly suitable for dilator devices, may be applied to a range of medical devices. The nasal dilators depicted, taught, enabled and disclosed herein represent families of new, useful and non-obvious devices having a variety of alternate embodiments. Dilator elements, layers, members, components, materials, or regions may be of differing size, area, thickness, length, width or shape than that illustrated or described while still remaining within the purview and scope of the present invention. The preferred embodiments include, without limitation, the following numbered discrete forms of the invention, as more fully described below.

Some embodiments of the present invention are arranged in groups so as to illustrate manufacturing steps. Each group builds upon the previous by introducing a new or subsequent element, technique, or variation thereof. Accordingly, later embodiments frequently refer to, or cross reference, previous embodiments. It will be obvious to the skilled person in the art that techniques, methods, processes, etc., may be applied, interchanged or combined from one embodiment or group thereof to another. The width of material webs in the drawings are generally shown only wide enough to illustrate the subject at hand. In practice, said widths may be generally greater, and in some cases lesser. The longitudinal extents of material webs are shown fragmentary.

For descriptive clarity, certain terms are used consistently in the specification and claims: Vertical refers to a direction parallel to thickness, such as the thickness of a finished device, a material web, material layers, or a material laminate. Horizontal refers to the length of a finished device or a direction parallel thereto. Lateral refers to width, such as that of a finished device or a material web, and to a direction parallel to the cross direction (XD) of a material web. Longitudinal refers to length, such as that of a finished device, or the length or machine direction (MD) of a material web, or a direction perpendicular to width or lateral extent. A longitudinal centerline is consistent with the long axis of a finished device or material web, bisecting its width midway between the long edges. A lateral centerline bisects the long edges of a finished device or material web midway along its length, and is perpendicular to the longitudinal centerline. An object or objects referred to as adjacent or consecutive another generally means laterally, consistent with the width of a finished device or a material web. Objects referred to as successive are generally oriented lengthwise, end to end, parallel to the machine direction (MD) of a material web.

Broken or dashed lines are used in the drawings to aid in describing relationships or circumstances with regard to objects. A dash followed by three short spaces with two short dashes therebetween indicates separation for illustrative purposes, such as in an exploded view, or to indicate an object or objects removed or separated from one or more other objects for clarity, or as the result of a process or method. A line of successive short dashes with short spaces therebetween may indicate a hidden object, such as one underneath another; or for clarity, to illustrate a location, such as the space an object will occupy, would occupy, or did occupy; or for illustrative purposes, to indicate an object as 'invisible' so that objects underneath it may be seen. A long dash followed by a short space, a short dash and another short space is used to call out a centerline or an angle, or to indicate alignment; when accompanied by a bracket, to call out a section, segment or portion of an object or a group of objects, or to illustrate a spatial relationship between one or more objects or groups of objects.

In the drawings which accompany this disclosure, like objects are generally referred to with common reference numerals, except where variations of an object must be distinguished from one another. In describing manufacturing methods, Machine Direction is indicated in the drawings by the letters 'MD' adjacent a directional arrow: a single arrowhead indicates preferred direction; a double arrowhead indicates flow may be in either direction. Drawings are not rendered to scale, and where shown, the thickness of objects is generally exaggerated for illustrative clarity.

BRIEF DESCRIPTION OF THE SEVERAL VIEWS OF THE DRAWING

FIG. 1 is a perspective view of a portion of a face with a nasal dilator in accordance with the present invention engaged to the nose.

FIG. 2 is an exploded perspective view of the nasal dilator of FIG. 1.

FIG. 3 is a perspective view of the nasal dilator of FIG. 2.

FIG. 4 is a plan view of a pair of the nasal dilator of FIG. 3 including fragmentary portions of where successive dilator units may be included therebetween.

FIGS. 5b-5d are fragmentary perspective views illustrating subsequent and final manufacturing steps to the first form of manufacturing method.

FIGS. 6a-6c are fragmentary perspective views illustrating alternative steps to those of FIGS. 5b-5d.

FIG. 7 is an exploded perspective view of a variation of the dilator of FIGS. 1-4, produced from the alternative steps illustrated in FIGS. 6a-6c.

FIG. 8 is a plan view of the nasal dilator of FIG. 7.

FIGS. 9a-9c are fragmentary exploded perspective views illustrating the initial steps of a second form of manufacturing method in accordance with the present invention.

FIG. 25a is a fragmentary plan view illustrating an overview of a first variation of the fifth form of manufacturing method.

FIG. 25b is an exploded fragmentary perspective view illustrating the separation of elongated material strands of FIG. 25a into two groups.

FIG. 28 is a fragmentary plan view illustrating a relationship between seventh and eighth forms of nasal dilator devices in accordance with the present invention, produced from the manufacturing method of FIG. 27.

FIG. 29 is a fragmentary plan view illustrating a relationship between ninth and seventh forms of nasal dilator devices in accordance with the present invention, produced from the manufacturing method of FIG. 27.

FIG. 39 is an exploded perspective view of the eleventh form of nasal dilator produced from the variation of method described with regard to FIGS. 33-35.

FIG. 40 is a plan view illustrating a comparison of resilient member structures.

FIG. 41 is a fragmentary plan view illustrating an initial step of a sixth form of manufacturing method in accordance with the present invention, based on the methods of FIGS. 5a, 9a-9b, and 23a, and on the comparison of resilient bands shown in FIG. 40.

FIGS. 42a and 42b are fragmentary plan views illustrating an overview of a first set of subsequent steps to the sixth form of manufacturing method.

FIG. 43 is a fragmentary plan view illustrating an overview of a second set of subsequent steps to the sixth form of manufacturing method.

FIG. 44 is a plan view of a thirteenth form of nasal dilator in accordance with the present invention, produced from the method described with regard to FIGS. 41-42b.

FIG. 45 is a plan view of a common form of nasal dilator, produced as a second, complementary, device from the method described with regard to FIGS. 41-42a.

FIG. 46 is a plan view of a fourteenth form of nasal dilator in accordance with the present invention, produced from the method described with regard to FIGS. 41 and 43.

FIG. 51 is a plan view of a fifteenth form of nasal dilator in accordance with the present invention produced from the material laminate shown in FIG. 50a.

DETAILED DESCRIPTION OF THE INVENTION

Figure 5A:
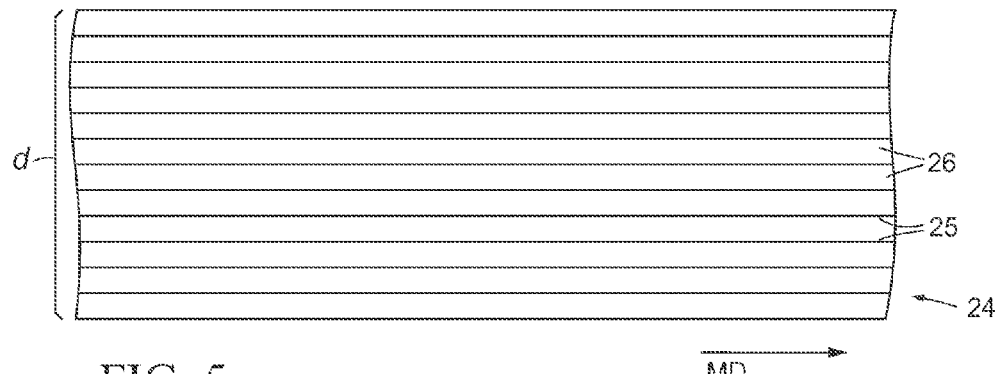
FIG. 5a is a fragmentary plan view of a resilient layer material web illustrating the initial step of a first form of manufacturing method in accordance with the present invention.

An embodiment of a nasal dilator, 10, in accordance with the present invention is illustrated in FIG. 1. Seen in use, dilator 10 is affixed by its engagement element to a nose, 11, illustrated as a portion of a human face. Dilator 10 includes a directional element in the form of a horizontal protrusion, 12, which separates slightly from the skin thereat as a result of the device's functional element applying spring biasing forces to the nasal wall tissues when dilator 10 is flexed across the bridge of the nose.

FIG. 2 shows that dilator 10 comprises a laminate of vertically stacked layers, indicated by a broken line, v, the layers including: a base layer comprising at least one base member, 14, a resilient layer comprising at least one resilient member, 22, and a cover layer comprising at least one cover member, 18. A base, resilient or cover member may further include one or more components as part thereof. Portions of one layer may overlap another layer. A protective layer of release paper, 15, removably covers exposed adhesive from any other layer preliminary to using the dilator. The shape and dimensions of release paper 15 may correspond to the periphery of dilator 10 or may exceed the periphery of one or more dilators 10. Release paper 15 may be bisected into two parts, which may overlap or abut, so as to facilitate removal from the dilator prior to use. Dilator layers may be secured to each other by any suitable means such as stitching or fastening, heat or pressure bonding, ultrasonic welding, or the like, but are preferably laminated by an adhesive substance disposed on at least one flat surface side of at least one layer. At least a portion of one flat surface of the base or cover layer is preferably laminated to one of two flat surfaces of the resilient layer. Dilator layers are preferably aligned along a longitudinal centerline, a, shown by a broken line.

The peripheral dimensions of dilator 10 are defined by the cover layer, but may also be defined by the base layer, or a combination of layers or portions thereof. The base and cover layers may have the same dimension or peripheral shape as each other, or the base and resilient layers may be identical, or all three layers may have different peripheral dimensions. The base and cover layers of dilator 10 may be interchanged, or one or the other may be eliminated in whole or in part.

All or part of the base and cover layers, either separately or combined, together with a biocompatible adhesive thereon for affixing dilator 10 to the skin, provide the primary engagement element of dilator 10. Adhesive may also be used on the functional element, should it contact the skin directly, to thus aid engagement of the device to the skin. The engagement element, by itself, does not provide nasal dilation, although depending on the material used, could provide some tissue stabilization. The functional element, by itself and affixed to the skin by adhesive, will not generally remain engaged thereto. Accordingly, nasal dilators of the present invention combine separate functional and engagement elements in a single body device.

Where the base layer has a significantly lesser surface area than the cover layer, adhesive on the skin-engaging side of the base layer may be optionally eliminated. With or without adhesive, the base layer may also serve as a compressible buffer between the device and the skin, as has been historically common in medical devices which remain in contact with the skin for any length of time. Dilators of the present invention are designed so that no portion of a layer extends substantially onto the skin surface areas of the cheek.

The preferred material for the base and cover layers is from a group of widely available medical grade flexible nonwoven synthetic fabrics that are breathable and comfortable on the skin. Any suitable fabric or thermoplastic film, including various clear films, may be used. A pressure sensitive adhesive, biocompatible with external human tissue, is preferably disposed on at least one flat surface side of the material. A protective layer of release paper liner covers the adhesive. The preferred materials are typically available in rolls wound in the machine direction (MD) or warp, which is perpendicular to the cross direction (XD) or fill, of the material. The manufacturing methods of the present invention have the base and cover layers fabricated parallel to the machine direction of the material, but they may be fabricated parallel to either the warp or fill of the material.

The preferred material for the resilient layer is a widely available biaxially oriented polyester resin (PET), a thermoplastic film having suitable spring biasing properties across both its warp and fill. PET is used in a number of medical device applications and is particularly suitable for nasal dilator devices. The film may have a pressure sensitive adhesive disposed on one or both surfaces with a protective layer of release paper liner covering the adhesive. PET may be laminated to the preferred base layer material, from the adhesive side thereof to the non-adhesive side of the base layer material, so that the resilient and base layers of dilator 10 may be fabricated simultaneously to the same peripheral shape.

The functional element of dilator 10 is configured to provide spring return biasing force within a suitable range as described hereinbefore. Spring biasing force is generated from the resilient layer of dilator 10, the amount of which is determined by configuration of the resilient member or members, and the length, width and thickness thereof. The resilient layer preferably has an adhesive substance disposed on at least a portion of at least one of two opposite flat surface sides for engaging or laminating it to other layers, members or components of dilator 10, or for adhering to the nasal outer wall tissues. FIG. 2 shows resilient member 22 having terminal end portions, 23, which align with a portion of the end edges of dilator 10, conforming substantially to protrusion 12 as shown in FIGS. 1, 3 and 4.

FIGS. 3 and 4 show that the layers of dilator 10 form a unitary, or single body, truss, 30, having a horizontal length, or longitudinal extent, c, indicated by a bracket. Truss 30 has contiguous regions indicated approximately by broken lines and brackets, including a first end region, 32, a second end region, 34, and an intermediate region, 36, which joins first end region 32 to second end region 34. The width of intermediate region 36 is preferably narrower than the width of end regions 32 and 34. Portions of any layer may define a region of the truss or a portion thereof. The layers, members or components of dilator 10 may extend from one region to another. End regions 32 and 34 are adapted to engage outer wall tissues of the first and second nasal passages respectively. Each end region has an end edge, 33.

Dilator 10 may further include a directional element through configuration or modification to its layers or to the material webs from which the layers are fabricated. A directional element may be formed by cuts, notches, openings, or the like, to create a discontinuity of shape of material, a material separation, or a protrusion. A material separation may be formed in a dilator layer or a corresponding material web in the course of fabricating a layer, or formed in a material laminate, or formed as dilator 10 or its layers are die cut from a material laminate. End edge 33 includes a directional element in the form of a material separation, 13, formed as a back cut extending inward from each end edge 33 and positioned between one long edge of terminal end portion 23 and the corresponding upper or lower tab extension, 35, adjacent thereto. Material separations 13 and terminal end portion 23 together define protrusion 12 at end regions 32 and 34 of truss 30. Tab extensions 35 preferably extend horizontally beyond protrusion 12.

As a directional element defined by material separations 13, protrusion 12 separates slightly from the skin when dilator 10 is engaged to nose 11, as illustrated previously in FIG. 1. Material separations 13 allow a change in the angle of focused spring biasing forces, at least in part, and thus shifts or transforms at least some of these forces from primarily peel and tensile forces into primarily shear forces. Said change in angle further redistributes or imparts said transformed forces to tissue engaging surface areas of the end regions, such as tab extensions 35, extending beyond the material separation. Spring biasing forces are thus imparted to the lateral width and longitudinal extent of end regions 32 and 34, as opposed to a greater delaminating tendency, such as that from peel forces, being imparted to a lesser extent. Shear forces are more easily withstood by the tissue engaging adhesives disposed on the engagement element of dilator 10 than are peel forces.

A directional element may also be formed in the resilient layer by: varying the dimensions of the resilient layer or a member or component thereof, such as by forming a gradiently tapered width; by the peripheral shape of the resilient member or divergent components extending therefrom; or by utilizing a plurality of resilient members, including resilient members of different thickness or width, with each contributing, to differing degrees, a portion of the total spring biasing force of dilator 10. Multiple resilient members of different widths and thickness affect, or direct, the functional element relative to the dilator's overall peripheral dimensions, the dimensions of the resilient layer, and the total number of resilient member bands. Multiple resilient bands of varied width or thickness also allow greater versatility and precision in achieving a desired spring biasing force, particularly where three or more resilient bands are used.

As seen in FIG. 4, the truss is symmetric on both sides of its lateral centerline, b, and symmetric on both sides of its longitudinal centerline a, both sides being the mirror image of the other. The upper and lower dilators 10 shown in FIG. 4 are laterally spaced apart, as indicated by a bracket, d, extending between their respective centerlines a. That amount of lateral spacing is typical in nasal dilator converting, as discussed hereinbefore, where material from which finished devices or device elements are fabricated is also used as a matrix by which to space finished devices apart.

A bracket and broken lines indicates an example of the dynamic relationship between device design and manufacturing method in the present invention: devices are fabricated to be staggered lengthwise so that portions of long edges corresponding approximately to the end regions thereof are fabricated on common die cut lines. Additionally, the device is configured so that two opposing end regions of two successive device peripheries fit into the space between, and substantially on common lines with, the long edges of the device extending between opposite tab extensions 35. Embodiments of the present invention disclose means for fabricating medical devices on common lines or otherwise in close proximity, followed by means to space rows of finished devices apart to facilitate the packaging thereof. FIG. 4 illustrates how material extending between what would otherwise be laterally spaced devices can be utilized in device construction so as to gain manufacturing efficiency.

FIGS. 5a-5d illustrate a first manufacturing method in accordance with the present invention, applicable to a variety of medical devices, but particularly suited to a dilator device as seen in FIG. 4. FIG. 5a shows a plurality of a continuous slit, 25, formed in an elongated web of resilient layer film, 24, spaced across the width thereof. Slits 25 form a plurality of an elongated resilient layer strand, 26. Strands 26 are laterally contiguous, as shown by a bracket, d, their long edges formed on common longitudinal lines. Continuous slits 25 extend vertically through resilient layer film 24 and parallel to the machine direction thereof. Slits 25 are straight, and strands 26 are shown uniform in width.

Each strand 26 effectively consists of a successive plurality of interconnected resilient members. The width of strand 26 is configured to form resilient members having suitable spring biasing properties when cut to finished length, but also configured so that a predetermined number of laterally contiguous strands 26 have a predetermined collective width. In the present instance, resilient layer film 24 includes a base layer material laminated thereto, so strands 26 also consist of a plurality of interconnected base layer members. The base layer of finished dilators 10 will thus have the same dimension as the resilient layer. Accordingly, an adhesive substance is not required on the exposed side of the base layer material opposite resilient layer film 24, since the cover layer of the finished dilator device may adequately serve as the engagement element.

Figure 5B:
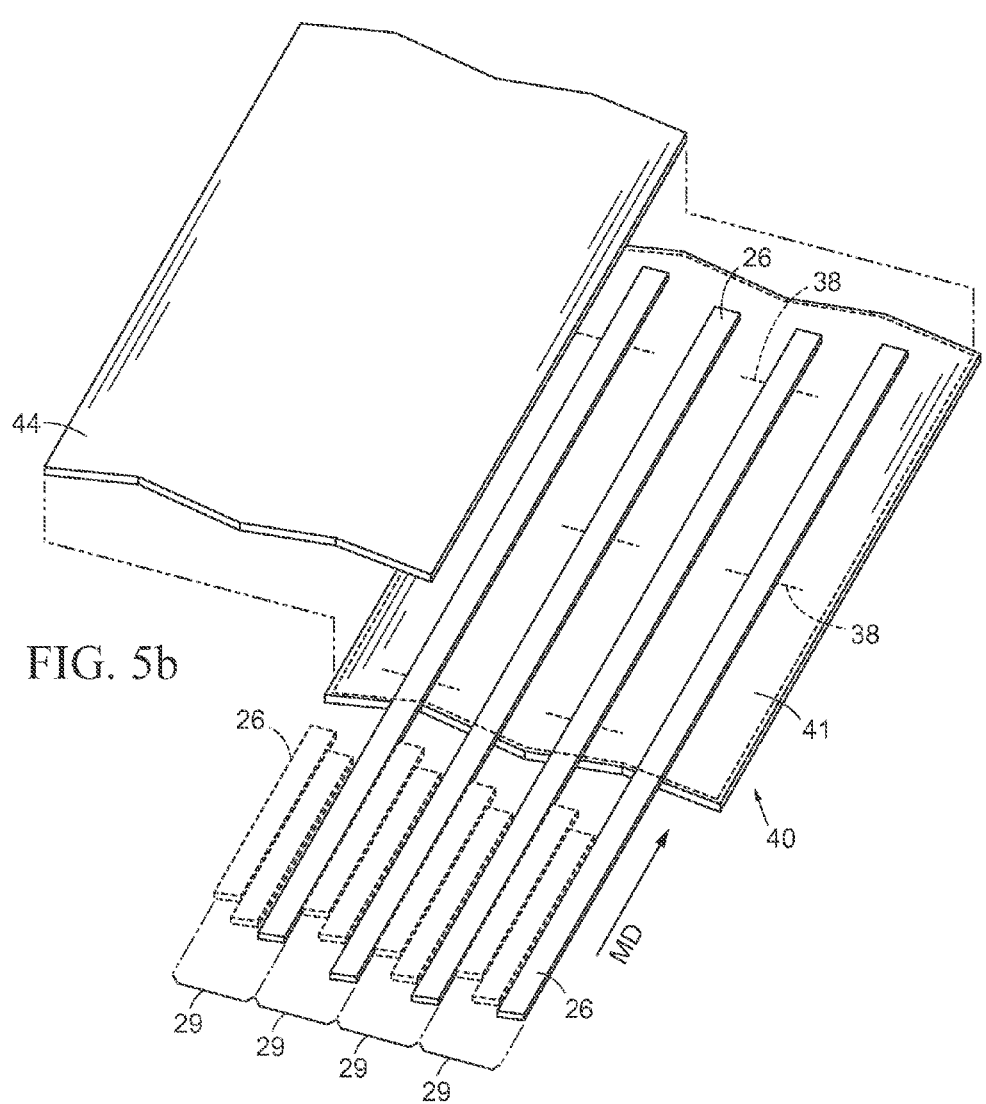

As seen in FIG. 5b, a plurality of an abbreviated slit, undercut 38, is formed at intervals in a separate elongated web of release paper liner, 41. Each undercut 38 is positioned to correspond approximately to the lateral centerline of where a finished dilator will be die cut. Three adjacent, laterally contiguous resilient layer strands 26 form a group, 29, as indicated by broken lines and brackets. While maintaining position relative to the other strands, one strand 26 from each group 29 is separated from resilient layer film 24 and combined with paper liner 41 and an elongated web of cover layer material, 44 to form an elongated material laminate, 40.

Predetermined strands 26 are registered in a lateral, spaced apart, relationship across the width of material laminate 40, the intervals determined by the width of group 29. Cover layer material 44 is laminated by its adhesive side onto separated resilient layer strands 26 and separate release paper liner 41. The remaining strands from repeating groups 29, illustrated by dashed lines, are in position to be separated onto paper liners and the process repeated.

The skilled converter will see that if the base layer material laminated to resilient layer film 24 includes an adhesive layer on the opposite side thereof, the protective release paper liner which covers it must be handled in one of two ways: If slits 25 extend through the paper liner, then respective portions thereof are removed from each of the strands 26 as they are layered onto separate paper liner 41. In this way strands 26 not so separated may be rewound for later processing with their respective paper liners intact. Alternatively, slits 25 may extend through resilient layer film 24 to, but not through, the paper liner (i.e., a kiss cut technique), in which case strands 26 are peeled therefrom and directly onto separate paper liner 41.

Dilator devices of the present invention are manufactured lengthwise, parallel to the machine direction of the materials. To continue the present method, FIG. 5c shows a plurality of a continuous slit, 45, extending vertically through laminate 40 and longitudinally along the machine direction thereof, diverging laterally in a repeating pattern without intersecting the outside long edges of laminate 40 or an adjacent slit 45. Two adjacent slits 45 extend along opposite long edges of each resilient layer strand 26, preferably spaced equidistant therefrom. Slit 45 adjacent each long edge of laminate 40 together form an outside waste strand, 47.

Each slit 45 forms the respective long edges of longitudinally staggered and laterally adjacent finished dilator devices. Cross slits, 48, bisect material laminate 40 at prescribed intervals between adjacent slits 45 to form dilator end edges. Cross slits 48 sever strands 26 to form resilient members 22, protrusions 12, terminal end portions 23 and material separations 13. Continuous slits 45 and cross slits 48 may be formed simultaneously. Cross slits 48 should not cut into the resilient layer strand at material separations 13. End edges 33 could be of a simpler configuration so as to increase the margin of error in this regard. (Less preferable, a single cross slit 48 could be used instead of two, thus forming opposite end edges 33 of two successive finished dilators on a common die cut line.)

As seen more clearly in FIG. 5d, continuous slits 45 and cross slits 48 separate material laminate 40 into a plurality of loose finished dilator units, waste pieces, 49, and waste strands 47 (all of which are shown slightly separated for visual clarity). Adjacent dilators 10 are formed laterally contiguous where their long edges abut, as previously illustrated in FIG. 4. The lateral spacing of resilient layer strands 26, determined by the individual and collective widths thereof, also defines parameters for the width of finished dilator devices and the lateral spacing of slits 45. Waste pieces 49 are preferably punched through laminate 40 and collected, while waste strands 47 may be re-wound. The resultant plurality of finished individual nasal dilators 10 are then captured in bulk.

Figure 6C:
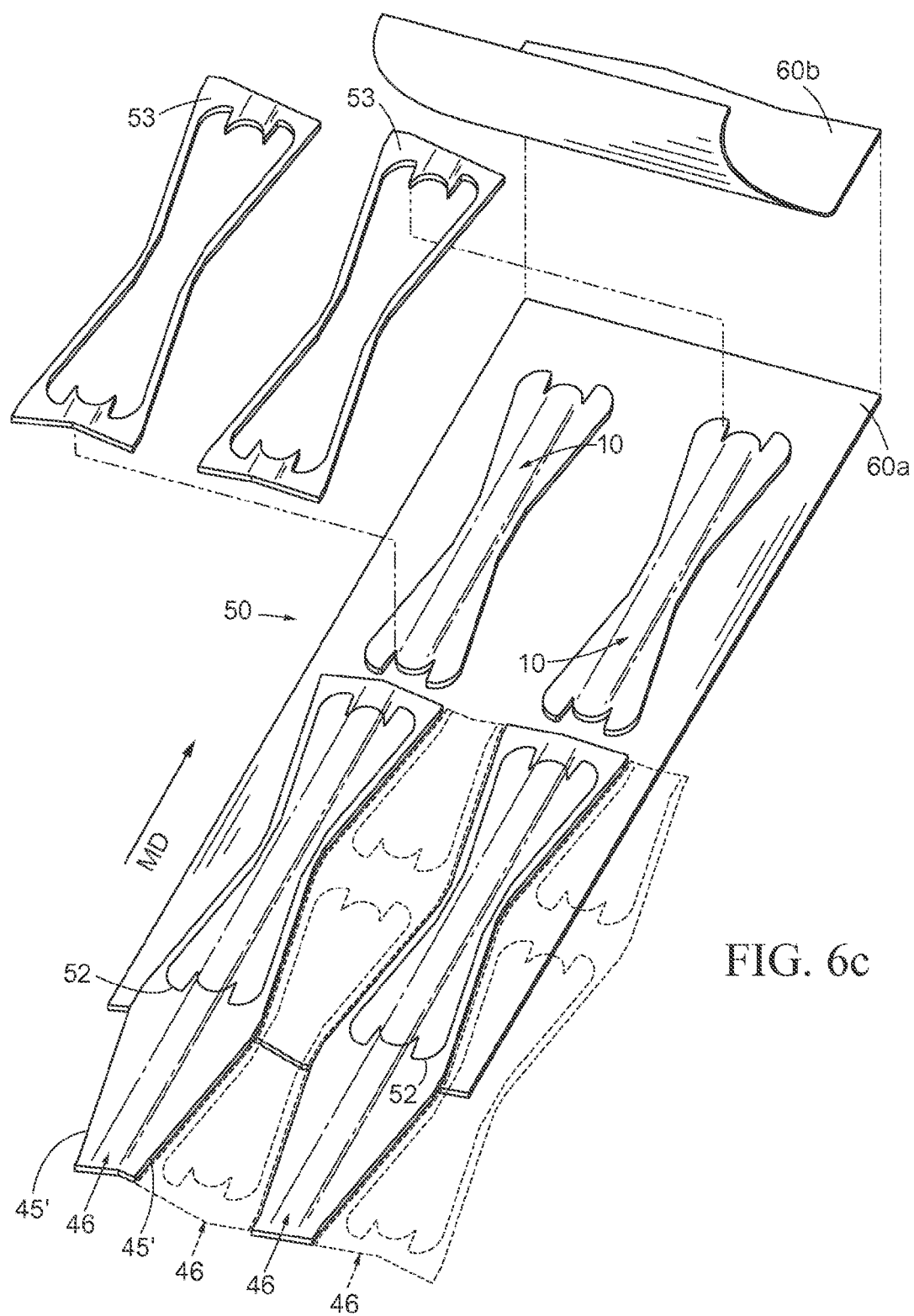

FIGS. 6a-6c illustrate alternative steps to those illustrated in FIGS. 5c and 5d. FIG. 6a shows resilient layer strands 26 separated from groups 29 and incorporated into material laminate 40 as before. In this instance, however, the resilient layer film from which resilient layer strands 26 are slit does not include a base layer material laminated thereto, but preferably does include an adhesive layer on one side.

Strands 26 are combined with elongated webs of base layer material, 42, and cover layer material 44, illustrated by dashed lines, to form material laminate 40. Base layer material 42 has an adhesive substance disposed on what will be the skin-engaging side, protected by a paper liner. Enclosed die cut lines, 52, represented by dashed lines in FIGS. 6a and 6b, form finished dilator units as more particularly illustrated in FIG. 6c. Undercut 38, illustrated by dashed lines, may be formed in the paper liner of base layer material 42 in advance, or concurrent with the formation of die cut lines 52.

FIG. 6b illustrates that continuous slits 45 divide material laminate 40 into a plurality of adjacent, laterally contiguous, laminate strands, 46. For illustrative clarity, laminate strands 46 are shown slightly separated from each other in the drawing figure. Each slit 45 also defines long edges, 45', of two laterally adjacent laminate strands 46. Slit 45 adjacent each outside long edge of laminate 40 defines one long edge of a laminate strand 46, and together with the long edge of laminate 40 forms outside waste strand 47.

FIG. 6c shows every other laminate strand 46, while maintaining its position by the width of the strand 46 therebetween, represented by dashed lines, is separated from laminate 40 and layered an elongated or continuous packaging material web, 60a, to form a fabrication matrix, 50. The remaining laminate strands 46, having the same lateral spacing therebetween, are positioned to be layered onto a packaging material web as well.

FIG. 6c further illustrates that enclosed die cut lines 52 form finished dilators in cookie-cutter fashion within the perimeter of laminate strand 46 at prescribed intervals along the length thereof. Die cut lines 52 extend vertically through laminate strand 46, to, but not through, packaging web 60a. The skilled converter will note that, generally, either of two packaging material webs may form the foundation of fabrication matrix 50 to which finished devices are kiss cut, and that cutting may extend vertically through material laminate 40 from either side, as dictated by preference or machine setup.

Die cut lines 52 sever resilient layer strands 26 into resilient members 22, and form end edges 33, protrusions 12, terminal end portions 23 and material separations 13 of dilator 10 as described previously. Material from around and between die cut lines 52 extending to the opposite long edges 45' of laminate strand 46 is removed as a continuous waste matrix, 53, leaving a plurality of spaced apart finished dilators on packaging web 60*a*. Separating every other laminate strand 46 creates lateral spacing between finished devices so that the second of two packaging webs, 60*b*, may form an adequate perimeter seal with packaging web 60*a* around and between dilators 10, encapsulating them therebetween. Packaging webs may be of any suitable material, such as paper or thermoplastic film, and may be sealed by adhesive, heat bonding, compression, or the like. The sealed packaging webs may be cut, slit, perforated or scored between one or more individual dilators 10 as a means to segment dilators individually or into groups.

The preceding method of fabricating dilator 10 incurs more waste material, in the form of matrix 53, than that shown in FIG. 5*d*. However, the advantage is that finished devices are packaged in the same operation as that from which they are fabricated, with minimal increase in converting cost. FIGS. 7 and 8 more particularly illustrate the finished dilator device. The base layer of dilator 10 has the same periphery as the cover layer. Its bowtie-like shape places progressively more tissue-engaging surface area along the lateral and longitudinal extents of each end region of the truss, similar to the dilator of FIGS. 2-4. Dilator 10 further features a rectangular resilient member 22 having material separations 13 and protrusions 12 as described hereinbefore.

Figure 9B:
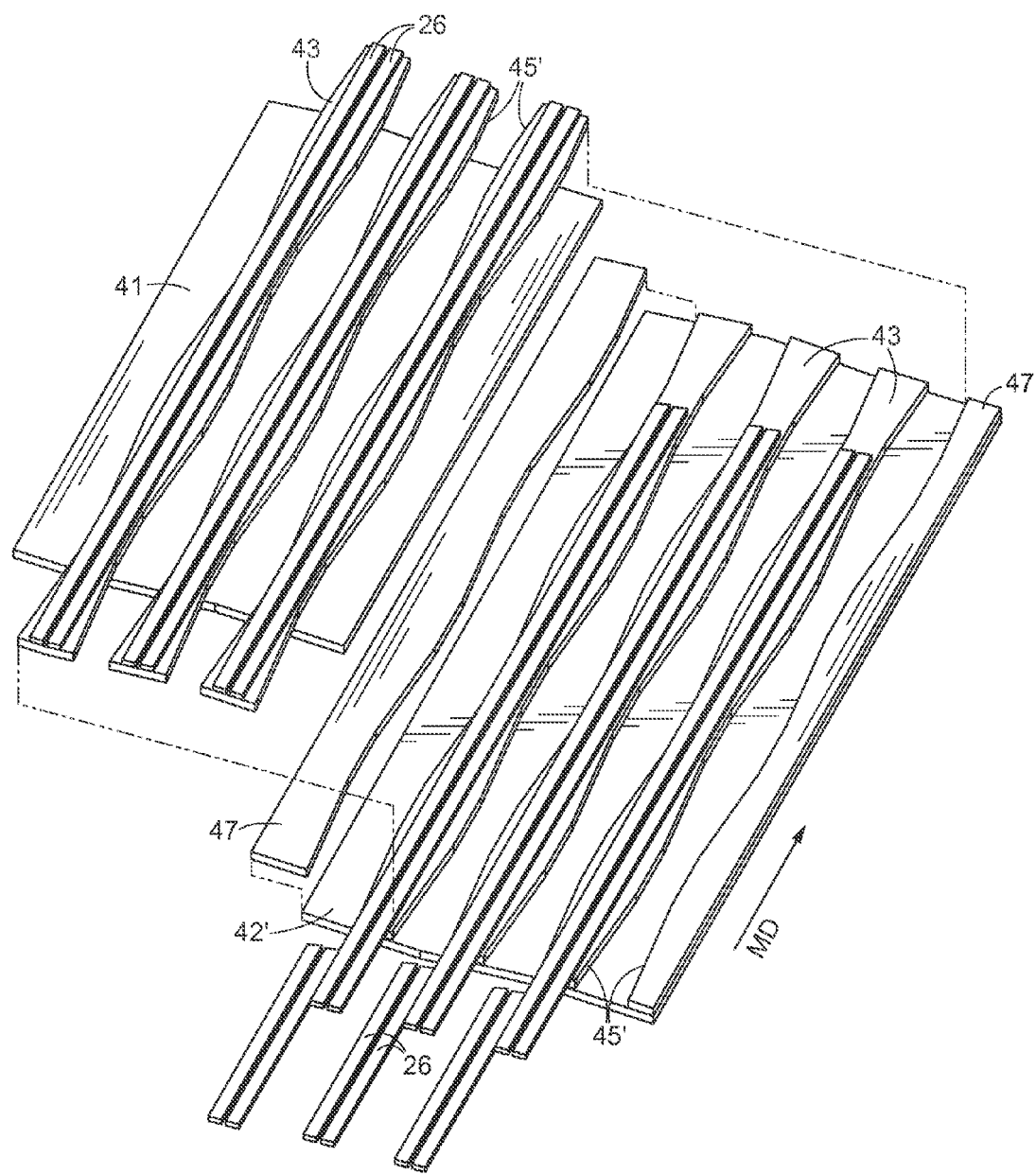
Figure 9C:
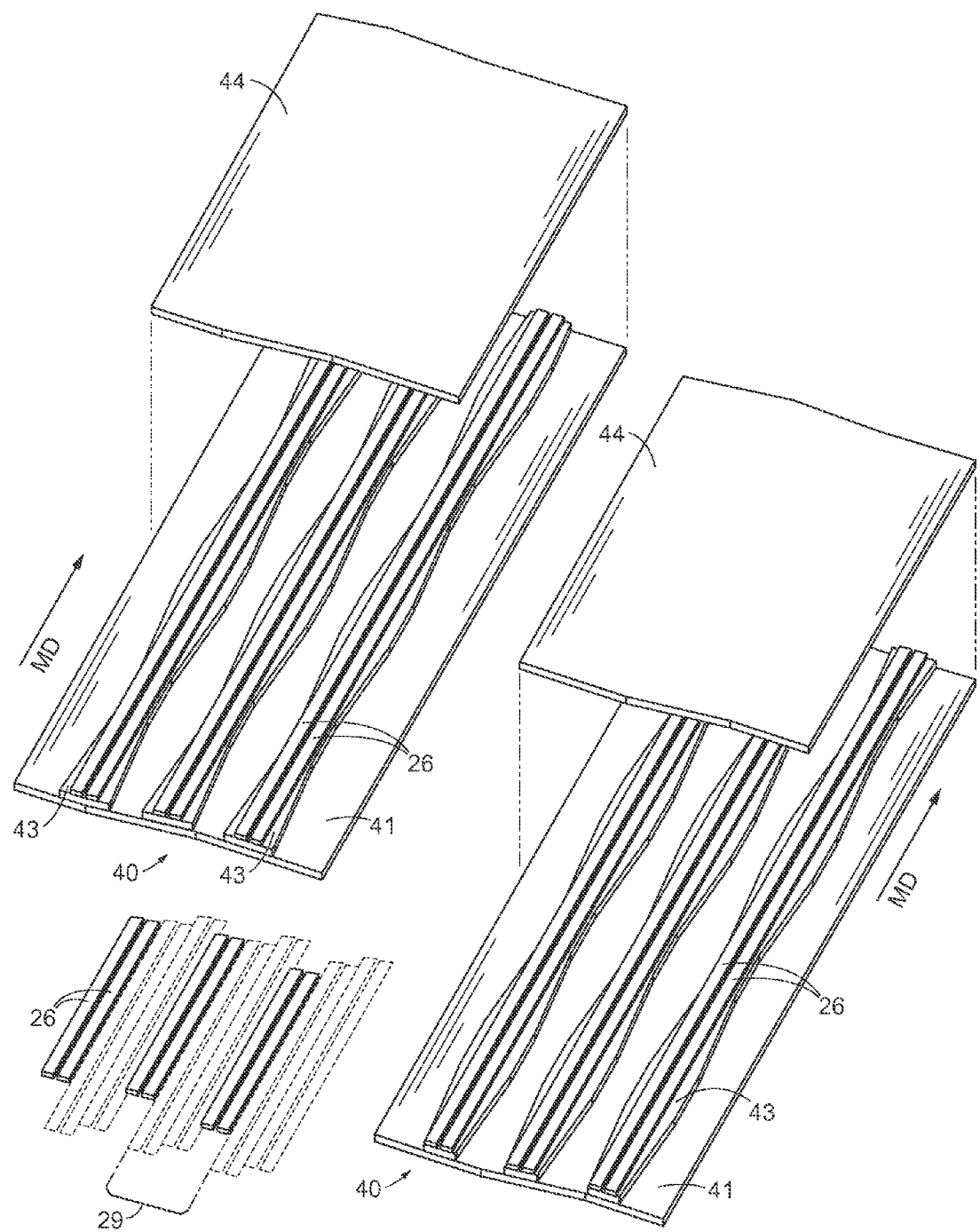
Figure 9D:
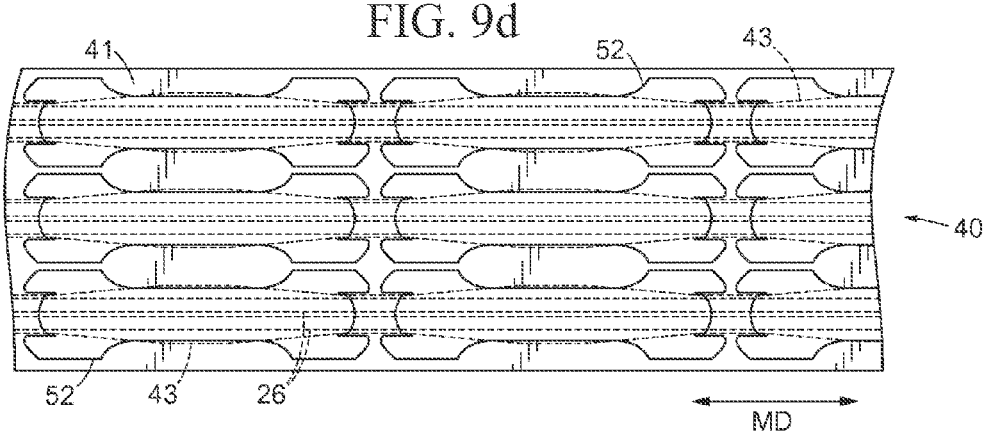
FIGS. 9d-9e are fragmentary plan views illustrating the final steps of the second form of manufacturing method.
Figure 9E:
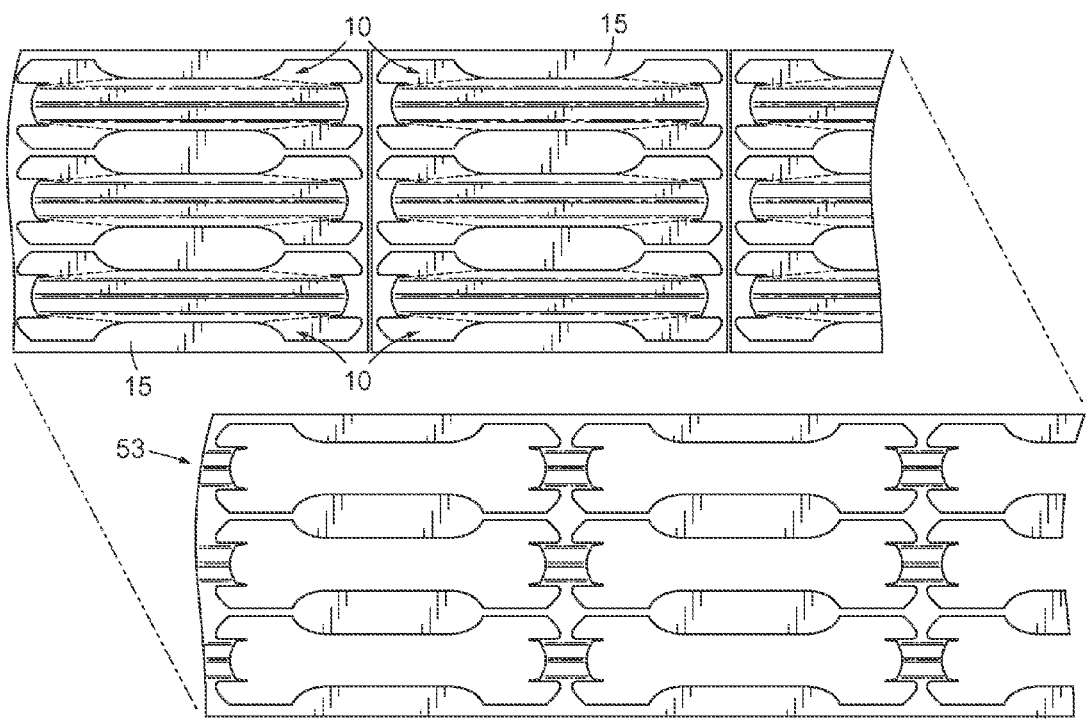
Figure 10:
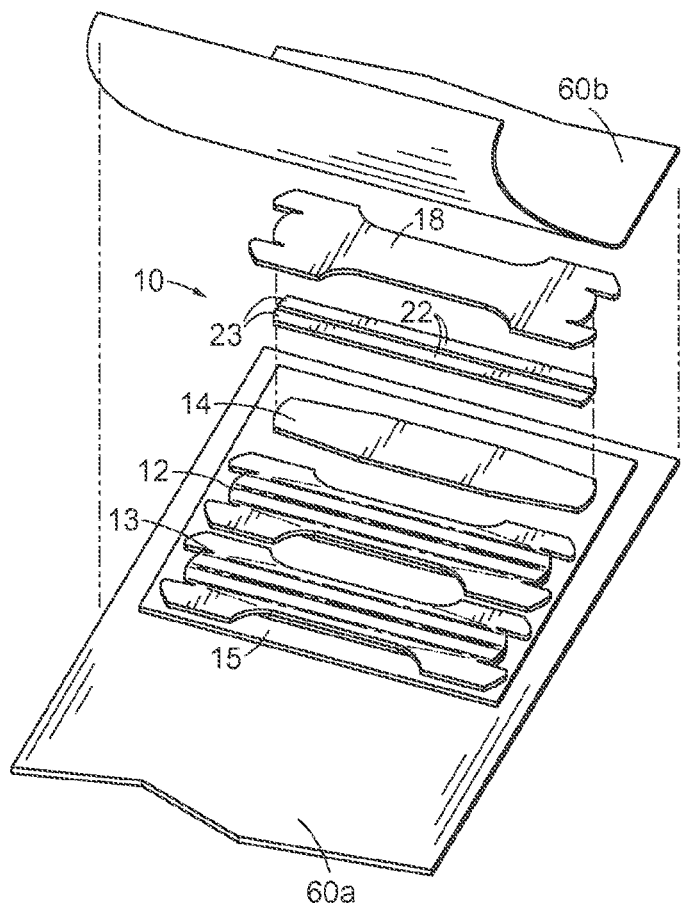
FIG. 10 is an exploded perspective view of a second form of nasal dilator embodying features of the present invention, produced from the second form of manufacturing method.

FIGS. 9*a*-9*e* illustrate a second form of manufacturing method, in accordance with the present invention, applicable to a variety of medical devices, but particularly suited to a dilator device as seen in FIG. 10. In FIG. 9*a* a plurality of continuous slits 45 in base layer material 42 form adjacent, laterally contiguous base layer strands, 43. Continuous slits 45 extend longitudinally along the machine direction of base layer material 42, and extend vertically to the paper liner, 42', on one side thereof. Slits 45 diverge laterally in a repeating pattern without intersecting the outside long edges or an adjacent slit 45. Slit 45 adjacent each long edge of base layer material 42 together form outside waste strand 47. Strands 43 effectively consists of a successive plurality of interconnected base members. Strands 43 are configured to form base members to design criteria suitable to the finished device, and also configured to have a predetermined collective width which facilitates alignment to a plurality of resilient layer strands.

As further seen in FIG. 9*a*, three adjacent pairs of resilient layer strands 26 form group 29. Strands 26 are slit from resilient layer film substantially as described hereinbefore, with the exception that three waste strands (not shown) are formed and discarded to create a narrow space in between the long edges of each pair of the six strands in each group 29. The resilient layer film preferably has an adhesive substance disposed on one side, and thus strands 26 are laminated to one side of base layer strands 43. The width of strand 26 is configured so as to have suitable spring biasing properties when cut to finished length, and also configured so that group 29 has a collective width such that one pair of resilient layer strands 26 from each group 29 align to the longitudinal centerlines of every other base layer strand 43.

Configuring elongated strands to different widths and from separate material webs to meet required device design criteria, then aligning the strands to each other, may require adjustments to the alignment process. In this instance, FIG. 9*a* shows that only one pair of strands 26 at a time, from each group 29, align to respective centerlines of base layer strands 43. Groups 29, collectively, as a unit, must then be shifted laterally so that the second of three pairs of strands 26 align to the longitudinal centerlines of the remaining base layer strands 43, as more clearly seen in FIG. 9*b*. The second of pairs of strands 26 are combined thereon as just described. The third, leftover, three pairs of strands 26 may be recoiled, or may follow the previous strands onto the base layer material, or may be combined with a subsequent base layer material web. The skilled converter will see that this 3:2 ratio of strands (three pairs of strands 26 to two adjacent strands 43), respectively, is constant regardless of the width of base layer material 42 or the total number of elongated strands.

As further seen in FIG. 9*b*, every other base layer strand 43, including the pair of resilient layer strands 26 aligned thereon, is separated from paper liner 42', as indicated by broken lines, and layered onto a separate release paper liner 41. Both first and second sets of paired strands 26 from groups 29 may be aligned to base layer strands 43 before separating combined strands onto paper liner 41, as described, or alternatively, the first set of paired strands 26 may be combined with strands 43 and removed onto paper liner 41 before proceeding to the second set. Regardless, all of the combined strands 26 and 43 maintain lateral spacing therebetween.

The preceding steps apply whether or not base layer material 42 includes an adhesive layer thereon, covered by paper liner 42'. In the event base layer material 42 does not include adhesive, first and second sets of resilient layer strands 26 may be laminated to base layer material 42 before forming base layer strands 43 (it being understood that the cutting knife height be sufficient to accommodate the thickness of strands 26). Strands 26 will inhibit any inadvertent stretching of the base layer strands 43 as combined strands 26 and 43 are removed onto separate release paper liner 41. In the event base layer material 42 includes an adhesive layer, slits 45 may alternatively extend through paper liner 42', in which case each base layer strand 43 would have the paper liner portion removed as the combined strands 26 and 43 are layered onto separate paper liner 41.

Concurrent with separating combined strands 26 and 43 onto separate release paper liner 41, FIG. 9*c*, shows two webs of elongated cover layer material 44 laminated by their adhesive sides to exposed surfaces of resilient layer strands 26, base layer strands 43 and paper liners 41 and 42' to form two material laminates 40. At this point, paper liner 42' is effectively the same as separate release paper liner 41, and for simplicity is referenced accordingly in the drawing. Combined resilient layer strands 26 and base layer strands 43 are effectively divided onto separate paper liners, positioned in a spaced apart relationship. That spacing is determined by the configuration of base layer strands 43 and the width of group 29. Each laminate 40 thus comprises release paper liner 41, base layer strands 43, resilient layer strands 26, and cover layer material 44. Paper liner 41 is the foundation of laminate 40, providing the surface against which dilators 10 are kiss cut, as illustrated in FIGS. 9*d* and 9*e*.

Base layer material 42 generally carries a lower cost per unit of measure than the resilient layer film, but a greater cost than cover layer material 44. While it is often expedient to form the base and cover layer members simultaneously to the same periphery, the present method forms and separates base layer strands 43 to create a partial base layer in the finished device, and thus extending the yield of base layer material 42. The technique doubles the number of base layer members per unit of material, with only a modest increase in converting time to separate base layer strands onto paper liners 41.

Returning now to FIG. 9d, enclosed die cut lines 52 extend vertically through material laminate 40 to, but not through, release paper liner 41 at prescribed intervals to form rows of successive finished dilator units. Die cut lines 52 are preferably aligned laterally to the centerlines of base layer strands 43 and aligned longitudinally to the wider portions thereof, so that said wider portions correspond substantially to the intermediate region of finished dilator units.

FIG. 9e shows continuous waste matrix 53 removed from around and between die cut lines 52, leaving a plurality of spaced apart finished dilators 10 releasably secured to release paper liner 41. Waste matrix 53 is separated as a single matrix by virtue that cover layer material 44 extends across the width of paper liner 41. Waste matrix 53 includes greater portions of cover layer material, extending around and between finished dilators, and lesser portions of base layer and resilient layer material, extending between successive finished dilators. (As noted, cover layer material 44 generally carries a lower cost than base layer and resilient layer materials.) Paper liner 41 may be bisected, as shown in FIG. 9e, or otherwise slit, perforated or scored between one or more individual dilators 10 as a means to segment dilators individually or into groups. The segments may be further encapsulated between packaging webs, 60b and 60a, as shown in FIG. 10.

FIG. 10 more particularly illustrates a plurality of finished dilators 10 releasably secured to a single release paper 15, the periphery of which extends slightly beyond their collective surface area. Dilator 10 features two parallel resilient members 22, wherein terminal end portions 23 correspond to a single protrusion 12. Base member 14 has less surface area than the cover layer, but a greater surface area than the resilient layer, and is positioned where it contributes most to device efficacy: interposed between at least the peripheral extent of resilient layer and the skin surfaces engaged by dilator 10, substantially where the device contacts the bridge of the nose. This leaves less surface area at the device end regions and a single material layer at the device tab extensions, allowing greater moisture vapor transmission from the skin surfaces thereat which contributes to user comfort.

Figure 11:
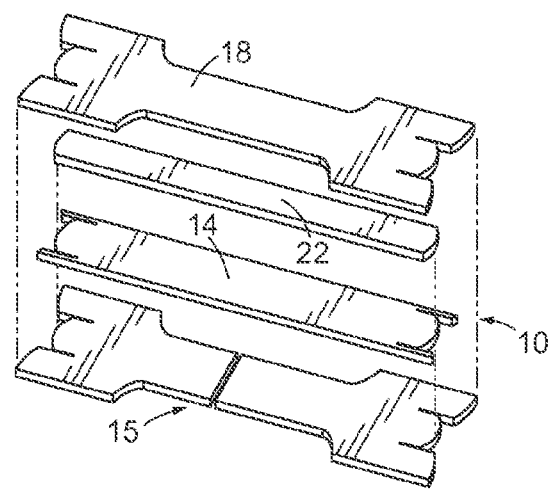
FIG. 11 is an exploded perspective view of a variation of the second form of nasal dilator produced from the method of FIGS. 12 and 13.

A dilator device shown in FIG. 11 also features a base layer having a periphery greater than the resilient layer and lesser than the cover layer. Base member 14 is interposed between at least the peripheral extent of resilient layer and the skin surfaces engaged by dilator 10, and eliminated from the tab extensions. The dilator devices of both FIGS. 10 and 11 feature substantially rectangular resilient members, having material separations 13 adjacent terminal end portions thereof, together with protrusions 12 as described hereinbefore.

Figure 12:
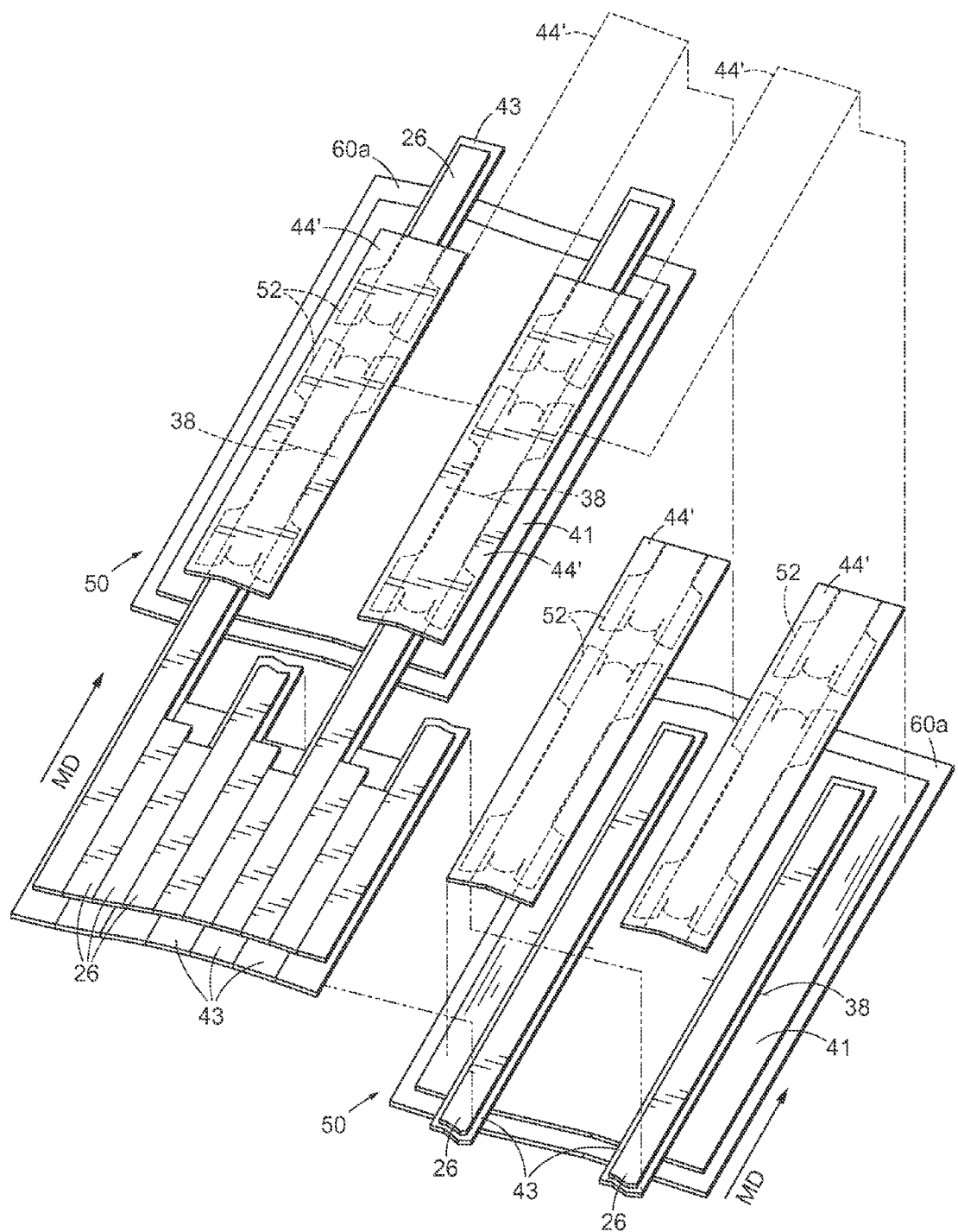
FIG. 12 is an exploded fragmentary perspective view illustrating the initial steps of a variation to the second form of manufacturing method illustrated in FIGS. 9a-9e.

FIG. 12 illustrates a variation to the second form of manufacturing method described with regard to FIGS. 9a-9e, wherein elongated strands are formed from both base layer and cover layer material webs. This variation of method is applicable to a variety of medical devices of which the dilator seen in FIG. 11 is an example. Continuous slits form laterally contiguous resilient layer strands 26 and base layer strands 43 from respective material webs as described hereinbefore. Elongated strips, 44', are slit from cover layer material 44 and may be divided by every other strip into two groups. The widths of strands 26 are configured to have suitable spring biasing properties when cut to finished length, and the widths of strands 43 and strips 44' meet design requirements for the base and cover layers of finished dilator devices. Strands 26 and 43 and strips 44' are also configured to individual and collective widths which facilitate predetermined strands and strips aligning to each other by their longitudinal centerlines.

There is a 3:2:1 ratio of three pairs of strands 26 to two adjacent strands 43 to one strip 44'. The first one of each three laterally consecutive resilient layer strands 26 align to the longitudinal centerline of each first of two laterally consecutive base layer strands 43. Broken lines indicate where every other of combined strands 26 and 43 are layered onto a separate release paper liner 41. Cover layer material strips 44' are then layered onto the combined strands 26 and 43 on each release paper liner 41, forming respective material laminates. The material laminates further include a first packaging web 60a to complete respective fabrication matrices 50. The remaining second and third out of three resilient layer strands 26 must be shifted laterally, as described hereinbefore, to re-align to the longitudinal centerlines of the remaining second of two base layer strands 43 to repeat the process.

Strips 44' are configured to encompass the width of a finished device, and dashed lines represent where die cut lines 52 extend vertically through fabrication matrices 50 to form rows of successive finished dilators. Die cut lines may extend vertically through the material laminate from either side, kiss cutting against either packaging web 60a or 60b, as dictated by the die cutting machinery. A plurality of undercut 38 is preferably formed at intervals in paper liner 41, as described hereinbefore.

Figure 13:
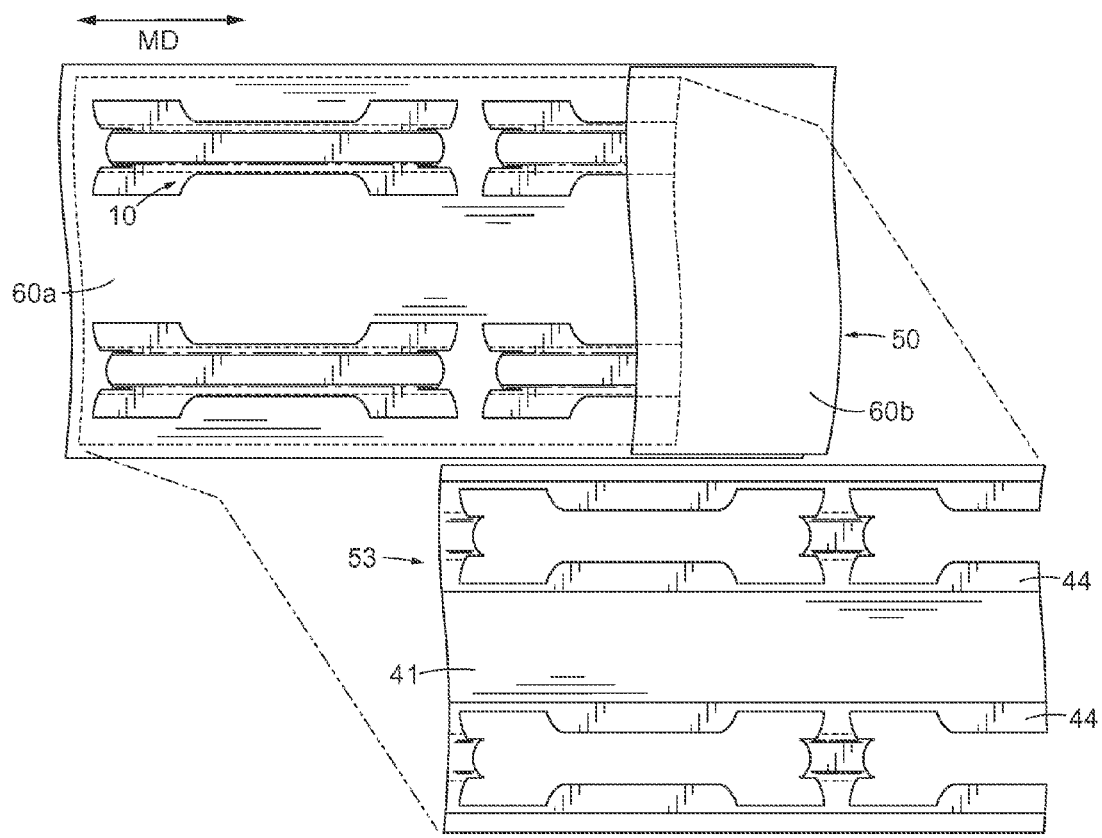
FIG. 13 is a fragmentary plan view illustrating the final steps of the variation to the second form of manufacturing method illustrated in FIG. 12.

Combining strands 26 and 43 and strips 44' by forming, separating and aligning them onto separate paper liners 41 extends material yield and creates lateral spacing between the rows finished devices so packaging material webs 60a and 60b form an adequate perimeter seal. FIG. 13 shows waste matrix 53 removed from fabrication matrix 50 (the fabrication matrices are identical, only one is shown), leaving a plurality of finished dilator units on packaging web 60a to be sealed with packaging web 60b. Waste matrix 53 consists primarily of paper, and is separated as a single matrix by virtue that release paper liner 41 extends across the width of fabrication matrix 50. The cost of paper liner 41 and packaging material webs 60a and 60b is considerably lower per unit of measure than the base, resilient and cover layer materials which form finished dilator devices.

Figure 14:
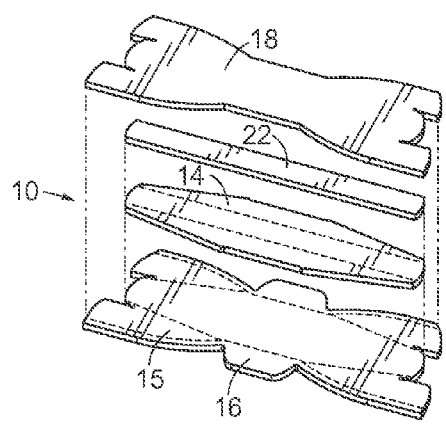
FIG. 14 is an exploded perspective view illustrating a third form of dilator device in accordance with the present invention produced from a manufacturing method described with regard to FIGS. 15a-15g.

FIG. 14 illustrates an embodiment of a third form of dilator 10 in accordance with the present invention, the fabrication of which is illustrated in FIGS. 15a-15f to follow. The device features a partial base layer and a single rectangular resilient member. The device end edges are angled inward to correspond generally to the line where the nose meets the cheek of the user. By virtue of the manufacturing method used, release paper 15 is not bisected into two parts. Instead, its width exceeds the periphery of dilator 10, providing a lip thereat together with a lateral protrusion, 16, on each side of intermediate region 36 that a user can grasp to separate dilator 10 from release paper 15 prior to use.

Figure 15A:
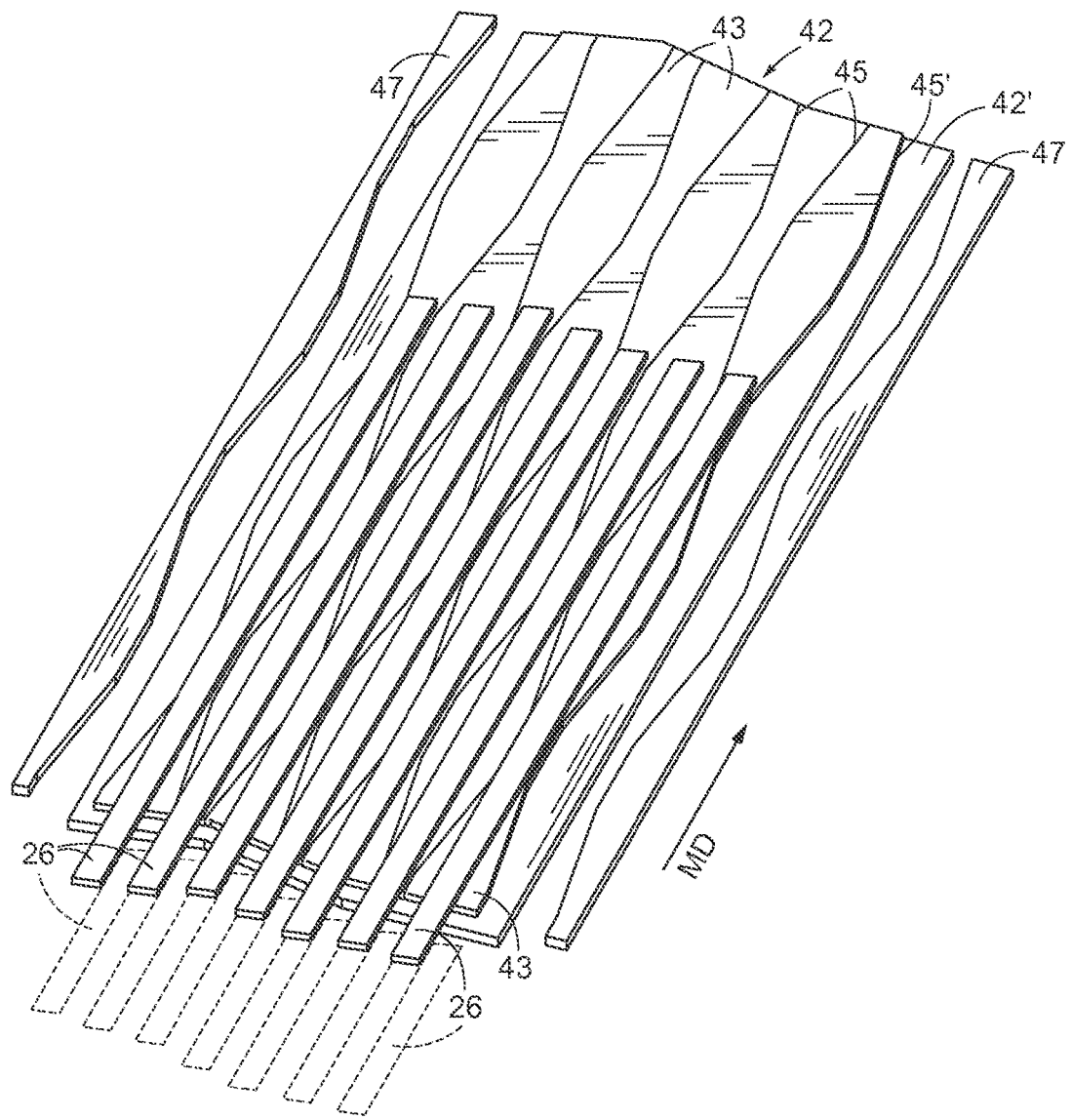
FIG. 15a is a fragmentary perspective view illustrating the initial steps of a third form of manufacturing method in accordance with the present invention whereby to manufacture the dilator of FIG. 14.

FIGS. 15a-15g illustrate a third form of manufacturing method, in accordance with the present invention, applicable to a variety of medical devices, but particularly suited to the dilator device of FIG. 14. FIG. 15a shows where continuous slits 45 form adjacent, laterally contiguous base layer strands 43 in base layer material 42 as described hereinbefore. Again, resilient layer strands 26 and base layer strands 43 are configured to meet design criteria for the device produced, and also configured to predetermined widths that allow select strands to be separated from their respective elongated material webs in a predetermined spaced apart relationship. Every other resilient layer strand 26 aligns to the longitudinal centerline of each consecutive strand 43 and is combined thereon. For illustrative clarity, outside waste strands 47 are shown separated from paper liner 42'.

Figure 15B:
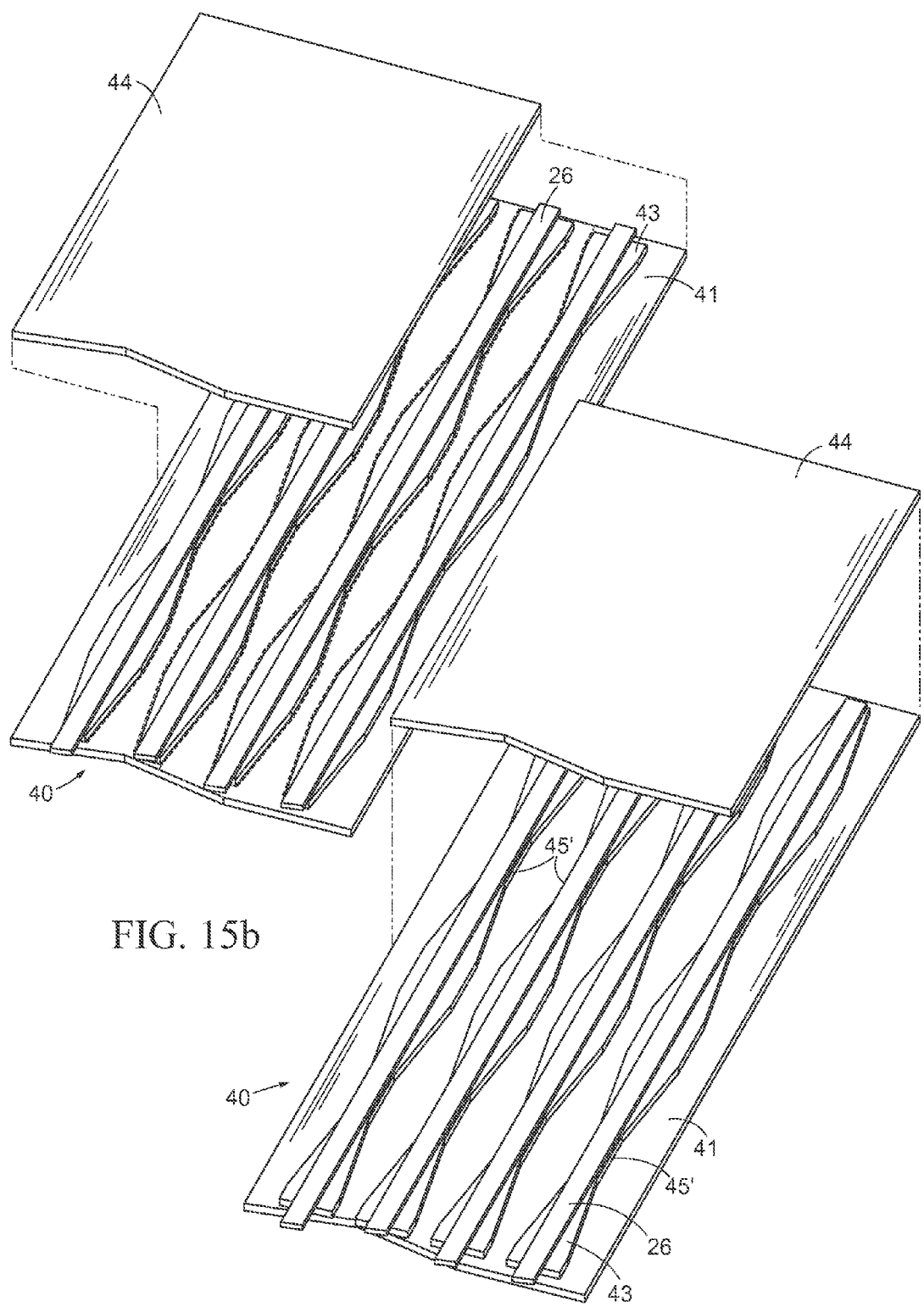
FIG. 15b is an exploded fragmentary perspective view illustrating intermediate steps of the third form of manufacturing method.

FIG. 15*b* illustrates every other of the combined resilient layer strands 26 and base layer strands 43 separated from paper liner 42' and layered onto a separate release paper liner 41. Dashed lines between remaining strands 43 represent from where every other of combined strands 26 and 43 were removed. Concurrently, two webs of cover layer material 44 are laminated by their adhesive sides to exposed surfaces of resilient layer strands 26, base layer strands 43 and paper liners 41 and 42' to form material laminates 40. As discussed previously with regard to FIGS. 9*b* and 12, the process effectively divides combined resilient layer strands 26 and base layer strands 43 onto separate paper liners. And again, absent waste strands 47, paper liner 42' is effectively the same as separate release paper liner 41, and for clarity is referenced as such in the drawing.

Figure 15C:
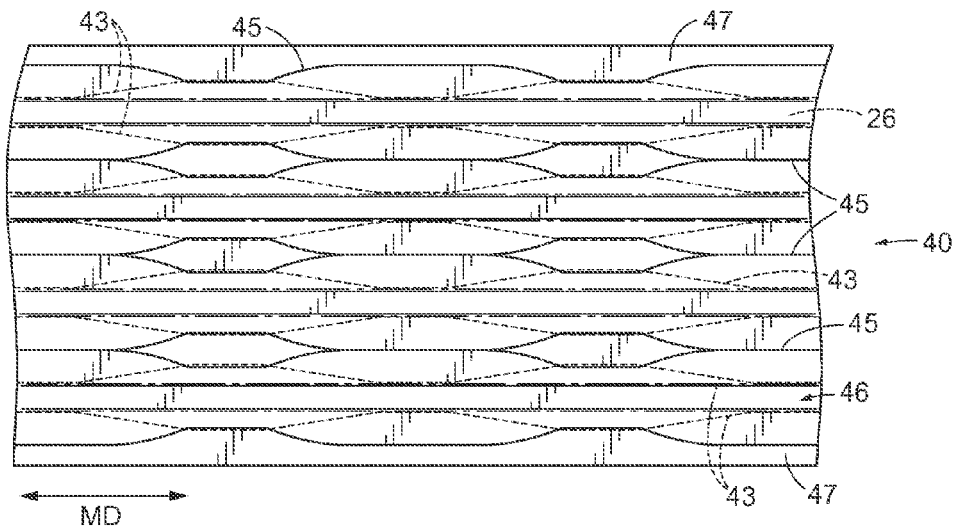
FIGS. 15c-15f are fragmentary plan views illustrating subsequent intermediate steps of the third form of manufacturing method.

As seen in FIG. 15*c*, continuous slits 45 extend longitudinally along the machine direction of laminate 40 (for simplicity, only one material laminate 40 is shown), and vertically to, but not through, release paper liner 41 to form a plurality of laterally adjacent laminate strands 46. Slits 45 diverge laterally so as to form portions of the long edges of strands 46 on a common line. Portions of slits 45 also extend along the wider portions of base layer strands 43. Slit 45 adjacent each outside long edge of laminate 40 together form outside waste strands 47. Laminate strands 46 are releasably secured to paper liner 41 by at least the adhesive substance disposed on one side of at least cover layer material 44. Each strand 46 includes combined base layer strand 43 and resilient layer strand 26, and a portion of cover layer material 44. Strands 46 are laterally contiguous at those portions formed on a common line.

Figure 15D:
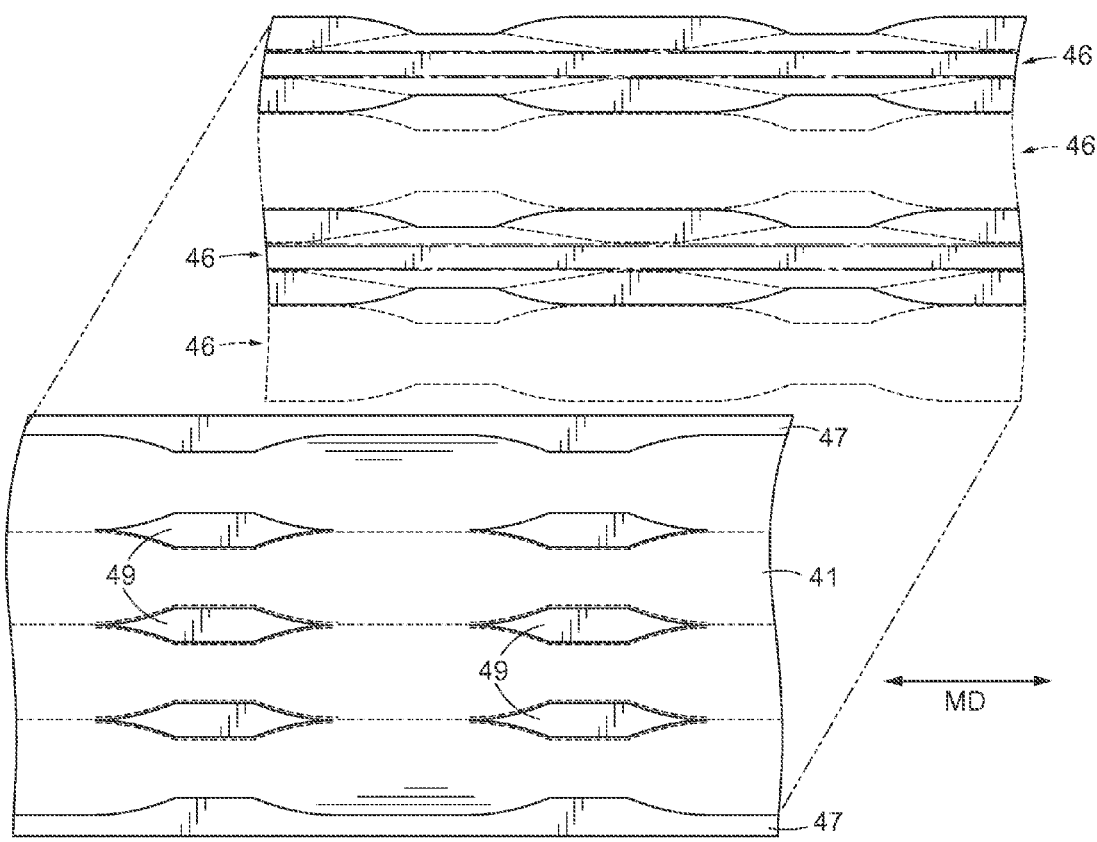

FIG. 15*d* illustrates laminate strands 46 removed from material laminate 40 leaving a waste matrix remnant thereof. For illustrative clarity, every other laminate strand 46 is represented by dashed lines, so that the configuration of laminate strand 46 is clearly seen. The waste matrix comprises a plurality of intermittent waste pieces 49 and outside waste strands 47 releasably secured to continuous release paper liner 41.

Figure 15E:
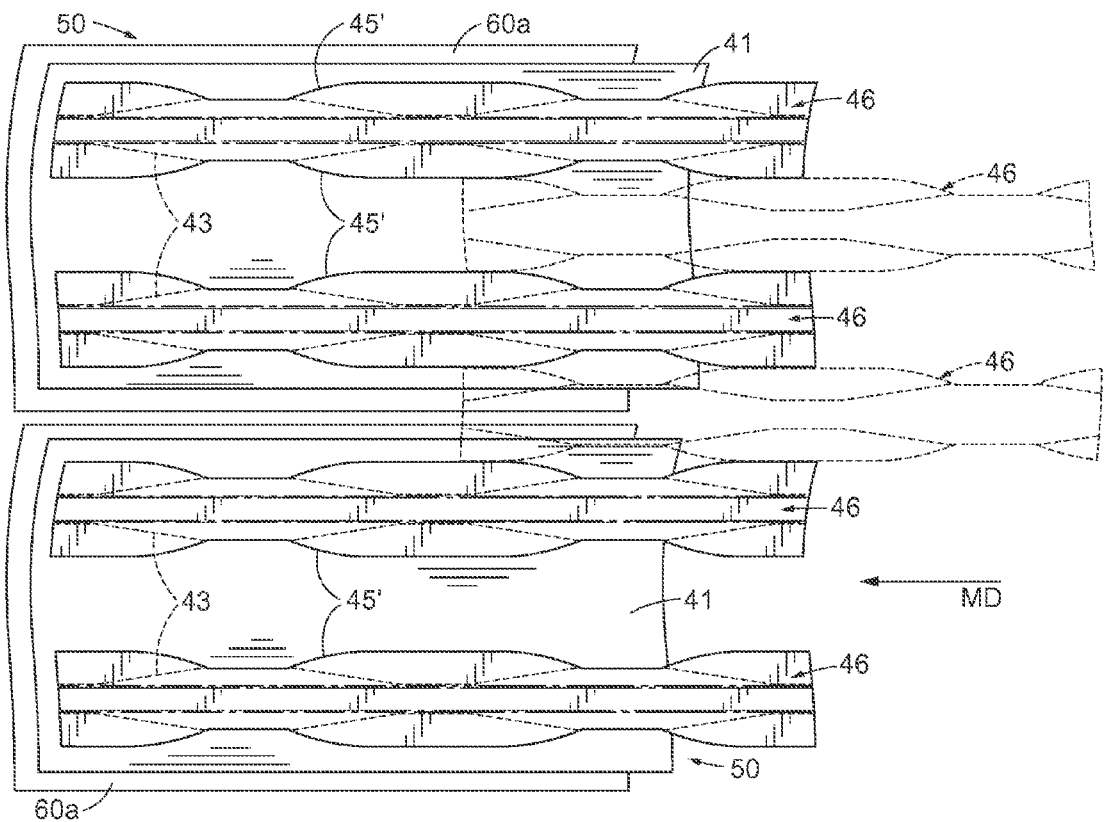

The skilled converter will again see that slits 45 could alternatively extend vertically through paper liner 41, in which case each laminate strand 46 would include a corresponding paper liner portion that would be removed prior to the next step, shown in FIG. 15*e*. The inherent tensile strength of the paper liner portion, together with the tensile strength of resilient layer strand 26, would help prevent inadvertent longitudinal stretching of the base and cover layer materials of laminate strand 46 as they are separated from laminate 40. The waste remnant of laminate 40 would then comprise outside waste strands 47 and a plurality of individual waste pieces 49, rather than the continuous waste matrix shown.

The disposition of paper liner material notwithstanding, FIG. 15*e* shows every other strand 46 layered onto additional separate release paper liners 41. A plurality of laminate strands 46 are divided and distributed onto a plurality of paper liners 41, laterally spaced apart by a distance equal to the width of a strand 46 therebetween, as represented by dashed lines. This technique extends cover layer material yield in the same manner as in extending the base layer and resilient layer materials discussed previously. FIG. 15*e* further illustrates that each combination of strands 46 and paper liner 41 are layered onto packaging material web 60*a* to form fabrication matrix 50.

Figure 15F:
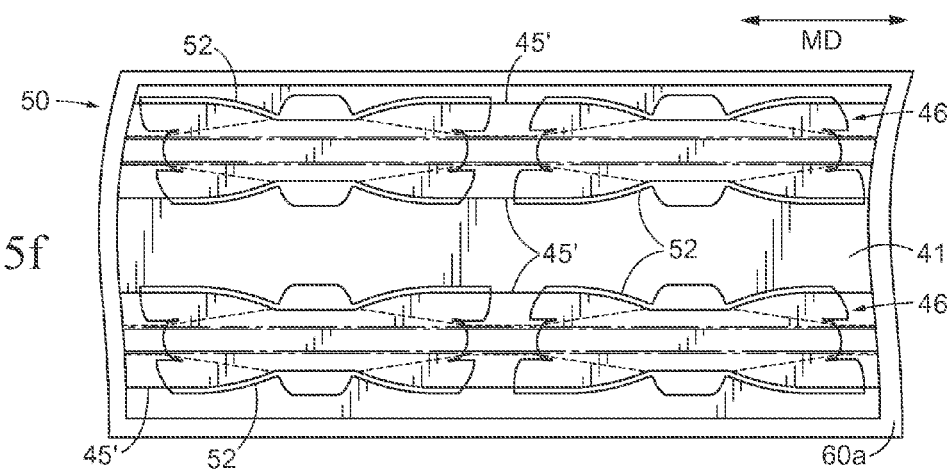

FIG. 15*f* shows that die cut lines 52 kiss cut vertically through fabrication matrix 50 to packaging web 60*a*. The long edges of die cut lines 52 extend vertically through release paper liner 41, outboard and adjacent long edges 45' of laminate strand 46. The lateral portions of die cut lines 52 bisect laminate strand 46 between long edges 45'. Thus edges 45' of laminate strand 46 come to define the long edges of successive finished dilator units, while die cut lines 52 form end edges 33 thereof and the long edges and outside corners of release papers 15 which correspond to each finished dilator 10.

Figure 15G:
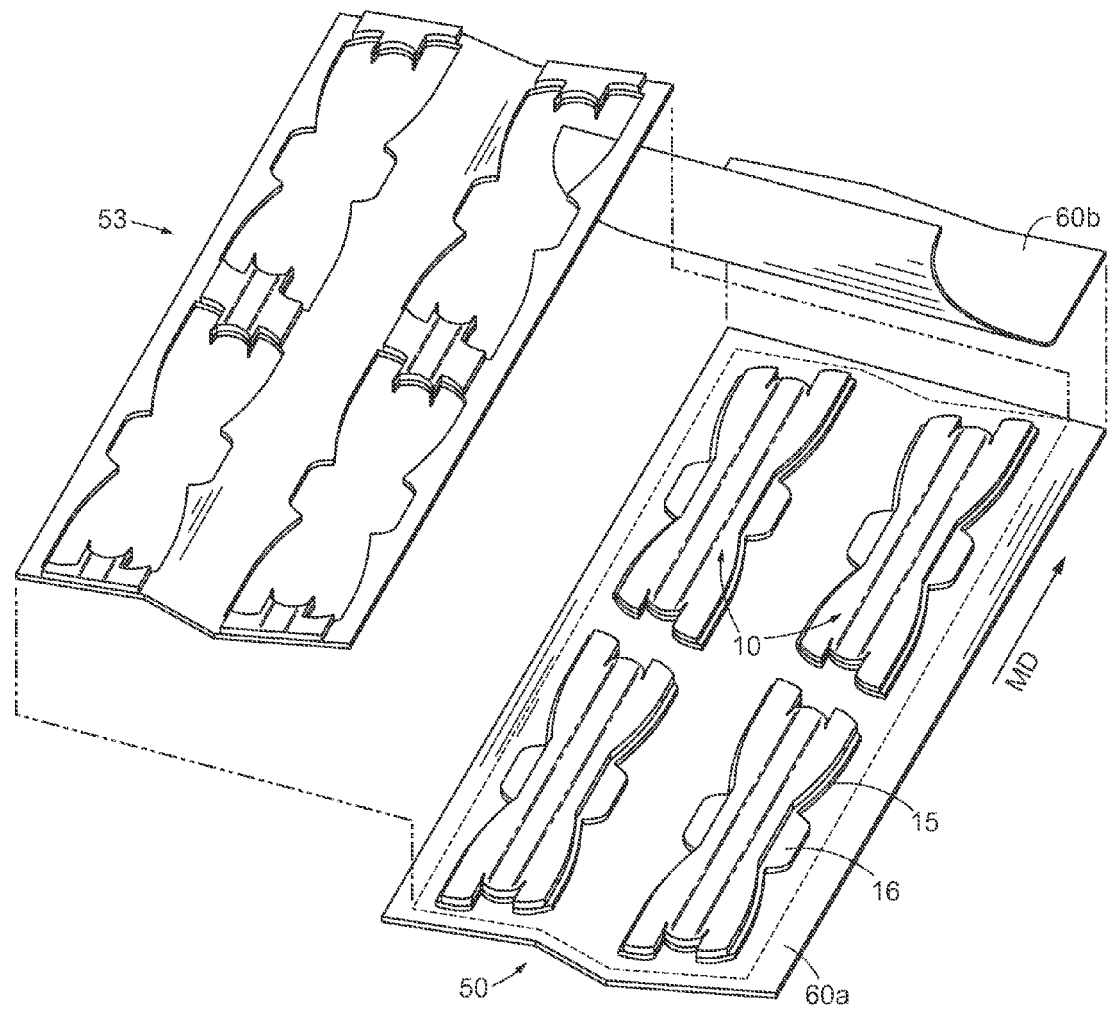
FIG. 15g is an exploded fragmentary perspective view illustrating the final steps of the third form of manufacturing method.

To complete the process, FIG. 15*g* shows continuous waste matrix 53 separated from fabrication matrix 50, leaving a plurality of spaced apart finished dilators on packaging web 60*a*. Waste matrix 53 includes paper liner 41 and sections of laminate strands 46 from around and between successive dilators 10. Again, waste matrix 53 consists almost entirely of low-cost paper, separated as a single matrix by virtue that release paper liner 41 extends across the width of fabrication matrix 50 (as more clearly seen in FIG. 15*e*). Packaging webs 60*a* and 60*b* encapsulate finished dilators 10 therebetween, as described hereinbefore.

Figure 16:
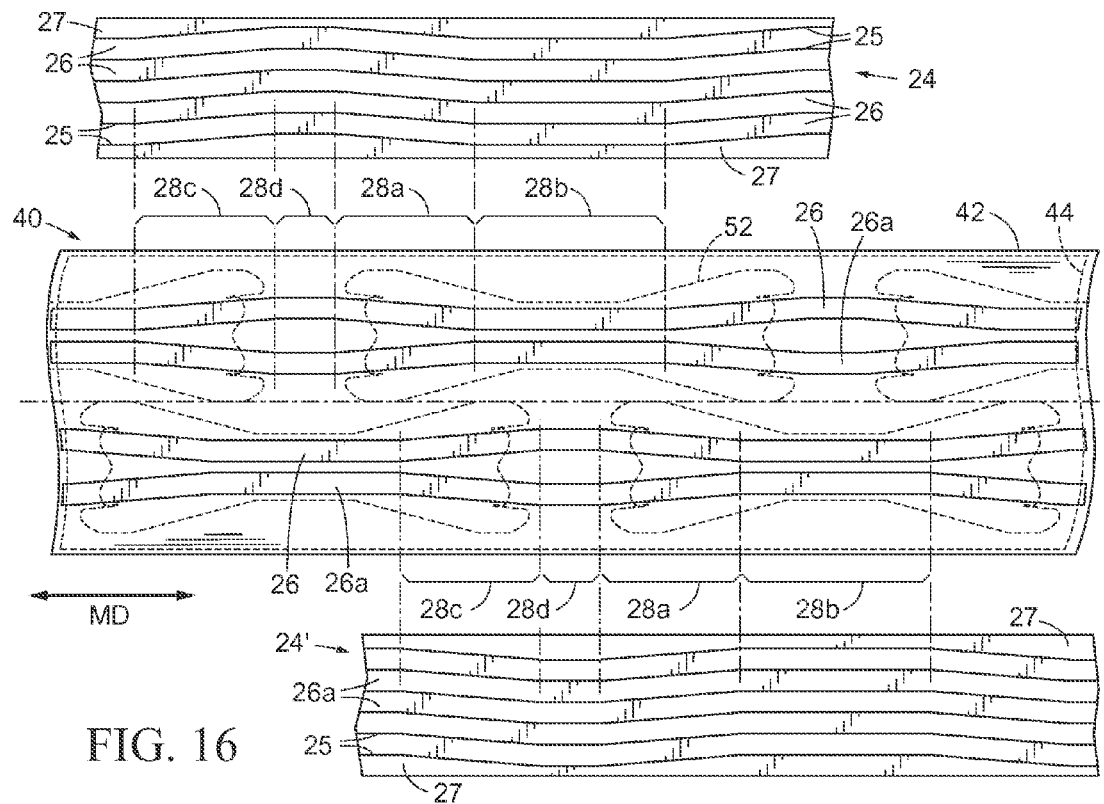
FIG. 16 is a fragmentary plan view illustrating an overview of a fourth form of manufacturing method in accordance with the present invention.

FIGS. 16 and 17*a*-17*d* illustrate a fourth form of manufacturing method and a fourth form of dilator 10 in accordance with the present invention. By way of an overview, FIG. 16 shows a plurality of resilient layer strands 26 and 26*a* formed on common longitudinal lines by slits 25 from respective webs of resilient layer film 24 and 24' (substantially as shown in FIG. 5*a*). Continuous slits 25 extend vertically through webs 24 and 24', longitudinally along the machine direction thereof, diverging laterally in a repeating pattern without intersecting the outside long edges of the resilient layer film web or an adjacent slit 25.

Strands 26 and 26*a* are formed identical, but as the mirror image of each other: in web 24 strands 26 diverge to one side, in web 24' strands 26*a* diverge to the opposite side. Slit 25 adjacent each long edge of webs 24 and 24' together form an outside waste strand, 27. Slits 25 are parallel to each other and uniformly spaced, though strand widths may otherwise vary according to the desired design attributes for the medical device to be fabricated. It should also be noted that by virtue of integrating strands 26 and 26*a* from separate webs of resilient layer film 24 and 24', one material web may be of a different thickness than the other, resulting in resilient layer strands of different thickness.

FIG. 16 also shows resilient layer strands 26 and 26*a* combined with base layer material 42, which has an adhesive substance disposed on one side, covered by paper liner 42'. Strands 26 and 26*a* are taken as pairs from respective webs 24 and 24' and combined with base layer material 42 so as to be in a predetermined, laterally spaced arrangement, the technique for doing so illustrated in FIG. 17*a*. Cover layer material 44, shown in dashed lines, having substantially the same width as material 42, is laminated by its adhesive side on top thereof to complete material laminate 40. Enclosed die cut lines 52, represented by dashed lines, show where finished dilator units will be die cut.

As discussed hereinbefore. resilient layer strands 26 and 26*a* consist of a plurality of resilient members integrated into an elongated strand. In the present embodiment, strands 26 and 26*a* have segments, 28*a*, 28*b*, 28*c*, 28*d*, as indicated by broken lines and brackets, which repeat in a continuous pattern. Segments 28*a* and 28*c* correspond generally to end regions 32 and 34 of the truss, diverging from segments 28*b* and 28*d*. Segment 28*b* corresponds generally to intermediate region 36. Segment 28d interconnects successive resilient members and also sets the spacing, at least in part, between successive die cut lines 52.

As further seen in FIG. 16, enclosed die cut lines 52 form rows of successive dilators 10, each row registered laterally with paired resilient layer strands 26 and 26a. Die cut lines 52 are longitudinally positioned along segments 28a, 28b and 28c. Alternating pairs of strands 26 and 26a are longitudinally staggered so that the long edges of adjacent rows of dilator peripheries have substantially even spacing therebetween. That spacing serves an intended purpose, as will become apparent in subsequent steps. The widest portions of die cut lines 52 are formed along a common imaginary line, as indicated in the drawing by a broken line.

Figure 17A:
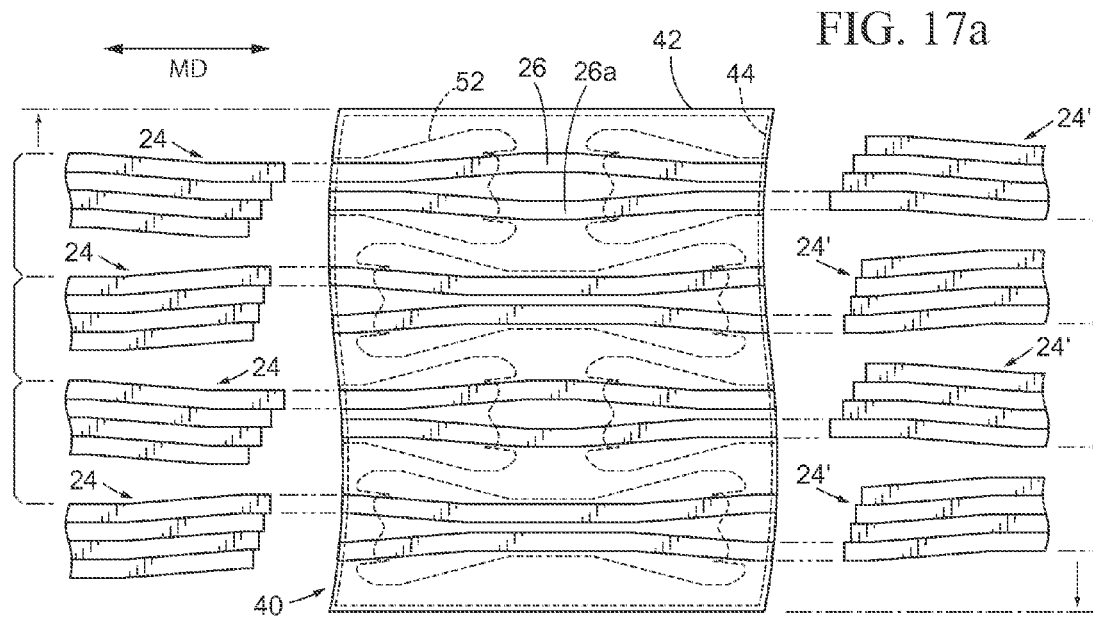
FIG. 17a is a fragmentary plan view illustrating the initial steps of the fourth form of manufacturing method.

Now to begin the fabrication process, FIG. 17a illustrates fragmentary portions of two groups of resilient layer film webs 24 and 24' (absent outside waste strands 27). The webs are aligned to other elongated webs which will form material laminate 40. While the width of each resilient layer film web is shown fragmentary, however, each web includes a plurality of adjacent, contiguous strands 26 or 26a. The webs are positioned in a staggered, overlapping relationship as indicated by brackets. The webs are aligned such that individual strands 26 and 26a are peeled from their respective webs and combined with base layer material 42 in the spaced apart arrangement illustrated in FIG. 16. For illustrative clarity, webs of resilient layer film 24 are shown to the left side of base layer material 42 and webs of resilient layer film 24' to the right side. In practice, the material webs would be positioned according to machine setup.

Broken lines indicate the first of each strand 26 and 26a from respective webs of resilient layer film 24 and 24' layered onto base layer material 42. As each resilient layer strand 26 or 26a is layered onto base layer material 42, the two groups of webs 24 and 24', collectively, are shifted laterally, as indicated by directional arrows, by a distance equal to the width of one resilient layer strand, to align the next strands to the positions formerly occupied by the strands just separated. Once the desired resilient layer strands 26 and 26a are combined with base layer material 42, cover layer material 44, shown by dashed lines, is laminated by its adhesive side on top thereof to complete material laminate 40.

Figure 17B:
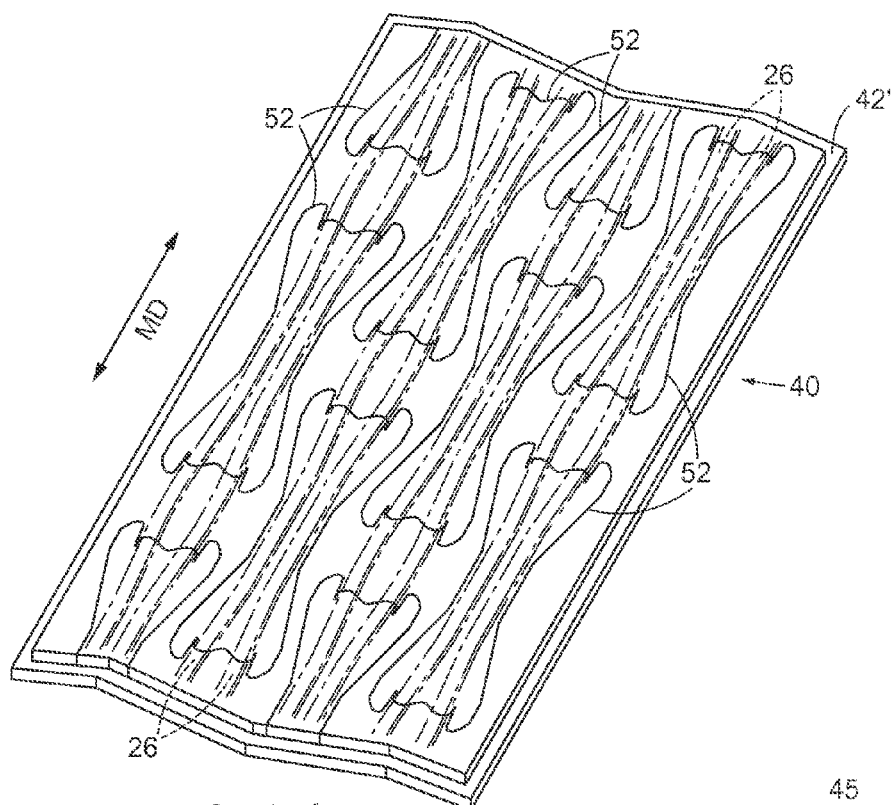
FIG. 17b-17d are fragmentary perspective views illustrating the intermediate and final steps of the fourth form of manufacturing method.
Figure 17C:
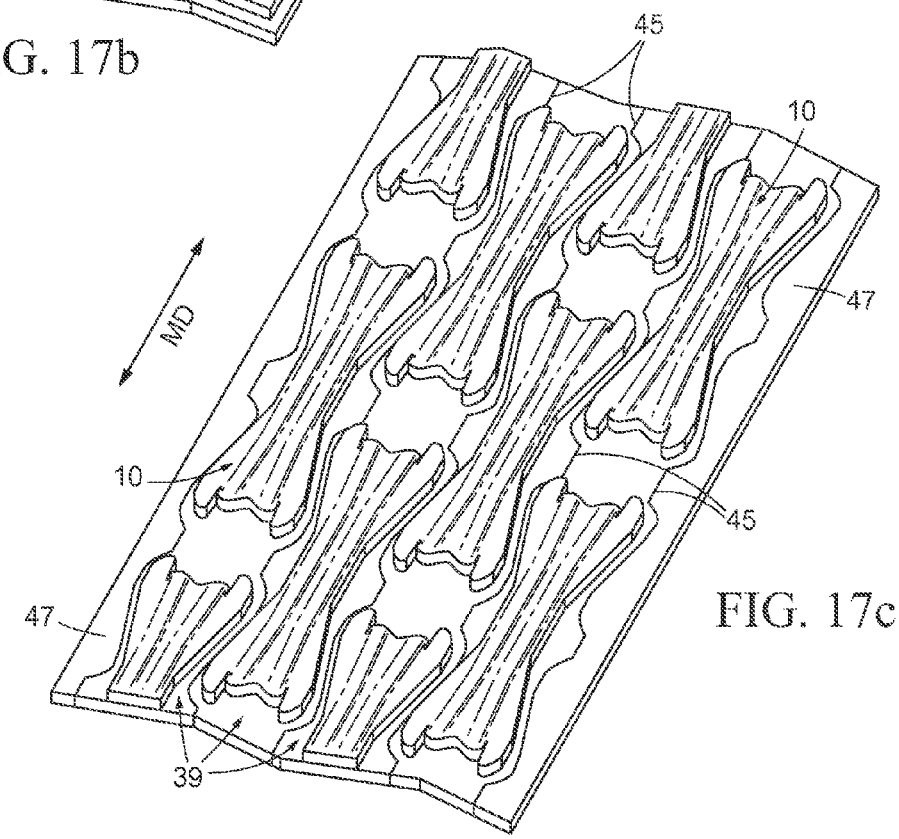

FIG. 17b shows where enclosed die cut lines 52 form of a plurality of dilator units, defining the peripheries thereof at staggered, spaced apart intervals, as illustrated in FIG. 16. Die cut lines 52 extend vertically to, but not through, paper liner 42' on the underside of base layer material 42 of laminate 40. (Paper liner 42' is shown slightly enlarged in the drawing for clarity.) The waste material matrix extending around and between die cut lines 52 is removed, leaving a plurality of finished spaced apart dilators 10 releasably secured to paper liner 42', as illustrated in FIG. 17c.

At this point in the process, a plurality of finished dilator devices are effectively captured in bulk on a contiguous paper liner. That may be adequate for many medical device applications. However, to segment finished devices, FIG. 17c further illustrates continuous slits 45 extending vertically through paper liner 42' and longitudinally along the machine direction thereof. Slit 45 is formed in the spaces between the long edges of laterally adjacent dilators 10. Slit 45 does not intersect a finished dilator, or the outside long edges of paper liner 42' or an adjacent slit 45. Slits 45 may extend between finished dilators in any configuration, however, to seal finished devices between packaging material webs, slits 45 divide paper liner 42' into a plurality of an elongated finished strand, 39. Each strand 39 has rows of successive finished dilators 10 releasably secured thereon. Each slit 45 thus forms opposing long edges 45' of two laterally adjacent finished strands 39. Slit 45 adjacent each outside long edge of paper liner 42' defines one long edge of strand 39, and together with each outside long edge of paper liner 42' forms outside waste strands 47.

Figure 17D:
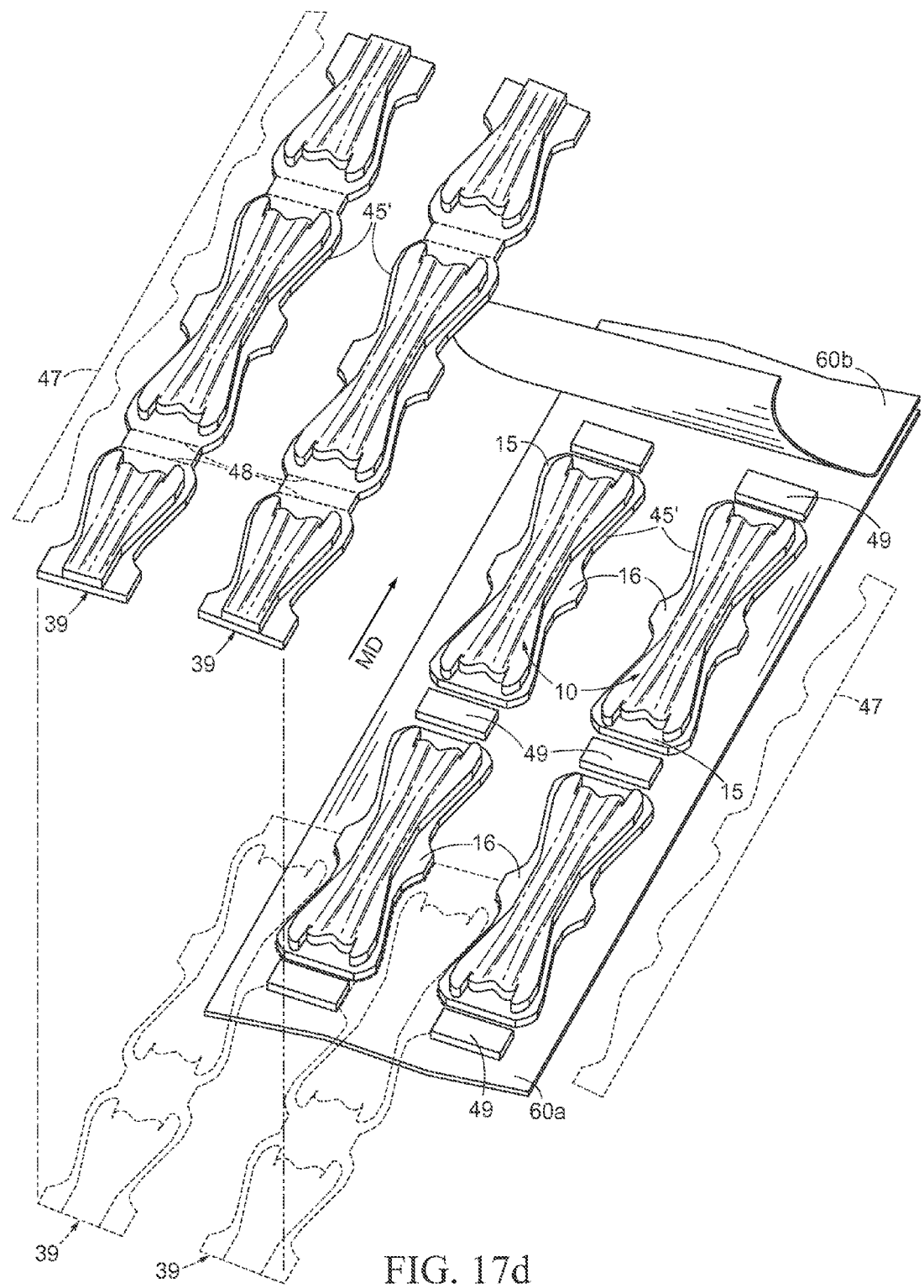

To package finished devices, FIG. 17d shows finished strands 39 separated onto one or more packaging material webs 60a. Strands 39 maintain lateral spacing equal to the width of the strand 39 formerly therebetween, as represented by dashed lines. Cross slits 48 extend laterally between long edges 45' and vertically to, but not through, packaging web 60a, bisecting the release paper liner of strand 39 into sections with waste pieces 49 therebetween. Thus substantial portions of long edges 45' of strand 39 define the long edges of successive release papers 15 corresponding to successive dilators 10.

The peripheral edges of release paper 15 are outbound the periphery of each dilator 10, providing a lip thereat and a lateral protrusion 16 on each side of intermediate region 36 that a user may grasp to separate dilator 10 therefrom. Waste pieces 49 (shown slightly separated for illustrative clarity) are removed from the surface of packaging web 60a in between dilators 10 by any suitable means such as suction or targeted forced air. Packaging web 60b then forms a seal with packaging web 60a around and between dilators 10 as described hereinbefore.

Figure 18:
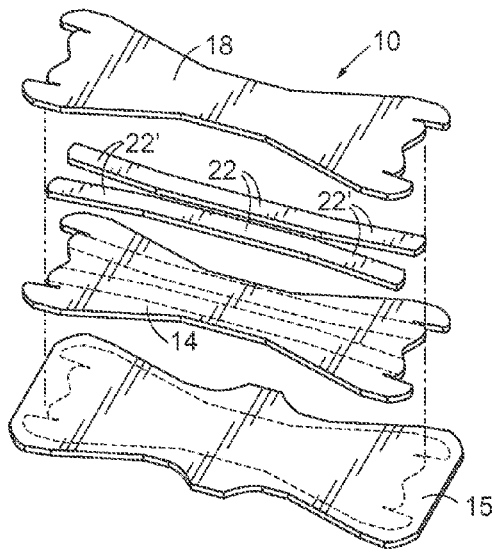
FIG. 18 is an exploded perspective view of a fourth form of nasal dilator in accordance with the present invention, produced from the method of FIGS. 16-17d.
Figure 19:
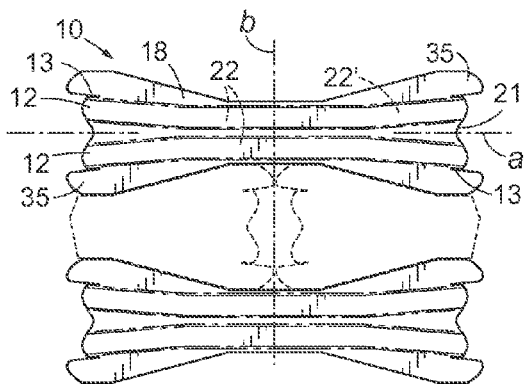
FIG. 19 is a plan view of the nasal dilator of FIG. 18.

FIGS. 18 and 19 more particularly illustrate the finished device. FIG. 18 shows adjacent resilient members 22 each having divergent components, 22', extending laterally from a rectangular mid section. Resilient member components 22' constitute a directional element, spreading spring biasing forces to a greater lateral surface area of the device end regions. A component 22' may be shorter, longer, of different width, gradient, curved, etc., and may be configured differently in each end region.

As more clearly seen in FIG. 19, dilator 10 is symmetric on both sides of its lateral centerline, b, and symmetric on both sides of its longitudinal centerline a. A material separation, valley 21, extends inward from each end edge 33, interposed between resilient member terminal end portions 23. Valley 21 may be of any shape, and like material separations 13, is configured to facilitate the separation of protrusion 12 and the shifting of spring biasing peel forces to shear forces as described hereinbefore. FIG. 19 further shows by dashed lines that the peripheral shape of dilator 10 is conducive to common line die cutting, as discussed previously with regard to FIG. 4.

Figure 20:
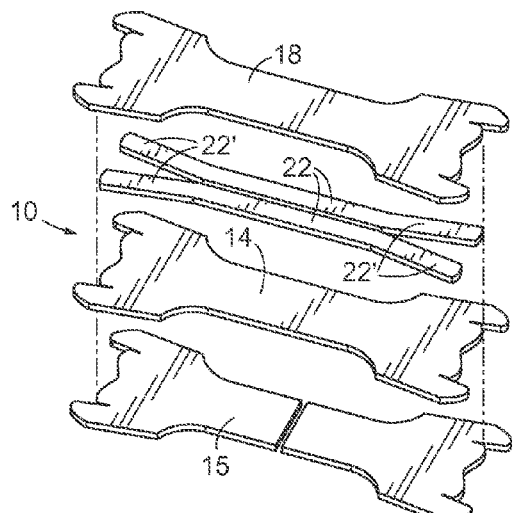
FIG. 20 is an exploded perspective view of a variation of the fourth form of nasal dilator.
Figure 22:
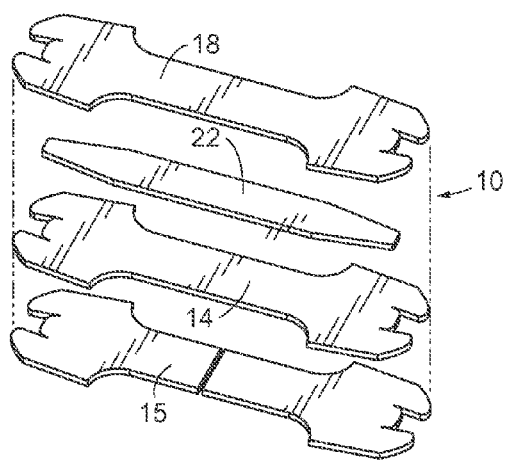
FIG. 22 is an exploded perspective view of a fifth form of nasal dilator in accordance with the present invention, produced as complementary device from the method of FIGS. 23a-23d.
Figure 21:
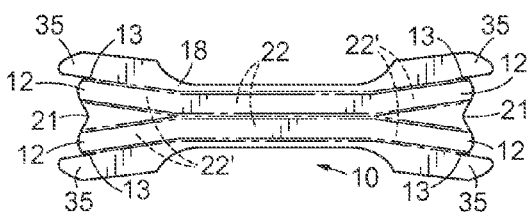
FIG. 21 is a plan view of the nasal dilator of FIG. 20.

FIGS. 20-21 and FIG. 22 illustrate two dilator devices produced from a manufacturing method described with respect to FIGS. 23a-23f to follow. The dilator of FIGS. 20 and 21 is a variation of the device of FIGS. 18-19, it's resilient members also having divergent components 22'. The dilator of FIG. 22 is a fifth form of nasal dilator 10 in accordance with the present invention, produced as a complementary device. It features a resilient member having long edges which taper from a wider rectangular portion to narrower terminal end portions, the extent of which corresponds generally to the device end regions. The tapered portions constitute a directional element, reducing the spring biasing force of the truss thereat. Base member 14 of both dilator devices is shown having the same peripheral shape as cover member 18. Alternatively, base member 14 could have the same peripheral shape as the resilient member(s).

Figure 23A:
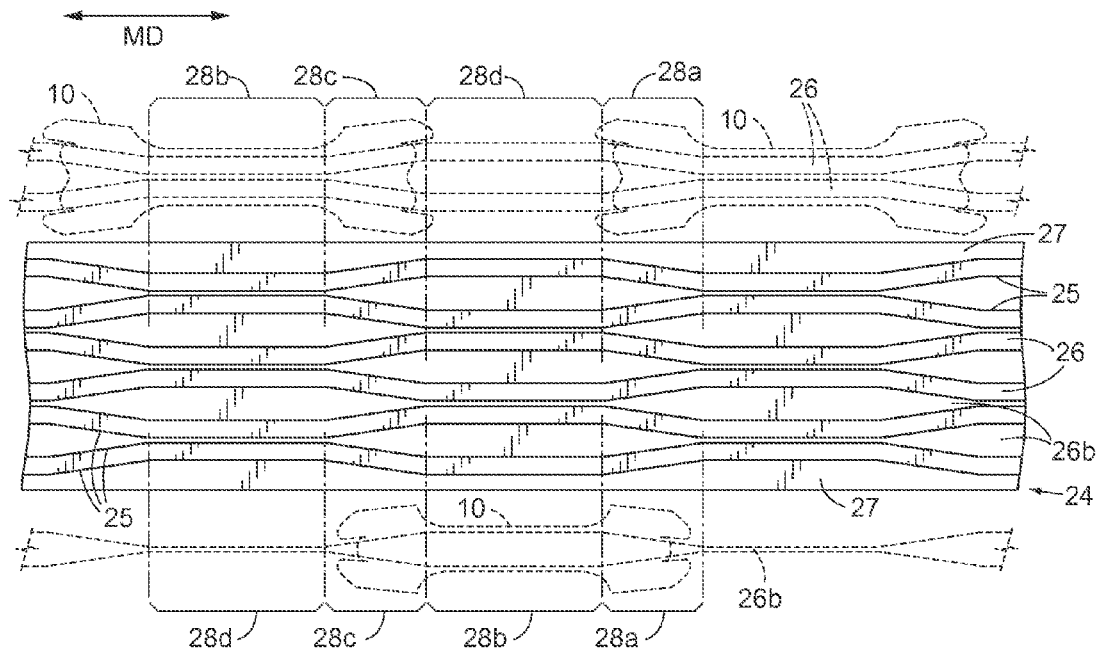
FIG. 23a is a fragmentary plan view illustrating an overview of a fifth form of manufacturing method in accordance with the present invention.

FIG. 23a illustrates an overview of a fifth form of manufacturing method, in accordance with the present invention, applicable to a variety of medical devices, but particularly suited to dilator devices like those seen in FIGS. 20-22. Slits 25 form different configurations of resilient layer strands from a web of resilient layer film 24. Resilient layer film 24 may alternatively include a base layer material laminated thereto, as described hereinbefore. Continuous slits 25 extend vertically through web 24, longitudinally along the machine direction thereof, diverging laterally in a repeating pattern without intersecting the outside long edges or an adjacent slit 25. Slit 25 adjacent each long edge of resilient layer film 24 together form outside waste strand 27.

Slits 25 are configured to form two laterally spaced apart strands 26, which may be combined in the fabrication of the dilator device represented by dashed lines at the top of FIG. 23a. To avoid waste material between opposing strands 26, a second strand, 26b, is formed therebetween. Strand 26b, which might otherwise be waste material, is instead processed into a complementary dilator device as shown by dashed lines at the bottom of FIG. 23a.

Strands 26 and 26b alternate consecutively across the width of resilient layer film 24; the configuration of one strand defines, at least in part, the configuration of the strand adjacent to it on either side. Similarly, the width of a strand defines the lateral spacing between the two strands adjacent on either side. The strands are configured so that resilient layer structures formed therefrom meet functional and directional element criteria for the dilator device produced, and to predetermined widths that allow select strands to be separated from resilient layer film 24 in a predetermined spaced apart relationship, as discussed hereinbefore.

As noted previously, resilient layer strands 26 and 26b consist of a successive plurality of resilient members integrated into an elongated strand. Broken lines and brackets in FIG. 23a indicate segments 28a, 28b, 28c, 28d which repeat in a continuous pattern. Segments 28a and 28c correspond to dilator device end regions, and segment 28b corresponds generally to the intermediate region. Segment 28d interconnects successive resilient members and also sets the spacing between successive die cut lines 52. Segments 28b and 28d are the same length, thus each consecutive resilient layer strand 26 may be viewed as either the mirror image of the previous, alternating in succession, or as identical, but longitudinally staggered. Each consecutive strand 26b is identical and longitudinally staggered from the previous.

Figure 23B:
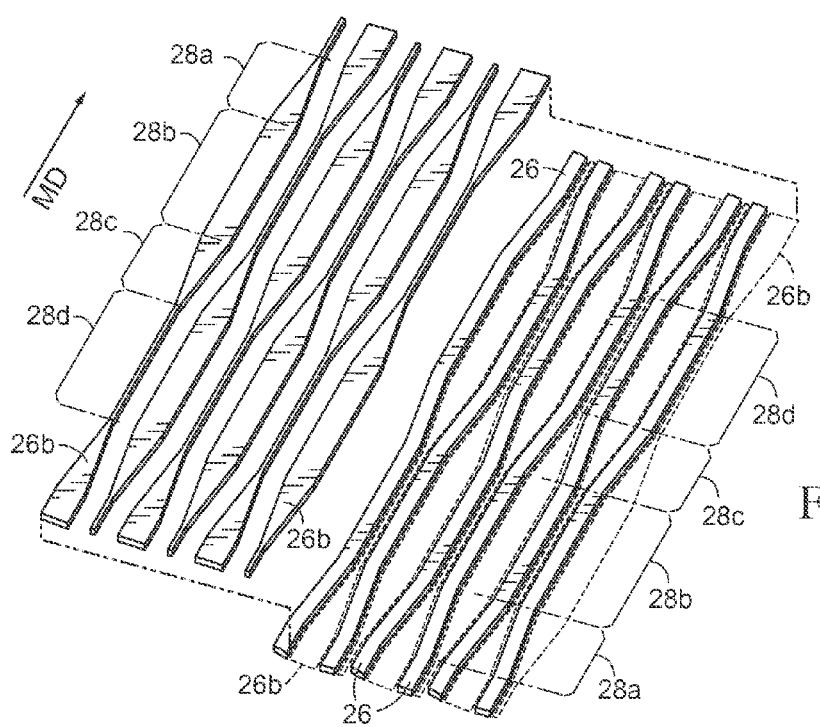
FIG. 23b is an exploded fragmentary perspective view illustrating the separation of elongated material strands into two groups as an optional initial step of the fifth form of manufacturing method.

FIG. 23b illustrates lateral spacing between resilient layer strands 26 and 26b when the strands are separated. Dashed lines represent where strands 26b formerly occupied the spaces between adjacent strands 26. Strands 26 are registered in a laterally spaced apart relationship determined by the width of strands 26b and vice versa. Separating strands into respective groups is not required for the manufacturing process; select strands 26 and 26b may be peeled from resilient layer film 24 and combined into a material laminate without first being separated into respective groups.

Figure 23C:
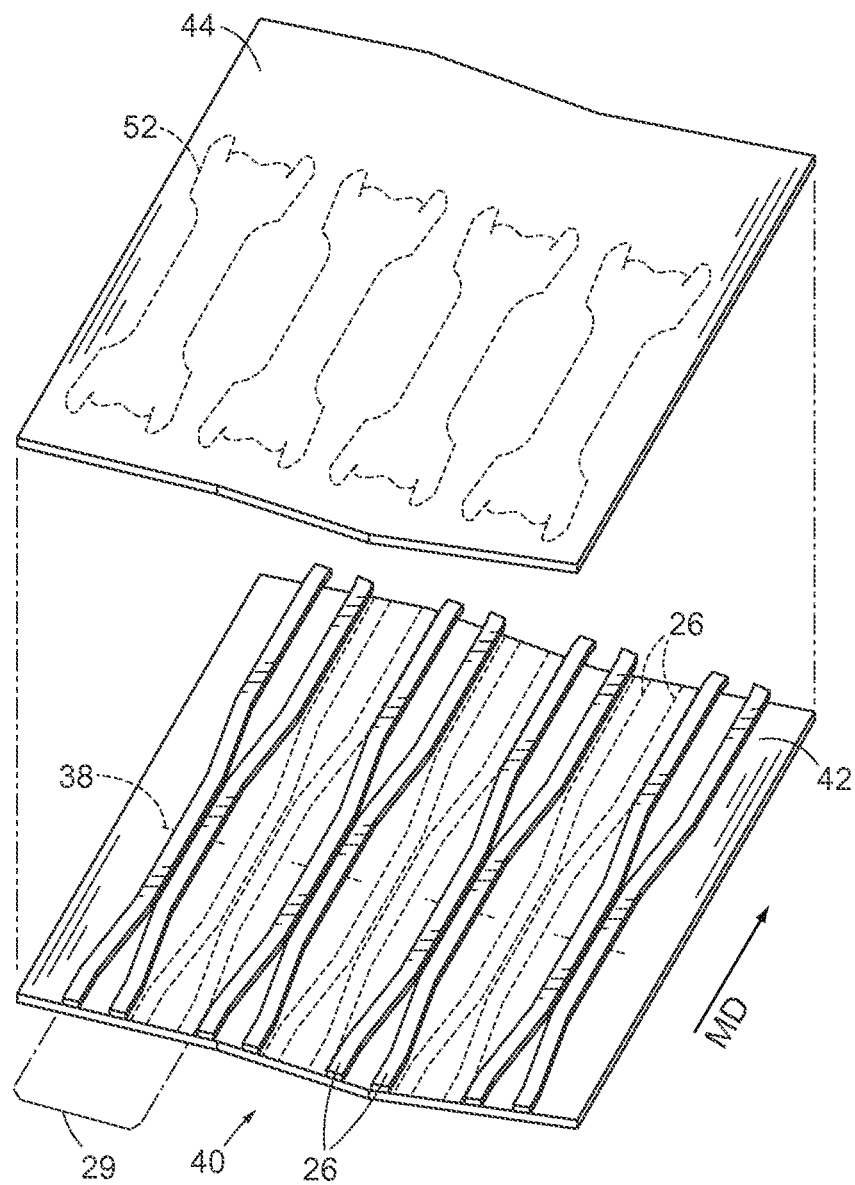
FIGS. 23c-23d are exploded fragmentary perspective views illustrating the initial steps of the fifth form of manufacturing method.

FIG. 23c shows resilient layer strands 26 combined with elongated webs of base layer material 42 and cover layer material 44 to form material laminate 40. Group 29 comprises two pairs of strands 26. One pair from each group is layered onto base layer material 42. Pairs not layered are represented by dashed lines, and may be combined into a second material laminate, or follow the first pairs of strands into the first material laminate. Cover layer material 44, preferably having substantially the same width as base layer material 42, is laminated by its adhesive side onto exposed surfaces of strands 26 and base layer material 42 to complete material laminate 40. Dashed lines represent where die cut lines 52 will form finished dilator units, as more particularly illustrated in FIG. 23f.

Figure 23D:
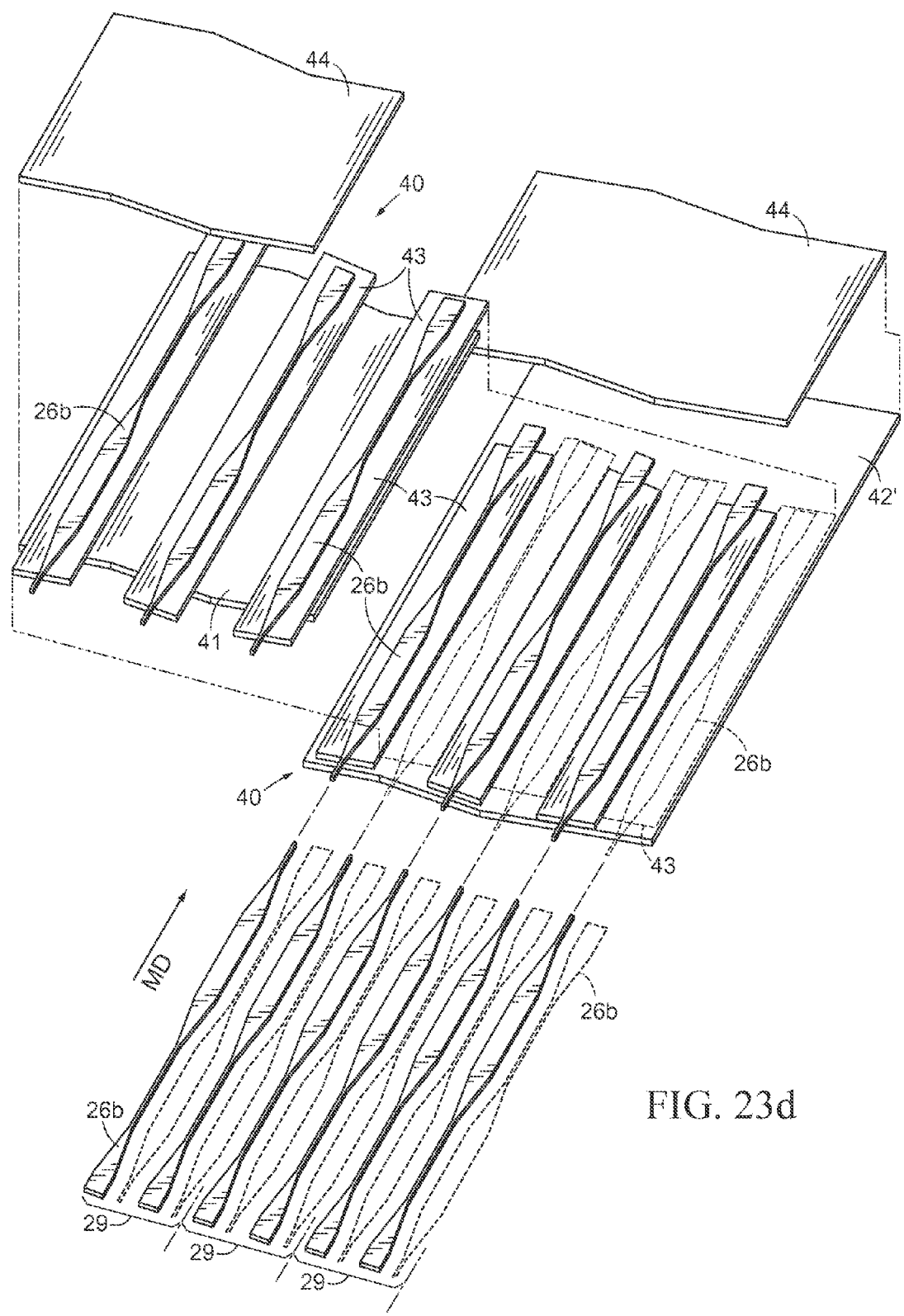

FIG. 23d shows the first and third strands 26b from each group 29 combined with laterally consecutive base layer strands 43. Base layer strands are formed in an elongated web of base layer material having an adhesive layer thereon covered by paper liner 42', as described hereinbefore. Similar to combining elongated strands shown in FIG. 12, the collective width of four laterally spaced strands 26b, which make up group 29, corresponds to the collective width of two adjacent, contiguous, base layer strands 43. The second and fourth strands 26b from each group 29, shown in dashed lines for illustrative clarity, may be recoiled for later processing, or combined with base layer and cover layer material in the same manner as the first and third strands 26b.

Broken lines indicate every other base layer strand 43, including resilient layer strand 26b aligned thereon, separated from paper liner 42' and layered onto a separate release paper liner 41. (Dashed lines illustrate the spaces formerly occupied by the separated strands.) Combined strands 26 and 43 are thus laterally spaced apart on separate release paper liners 41 and 42', respectively. Cover layer material 44, having substantially the same width as the paper liners, is laminated by its adhesive side to exposed surfaces of strands 43, strands 26 and paper liners 41 and 42', to complete each material laminate 40.

Figure 23E:
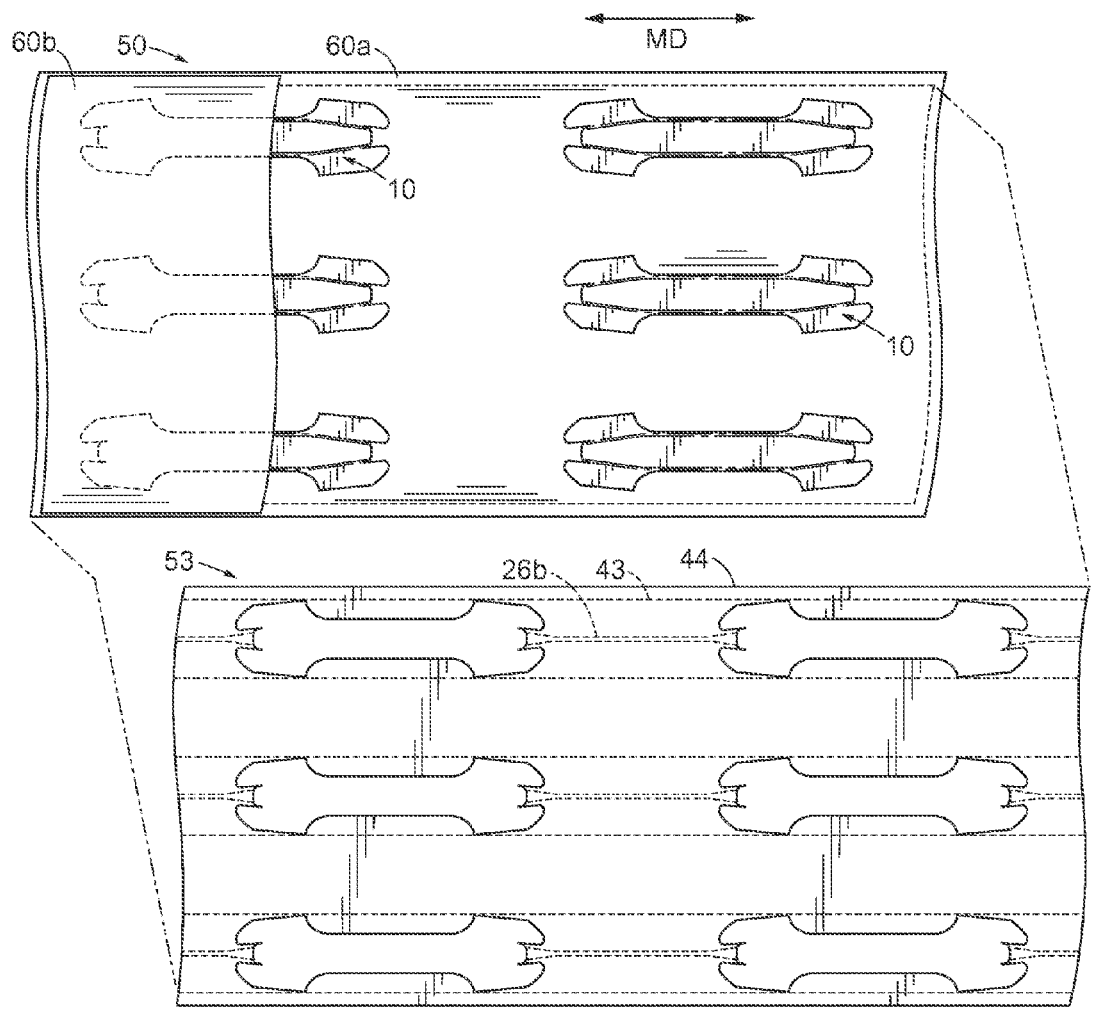
FIGS. 23e-23f are fragmentary plan views illustrating the final steps of the fifth form of manufacturing method.
Figure 23F:
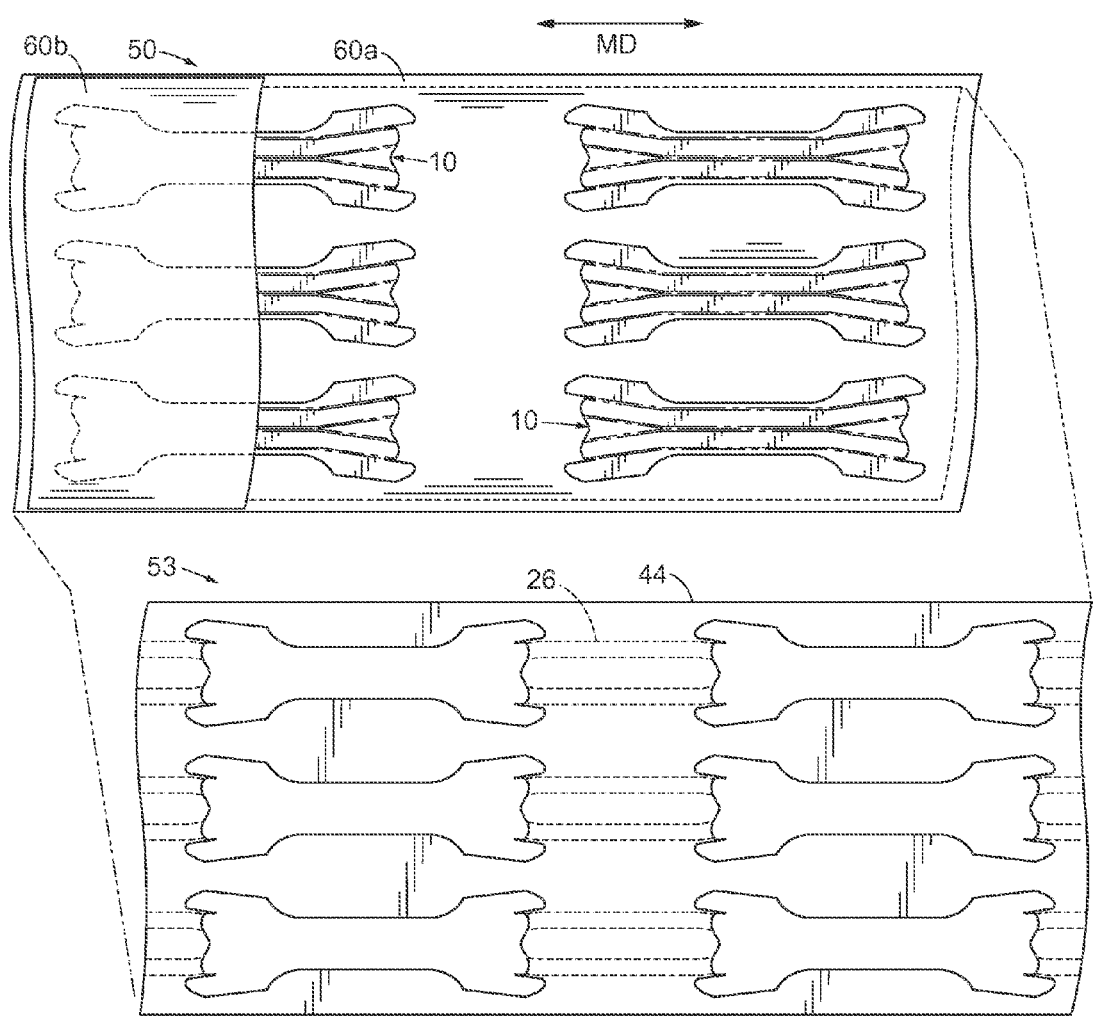

FIGS. 23e and 23f show each material laminate 40 combined with packaging material web 60a to form fabrication matrix 50. Die cut lines 52 extend through laminate 40 to packaging web 60a, forming rows of finished devices. Waste matrix 53 is removed, leaving a plurality of spaced apart finished devices such that packaging webs may form a perimeter seal between finished devices.

In FIG. 23e, waste matrix 53 includes portions of cover layer material 44 extending around die cut lines 52, and portion of base layer material strands 43 and resilient layer strands 26b extending between successive die cut lines 52. Similarly, waste matrix 53 shown in FIG. 23f includes portions of cover layer material 44 and base layer material 42 extending around die cut lines 52, and portions of strands 26 extending between successive die cut lines 52. The sealed, finished devices may be further segmented by cuts or scores extending through the packaging webs in between one or more encapsulated devices.

The preceding method forms elongated resilient layer strands 26 and 26b in equal numbers. By combining each two resilient layer strands 26 into a pair, there are twice as many of the complementary device produced from the method, shown in FIG. 22, as the primary device, shown in FIGS. 20 and 21. Assuming that equal numbers of both devices are desired, FIGS. 24a and 24b illustrate an alternative method of forming resilient layer strands so that one pair of strands 26 are produced for each single strand 26b.

Figure 24A:
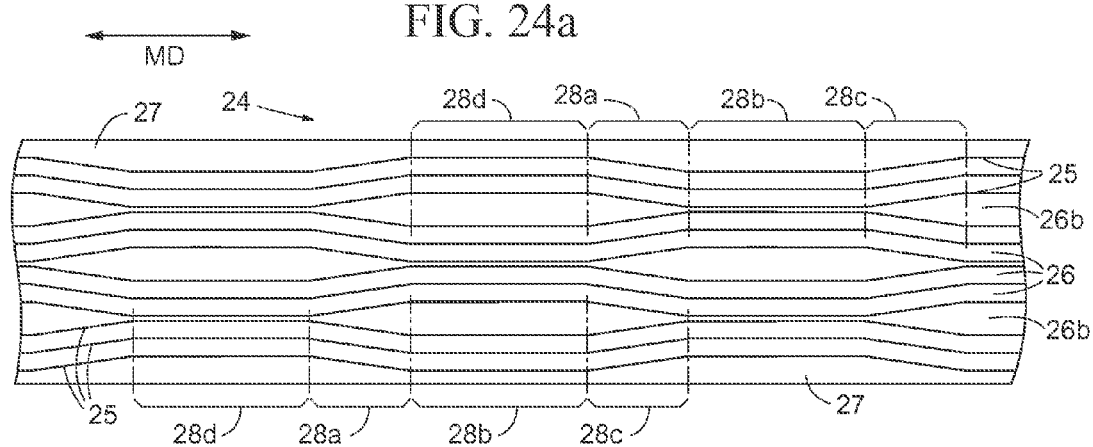
FIG. 24a is a fragmentary plan view illustrating an alternative to the initial steps of the fifth form of manufacturing method.
Figure 24B:
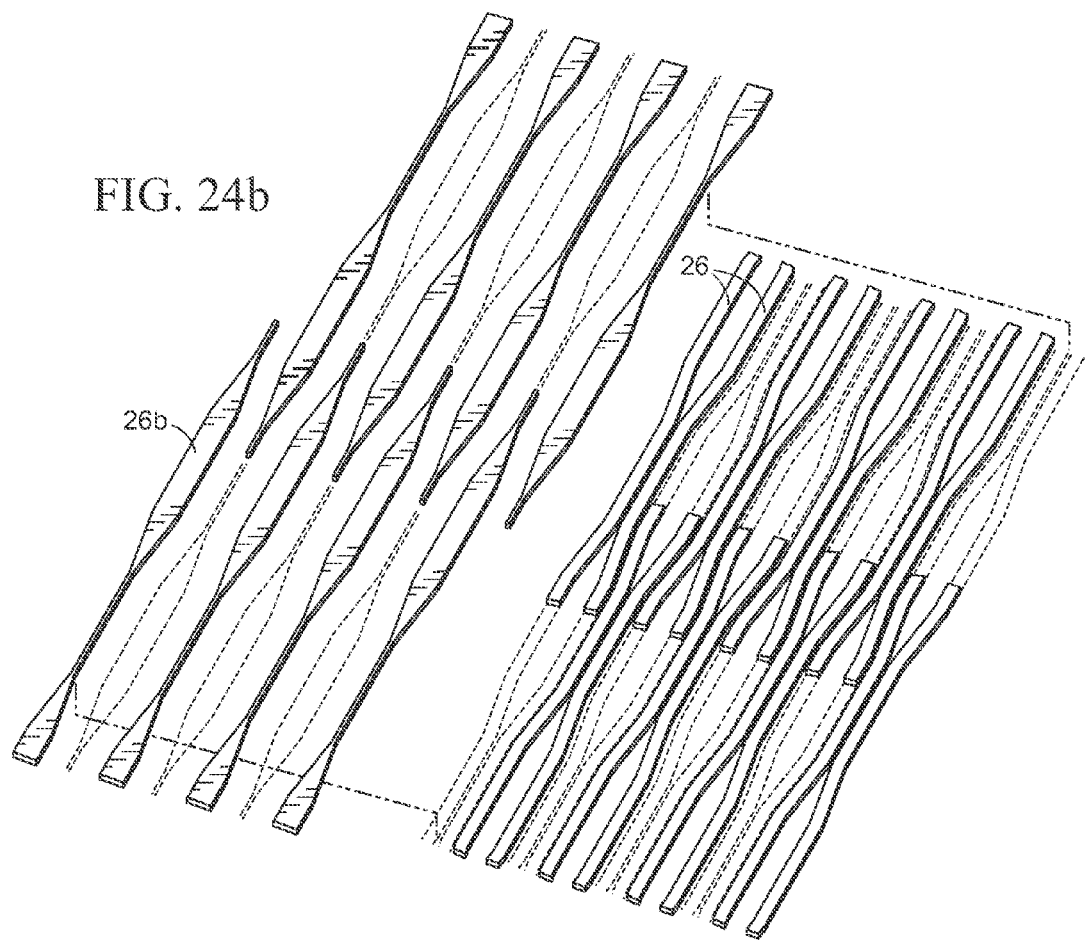
FIG. 24b is an exploded fragmentary perspective view illustrating elongated material strands from FIG. 24a separated into two groups.

FIG. 24a shows slits 25 formed in resilient layer film 24 such that two strands 26 are laterally followed by strand 26b, followed by two opposing strands 26, and again followed by strand 26b. The upper set of brackets show segments 28a-28d of strand 26; the lower set of brackets show segments 28a-28d of strand 26b. FIG. 24b shows resilient layer strands 26 and 26b separated into two groups to illustrate twice the number of individual strands 26 (sixteen) separated from (eight) individual strands 26b, thus making equal pairs of strands 26 to individual strands 26b. For visual clarity, dashed lines are used to illustrate some strands.

FIGS. 25a and 25b illustrate the first of several variations, from myriad possible, to the fifth form of manufacturing method discussed with regard to FIGS. 23a and 23b. Like the resilient layer strands shown in FIGS. 24a and 24b, strands 26 and 26b of the present embodiment are formed in equal numbers, alternating across the width of resilient layer film 24. So as not to repeat previous disclosure, FIG. 25a is limited to illustrating resilient layer strand configuration and the matching of resilient strands to dilator devices. It is understood that the strands maintain their lateral spacing as illustrated when combined into a material laminate, as described hereinbefore, and that a material laminate is formed as previously disclosed.

Broken lines and brackets indicate segments 28a-28c of resilient layer strand 26 aligning with the horizontal regions of a first dilator device, shown by dashed lines at the top of FIG. 25a. Strand 26 is configured wide enough so that a single resilient member in the finished device has suitable spring biasing properties. Broken lines and brackets indicate segments 28a-28c of resilient layer strand 26b aligning with the horizontal regions of a complementary dilator device, shown by dashed lines at the bottom of FIG. 25a. FIG. 25b shows equal numbers of strands 26 and 26b separated into two groups. Dashed lines represent where strands 26b formerly occupied the spaces in between strands 26.

Figure 26:
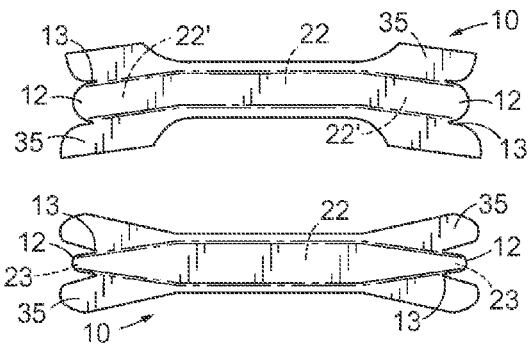
FIG. 26 is a plan view of a sixth form of nasal dilator in accordance with the present invention, produced from the method of FIGS. 25a and 25b.

FIG. 26 more particularly illustrates the finished dilator devices. The first device, shown at the top of the figure has divergent resilient member components 22' corresponding substantially to respective end regions of the truss. The truss end regions also diverge laterally in the same manner. The complementary device is a variation on the dilator of FIG. 22, featuring a resilient member having long edges which taper gradiently from a wider rectangular portion to narrower terminal end portions 23. The longitudinal extent of the tapered portions correspond to the device end regions, and terminal end portions correspond to protrusions 12, with material separations 13 adjacent thereto.

Figure 27:
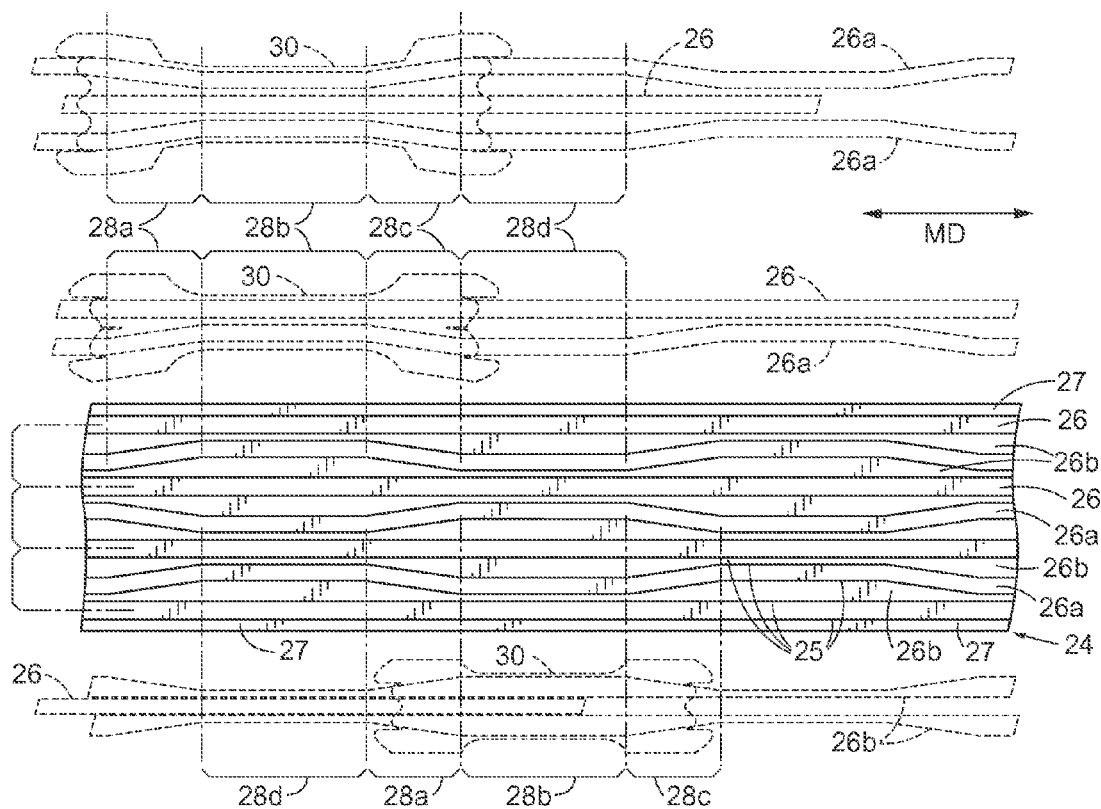
FIG. 27 is a fragmentary plan view illustrating an overview of a second variation of the fifth form of manufacturing method.

FIGS. 27-31b illustrate a second variation to the preceding fifth form of manufacturing method. This variation forms three different configurations of resilient layer strands from a web of resilient layer film to produce complementary dilator devices. FIG. 27 shows an overview wherein continuous slits 25 form resilient layer strands 26, 26a and 26b in resilient layer film 24 as described hereinbefore. The strands are formed in an alternating pattern which repeats laterally between the longitudinal centerlines of consecutive strands 26, as indicated by brackets and broken lines to the left of the drawing figure. Strand 26 is substantially straight and slightly wider than strand 26a. Strand 26 has portions which diverge laterally, and strand 26b is formed in between strands 26 and 26a.

As seen at the top of FIG. 27, horizontal brackets with broken lines indicate segments 28a-28c of resilient layer strands 26, 26a and 26b corresponding to the intermediate and end regions of truss 30. Strands 26 and 26a may be combined in the fabrication of at least two distinct devices, one larger and one smaller, as shown by dashed lines. Where two strands 26b are separated laterally therebetween by strand 26, strands 26b may be combined in the fabrication of another device, optionally including strand 26 therebetween, illustrated by dashed lines per the lower set of brackets at the bottom of FIG. 27. Segment 28d of all strands determines, at least in part, the spacing between die cut lines which form finished devices.

So as not to repeat previous disclosure, FIG. 27 is limited to illustrating resilient layer strand configuration and the matching of resilient strands to dilator devices. It is understood that the strands maintain their lateral spacing as illustrated when combined into a material laminate, as described hereinbefore, and that the material laminates are formed by way of techniques described hereinbefore.

FIGS. 28 and 29 illustrate the dynamic relationship between strand widths, strand spacing, and the resilient layer structures of finished dilator devices produced by the present method. Broken lines in FIG. 28 indicate the width of the resilient layer strand (26), which forms the upper resilient member 22 of dilator 10 on the right, corresponding to the spacing between upper and lower resilient members 22 of dilator 10 on the left. The width of the former determines the spacing of the latter, and vice versa. Similarly, broken lines in FIG. 29 indicate the configuration of the resilient layer strands (26b), which form adjacent resilient members 22 of dilator 10 on the right. That configuration affects the spacing and divergent portions of uppermost and lowermost resilient members 22 of dilator 10 on the left. The configuration of the former determines, in part, the configuration of the latter, and vice versa. A third resilient member, in between the uppermost and lowermost resilient members in the dilator on the left, may be optional in both dilator devices, right and left.

FIGS. 28-29 also illustrate features of diverse dilator devices which may be produced from the present method. Dilator 10 to the right in FIG. 28 is horizontally symmetric but laterally asymmetric. Each horizontal half of the truss on each side of lateral centerline b is a mirror image of the other. The upper half of the truss is formed parallel to longitudinal centerline a. The lower half diverges from longitudinal centerline a at each end region of the truss. Upper resilient member 22 aligns with the nasal valve, while lower resilient member 22 has resilient member components 22' to better engage outer wall tissues of the nostril or nasal vestibule. Lower tab extension 35 correspond to components 22'. Each of two resilient members 22 may have a different width, the upper member being, in this case, slightly wider than the lower. Valley 21 is formed as a narrow elongated opening between upper and lower resilient members.

The dilator to the left in FIG. 28 has identical adjacent resilient members each having tapered portions extending generally along end regions 32 and 34 to terminal end portions 23 and protrusions 12. Were there an optional third resilient layer strand (26) remaining therebetween, the resilient layer would have three laterally contiguous resilient members absent any separation between their respective long edges. In either case, the resilient members' collective width applies spring biasing forces to a slightly greater vertical surface of the nose given the device's shape and size. Dilator 10 to the left in FIG. 29 is proportionately larger than its counterparts, and thus more suited for larger noses. Its spring biasing forces are spread widely at end regions 32 and 34 by virtue of divergent components 22'. Material separation 13 is adjacent each tab extension 35, and valley 21 is positioned between the middle protrusion 12 and upper and lower protrusions 12 to either side thereof.

Figure 30:
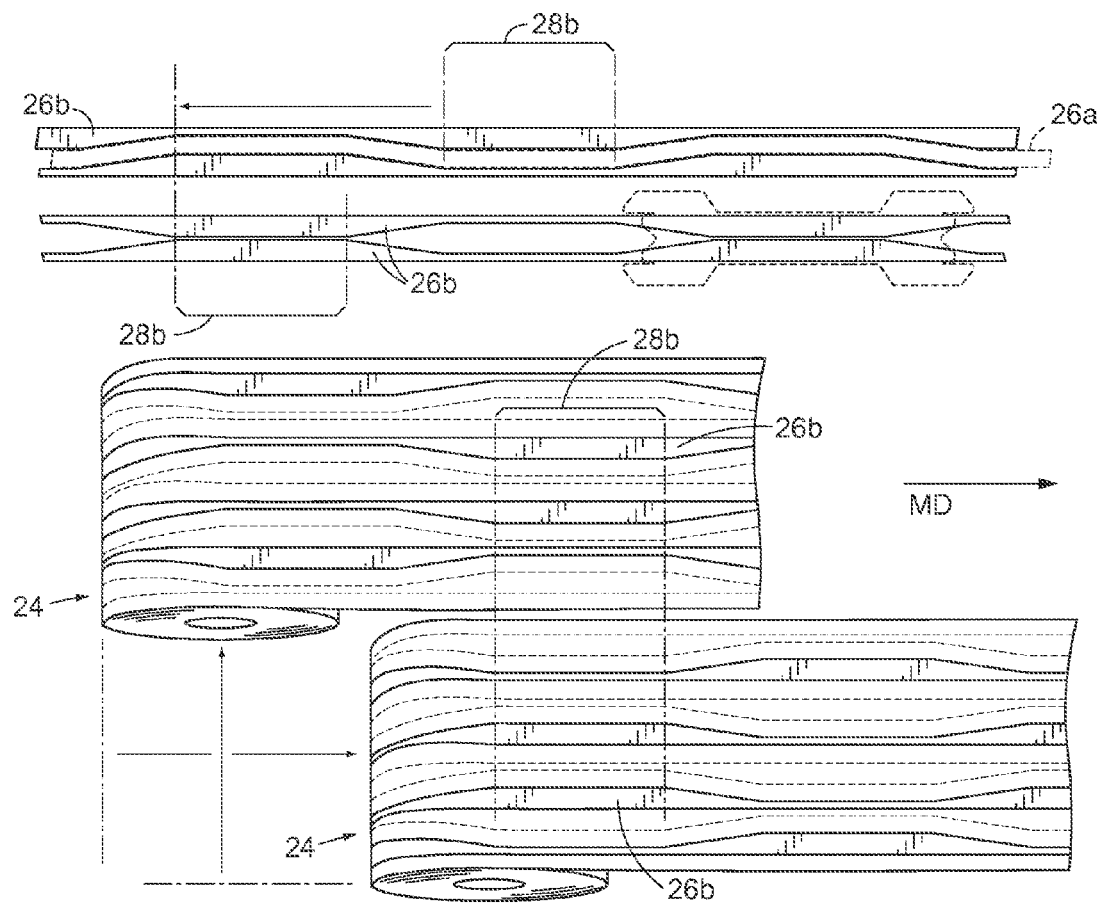
FIG. 30 is a fragmentary plan view illustrating an arrangement of material webs to facilitate optional steps of the second variation, shown in FIG. 27, to the fifth form of manufacturing method.

Referring momentarily back to FIG. 27, opposing strands 26b are the mirror image of each other and longitudinally staggered where separated laterally therebetween by strand 26a. That configuration is also illustrated at the top of FIG. 30. Strands 26b may be combined to form another useful resilient layer structure by shifting every other strand 26b longitudinally so as to align segments 28b opposite each other, as indicated by broken lines, brackets, and a directional arrow. To align strands 26b in this manner, separate resilient layer film webs 24 are arranged as shown at the bottom of FIG. 30. The webs must overlap one another, and may be staggered longitudinally, as indicated by directional arrows. A bracket with broken lines extending across the width of webs 24 indicates the desired alignment. For illustrative clarity, some of the strands in the resilient layer film webs are represented by dashed lines.

Figure 31A:
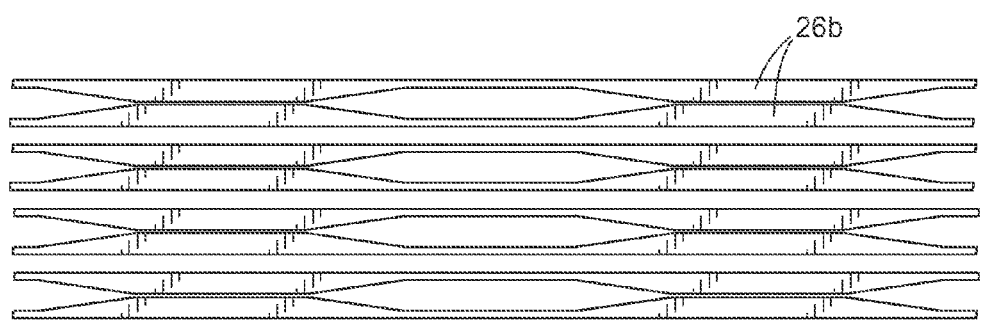
FIGS. 31a and 31b are fragmentary plan views illustrating the subsequent steps of the optional steps begun in FIG. 30.
Figure 31B:
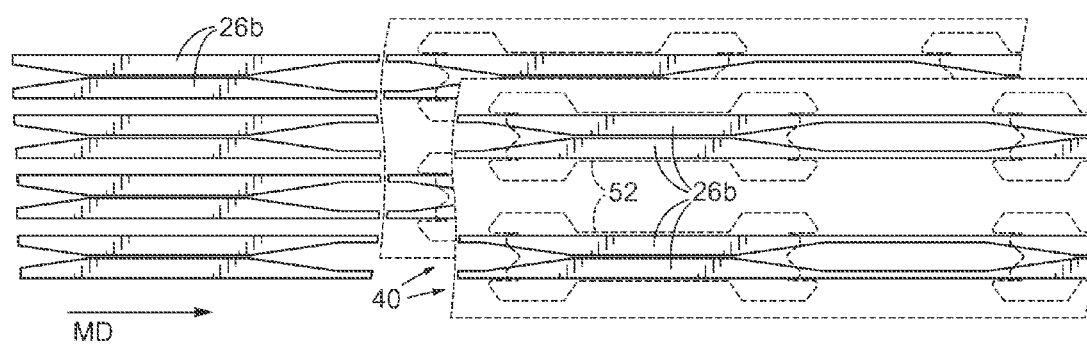

The overlapping arrangement of resilient layer film webs 24 allows opposing strands 26b to be peeled away in matching pairs, as seen in FIG. 31a. (The technique is the same, in principle, as that discussed previously with respect to FIG. 17a.) FIG. 31b shows how every other pair is combined into respective material laminates 40 using means described hereinbefore. Dashed lines illustrate where die cut lines 52 form rows of finished dilators suitably spaced apart for sealing between packaging webs.

Figure 32:
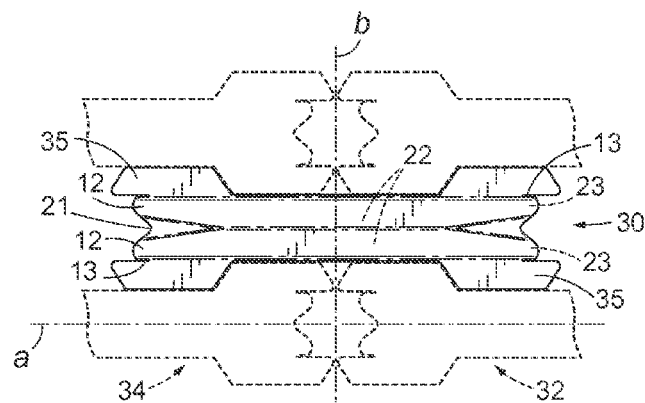
FIG. 32 is fragmentary plan view of a tenth form of nasal dilator in accordance with the present invention, produced from the optional steps described with regard to FIGS. 30-31b.

FIG. 32 more particularly illustrates the finished dilator device as having adjacent resilient members 22 positioned closely along their respective shorter long edges. The tapered portion extends from inward, near the longitudinal centerline of truss 30, to outward, forming a directional element which reduces the spring biasing force of the truss. The gradient edges also create a space in which to form valley 21. Protrusions 12 are thus positioned immediately adjacent material separations 13 and tab extensions 35. This end edge structure is conducive to the desirable design practice of shifting peel forces to sheer forces, as described hereinbefore.

FIG. 32 further illustrates that the truss is symmetric on both sides of its lateral centerline, b, and symmetric on both sides of its longitudinal centerline a. Both sides are the mirror image of the other. Laterally adjacent dilators may be staggered lengthwise so that substantially all of their long edges are fabricated on a common die cut line, as illustrated by dashed lines and described previously with regard to FIG. 4. To facilitate common die cut line fabrication, the inside lateral edges of upper and lower tab extensions 35 are formed to the same angle and corner radius. Additionally, the truss regions are configured so that the long edges of two opposing end regions of two successive dilator peripheries fit into the space between, and on a common line with, the inside lateral edges of tab extensions and the long edge of the truss between the tab extensions of the dilator peripheries adjoining on either side.

The device of FIG. 32 may be mass produced in a spaced apart relationship, as illustrated in FIGS. 30-31b. FIG. 32 illustrates that the device is also configured to be fabricated contiguously on common die cut lines. The skilled person in the art may observe that the configuration of resilient layer strands 26b in FIGS. 31a and 31b precludes common line die cutting as shown in FIG. 32. However, a different resilient layer strand configuration, such as that discussed previously with regard to FIG. 5b, 6b, 12, or 17a, may be adapted for the purpose.

Figure 33:
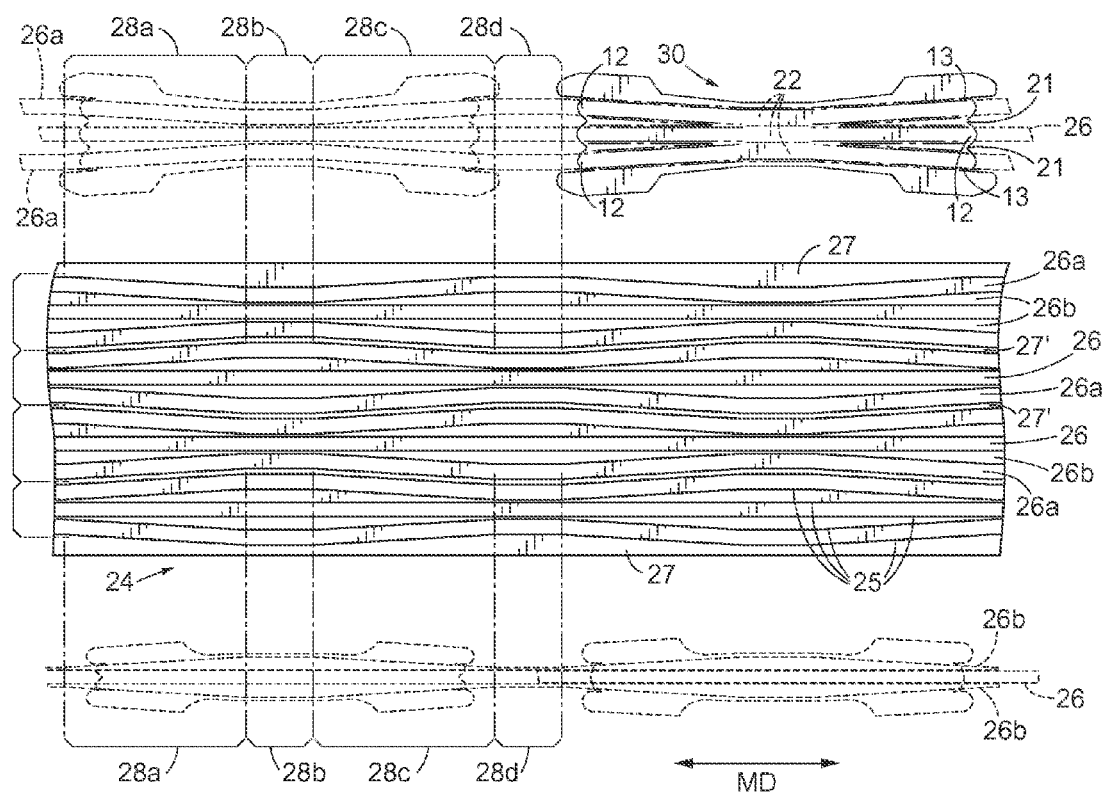
FIG. 33 is a fragmentary plan view illustrating an overview of a third variation of the fifth form of manufacturing method, including an eleventh form nasal dilator in accordance with the present invention produced therefrom.

FIG. 33 illustrates a third variation of the fifth form of manufacturing method of the present invention. Continuous slits 25 form resilient layer strands 26, 26a, 26b, as described hereinbefore, plus an inside waste strand, 27'. The strands are formed in a repeating pattern across the width in resilient layer film 24. Waste strand 27' is formed in between two parallel strands 26a at each point where the pattern is repeated, as indicated by broken lines and brackets to the left of the drawing figure. Strand 26 is straight, while strands 26a diverge laterally. Each opposing pair of strands 26b are laterally separated by a strand 26 therebetween.

Upper and lower sets of horizontal brackets with broken lines indicate segments 28a-28c of the resilient layer strands aligning with dilator devices. As seen in the upper set of brackets, dashed lines illustrate strand 26 and opposing strands 26a aligning with dilator regions so as to form a triple resilient band resilient layer structure. The finished device is depicted to the right thereof, showing divergent upper and lower resilient members and a straight middle resilient member. Material separations 13 are adjacent each upper and lower protrusion 12, and valley 21 is positioned between the middle protrusion 12 and the upper and lower protrusion 12 on either side.

In the lower set of brackets dashed lines illustrate two opposing strands 26b, which would otherwise be waste material, combined to form resilient layer structures of two additional complementary devices. Strand 26 may be included between opposing strands 26b in one of the two complementary devices shown, and as more particularly illustrated in FIG. 38.

Figure 35:
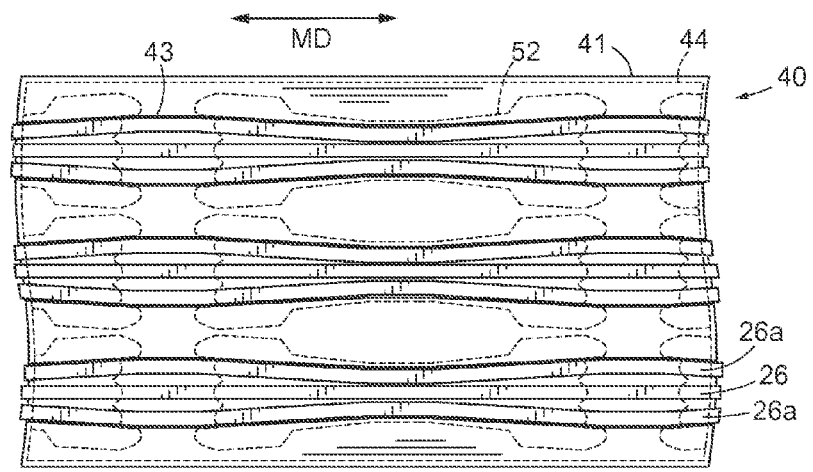
FIG. 35 is a fragmentary plan view illustrating subsequent steps of the third variation of method described with respect to FIG. 33 whereby to produce the eleventh form of dilator device.
Figure 34:
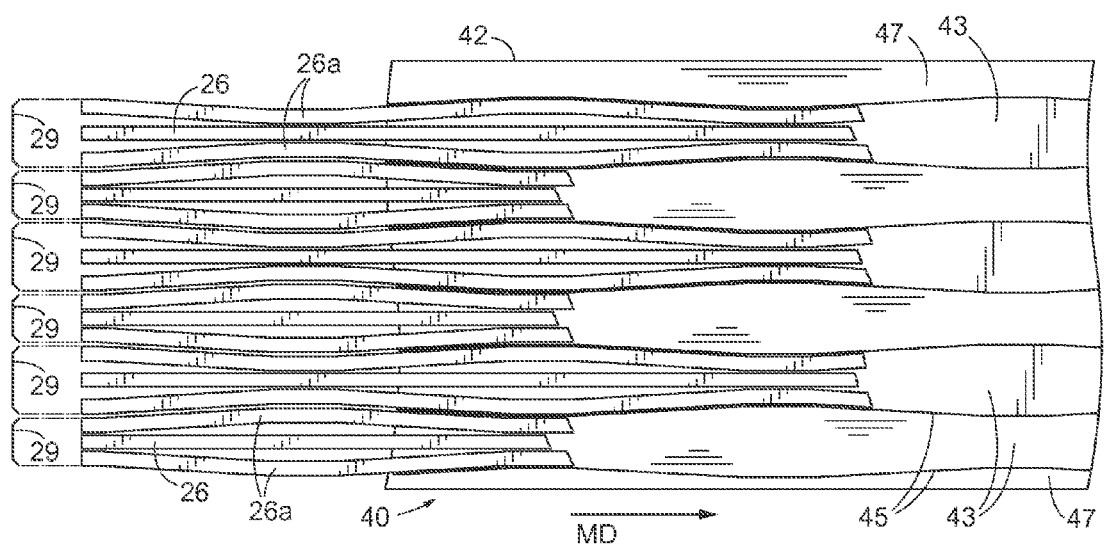
FIG. 34 is a fragmentary plan view illustrating initial steps of the third variation of method described with respect to FIG. 33 whereby to produce the eleventh form of dilator device.
Figure 37:
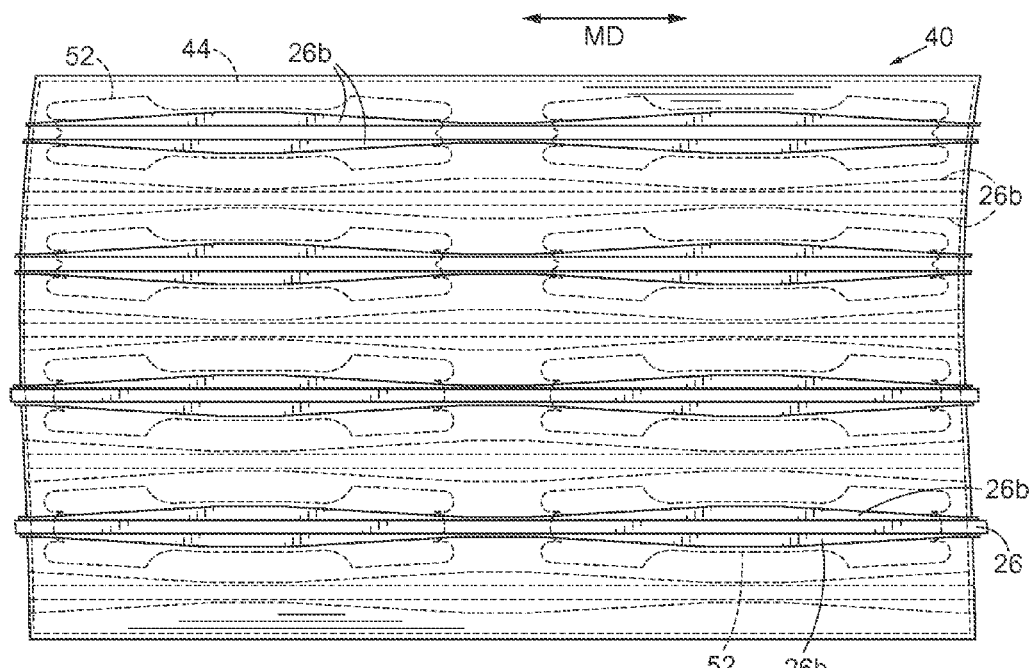
FIG. 37 is a fragmentary plan view illustrating subsequent steps involved in the third variation of method of FIG. 33 whereby to produce a complementary dilator device.
Figure 36:
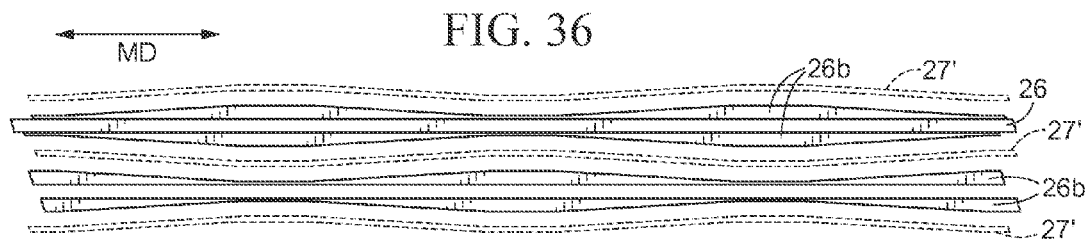
FIG. 36 is a fragmentary plan view illustrating initial steps involved in the third variation of method of FIG. 33 whereby to produce complementary dilator devices.

FIGS. 34-35 and FIGS. 36-37, respectively, illustrate resilient layer strands combined into respective material laminates. The lateral spacing between strands is determined by the width and configuration of strands separated from the spaces therebetween: FIG. 34 shows group 29 comprising one resilient layer strand 26 with opposing strands 26a adjacent either side. Strands 26 and 26a are laterally separated by the width of strands 26b formerly therebetween, and adjacent groups 29 are separated by a the width of waste strand 27' formerly therebetween. Waste strand 27' is removed and discarded as necessary waste, and strands 26b are combined into another material laminate (as illustrated in FIGS. 36 and 37). This leaves groups 29 laterally positioned for combining with base layer strands and a cover layer material web into material laminate 40.

FIG. 34 shows each group 29 separated from resilient layer film 24 and layered onto base layer strands 43, the latter having been formed in base layer material 42 by continuous slits 45 as described hereinbefore. Strands 43 are configured to conform to device requirements and to align with groups 29. Every other strand 43, each with a group 29 thereon, are separated onto one or more separate release paper liners 41 as shown in FIG. 35 (in the same manner as described previously with respect to FIGS. 9a-9c and 15a-15b). Cover layer material 44, shown by dashed lines, is laminated by its adhesive side onto the resilient layer strands, base layer strands 43 and separate release paper liner 41 to complete material laminate 40. Dashed lines illustrate where enclosed die cut lines 52 form rows of successive finished dilators 10 as described hereinbefore.

FIG. 36 illustrates two pairs of opposing strands 26b separated by the collective widths of inside waste strand 27' and strands 26a (the former represented by dashed lines, and the latter not represented for illustrative clarity). However, strand 26 may be included between some of the opposing pairs of strands 26b as more clearly seen in FIG. 37. FIG. 37 shows every other of paired strands 26b combined into material laminate 40. Pairs of strands not so combined are represented by dashed lines, and these may be combined into a separate material laminate. Enclosed die cut lines 52 form peripheries corresponding to finished dilator units in a spaced apart relationship suitable for sealing between packaging webs. Two similar, complementary, dilator devices are thus formed in material laminate 40 by die cut lines 52. One of the two devices includes a third resilient member provided by strand 26.

Figure 38:
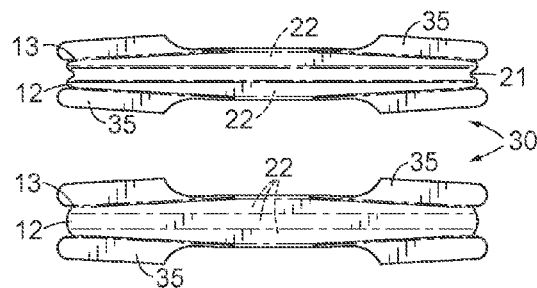
FIG. 38 is a plan view illustrating two versions of a twelfth form of nasal dilator in accordance with the present invention, produced as complementary devices from the third variation of method illustrated with respect to FIGS. 36 and 37.

FIG. 38 more particularly illustrates the two complementary dilator devices having similar narrow peripheries. The devices are comparatively smaller and lighter than their larger counterpart produced by this process, and thus more suited for smaller noses. One device has a triple band resilient layer structure, and one device is formed as a double resilient band structure. Adjacent resilient members taper in the same manner as shown previously. Resilient member terminal end portions 23 of the double resilient member band device correspond to respective protrusions 12, with valley 21 therebetween, at each end edge of the truss. The terminal end portions of the device having three laterally contiguous resilient members correspond to a single protrusion 12 at each end edge of the truss.

FIG. 39 more particularly illustrates dilator 10, as previously shown in FIG. 33, die cut from material laminate 40 shown in FIG. 35. Base member 14 is interposed between at least the peripheral extent of resilient layer and the skin surfaces engaged by dilator 10, its periphery corresponding substantially to the resilient layer, yet distinct from both the resilient layer and the cover layer. The resilient layer features three resilient members; the upper and lower resilient bands feature divergent components 22' extending laterally from the intermediate region through end regions 32 and 34. The resilient layer further has a substantially rectangular center resilient member band interposed between the upper and lower resilient bands.

FIG. 40 illustrates several examples of rectangular single resilient band and multiple resilient band structures. For simplicity, multiple bands are shown substantially the same width and arranged closely parallel each other. At the top of the figure, a single resilient band and the pair of resilient bands below it represent average or typical configuration found in nasal dilator art. Below that, a three band structure may be used to increase, by some degree or percentage, the amount of spring biasing force over that which is generally found in a single band or double band structure. The same or similar spring biasing of from one to three bands may also be spread across four narrower bands. And the increased spring biasing generated by one to four bands may be generated by a five or six still narrower bands. Additionally, one or more individual bands may be of a different width or thickness. Elongated resilient layer strands combined from separate resilient layer film webs, as illustrated herein, facilitates formation of resilient layer structures having multiple bands of both different thickness and width.

Figure 50C:
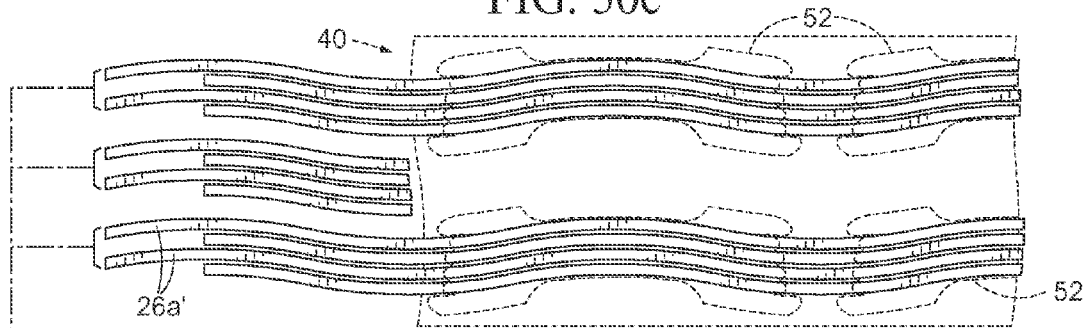
FIGS. 50a-50c are fragmentary plan views illustrating a seventh form of manufacturing method in accordance with the present invention for producing arcuately shaped devices.
Figure 50A:
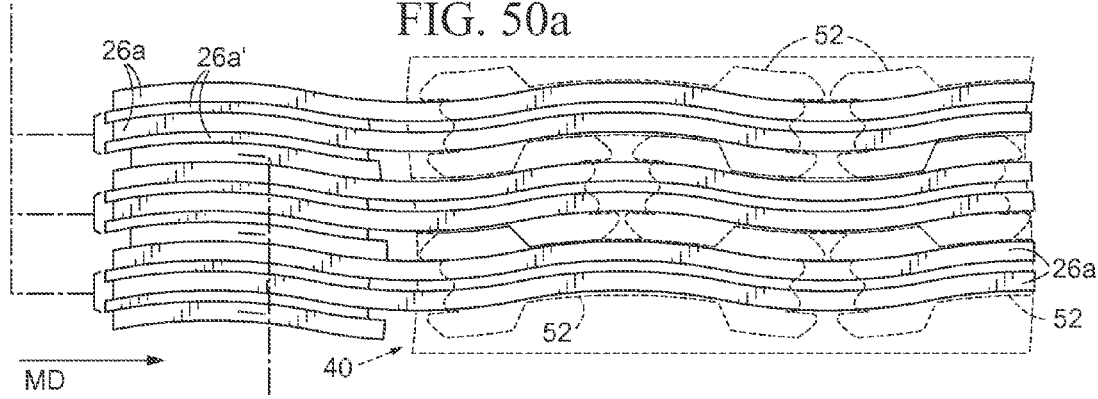
Figure 50B:
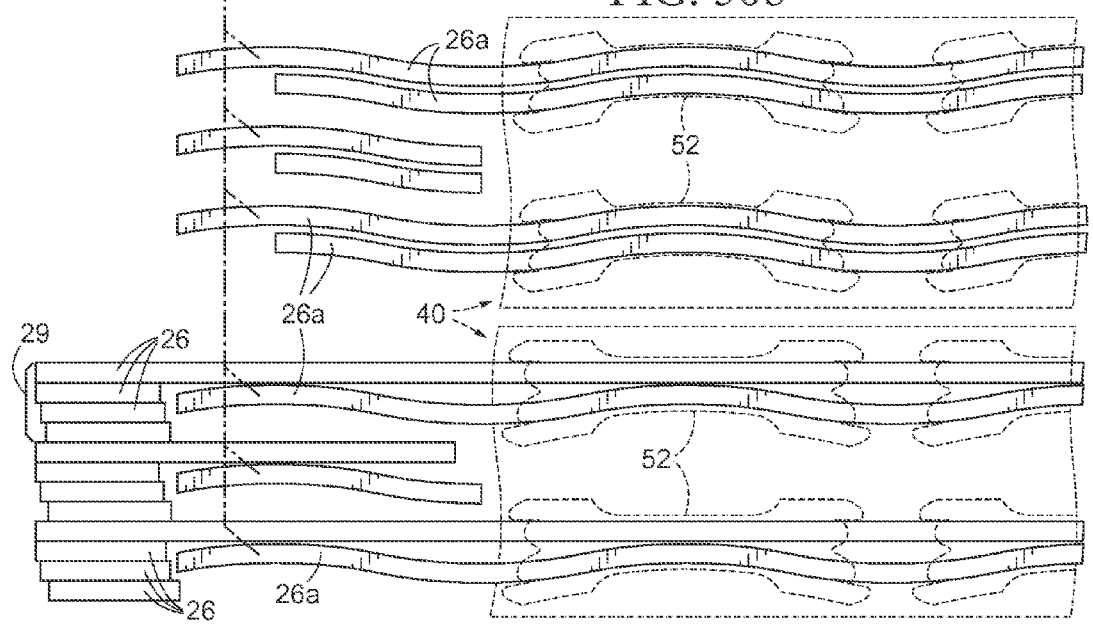

FIGS. 41-43 illustrate a sixth form of manufacturing method, in accordance with the present invention, applicable to a variety of medical devices, but particularly suited to dilator devices having multiple parallel resilient bands. So as not to repeat previous disclosure, FIGS. 50a-50c illustrate resilient layer strand configuration, the combining thereof into material laminates, and the positioning of die cut lines in the laminates. Resilient layer strands are produced from webs of resilient layer film and distributed to the material laminates as required. It is understood that the strands maintain their lateral spacing as illustrated when combined into a material laminate, as described hereinbefore, and the material laminates are understood to be completed by way of techniques described herein.

As seen in FIG. 41, alternating wider and narrower resilient layer strands 26 and 26', respectively, are slit from a web of resilient layer film (or alternatively, from two or more webs of different thickness) as described hereinbefore. Slits 25 are preferably straight and respective strands 26 and 26' preferably uniform in width.

FIGS. 42a, 42b and 43 show resilient layer strands 26 and 26' separated from resilient layer film 24 into respective material laminates. The strands in each material laminate are identical; each strand laterally spaced apart by the width of the strand formerly therebetween. As discussed previously, rather than resilient layer strands 26' being waste material by which to laterally space strands 26 apart, slits 25 configure both strands 26 and 26' to be used in complementary devices.

FIGS. 42a and 42b illustrate that resilient layer strands 26 may be incorporated into material laminate 40 in two different ways. To the left in FIG. 42a, groups 29 comprise five strands 26 each. The first three adjacent strands are incorporated into a first material laminate 40 and the following two adjacent strands are placed into a second material laminate 40 (shown next to the first laminate 40). Enclosed die cut lines 52 form rows of dilator devices: Every other row of die cut lines 52 in the first laminate 40 is flipped laterally and is longitudinally staggered so that finished devices are positioned laterally closer thereby using less engagement element material. In the second laminate 40, die cut lines 52 form a smaller complementary device having two parallel resilient bands.

Alternatively, FIG. 42b shows group 29 comprising three resilient layer strands 26. Each one in three adjacent groups 29 is combined into material laminate 40 so that rows of successive die cut lines 52 have suitable lateral spacing for packaging material webs to form a perimeter seal. Additionally, strips of cover layer material 44, having a width slightly greater than that of the peripheries formed by die cut lines 52, may be aligned with the longitudinal centerline of group 29 or die cut lines 52 (similar to that discussed previously with regard to FIG. 12).

FIG. 43 shows a first plurality of resilient layer strands 26' evenly spaced apart as seen in FIG. 41. The spacing is equal to the width of strands 26 formerly therebetween, as represented by dashed lines. A second plurality of strands 26' are intermingled with the first plurality, positioned in the spaces therebetween and corresponding to the same longitudinal centerlines as did strands 26. Two pluralities of strands 26' are thus intermixed and laterally spaced as evenly as practicable. Group 29 comprises six adjacent strands 26'. Every other adjacent group 29 is combined into material laminate 40.

FIG. 43 further illustrates by dashed lines where enclosed die cut lines 52 (only fragmentary portions thereof are shown) form longitudinally staggered dilator peripheries, similar to that shown in FIG. 42a. Additionally, continuous slits 45 are placed in material laminate 40 in the spaces between the long edges of adjacent rows of die cut lines 52 to form elongated finished strands from which finished dilators are die cut (as described previously with regard to FIGS. 17b-17d). The skilled person in the art will recognize that groups 29 in FIG. 43 may be configured with different numbers of resilient strands so as to match a variety of dilator device sizes and widths.

FIGS. 42 and 43 each illustrate resilient layer strands having identical width. The strands may be of different widths, and if slit from separate resilient layer film, of different thickness. Forming resilient layer strands of different thickness allows both width and thickness to be design variables together with the number of resilient members which form the dilator resilient layer.

FIGS. 44-46 more particularly illustrate finished dilator devices produced from the method of FIGS. 41-43. FIG. 44 shows dilator 10 produced from the material laminate shown in FIG. 42a, or alternatively, from the material laminate shown in FIG. 42b. The device has three parallel resilient members 22 of progressively less length. If the resilient members are the same width and thickness, a shorter band will have more spring biasing force than a longer band. The elements of end edges 33 (protrusions 12, valleys 21, separations 13 and tab extensions 35) correspond generally to an inward angle, as indicated by broken lines, established by the resilient bands' lengths. That angle also corresponds generally to the line where the nose meets the cheek.

FIG. 45 shows dilator 10 fabricated from the material laminate shown in FIG. 42a. Dilator 10 is a conventional double band design, formed as a complementary device to dilator 10 of FIG. 44. It is smaller in size than its counterpart, and thus suitable for smaller noses. The dilator of FIG. 46, produced from the material laminate shown in FIG. 43, has six narrow parallel resilient members 22. Three protrusions 12 at each end edge 33, separated therebetween by two valleys 21, correspond to terminal end portions 23 of two adjacent resilient members 22. Material separations 13 are adjacent the upper corners of the uppermost resilient member band and the lower corners of the lowermost resilient member band, respectively.

Figure 48:
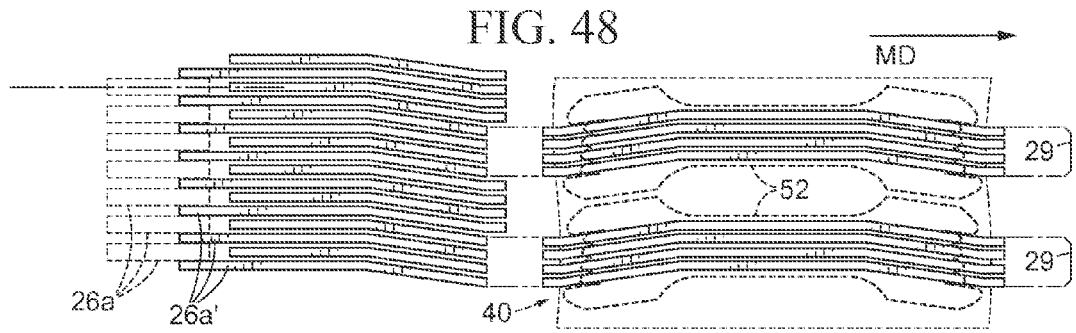
FIG. 48 is a fragmentary plan view illustrating subsequent steps to the variation of the sixth form of manufacturing method whereby to produce arcuately shaped dilator devices.
Figure 47:
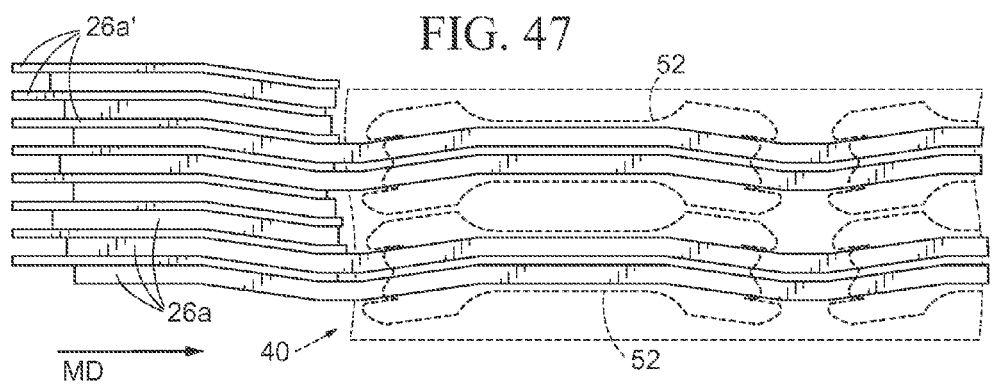
FIG. 47 is a fragmentary plan view illustrating an overview of initial steps to a variation of the sixth form of manufacturing method whereby to produce arcuately shaped dilator devices.

FIGS. 47-48 illustrate an overview of an alternative to the sixth form of manufacturing method whereby to produce dilator devices having an arcuate-like shape (an example thereof illustrated in FIG. 26). The intermediate region of an arcuate dilator device rests slightly higher on the bridge of the nose, its end regions positioned correspondingly lower than that of horizontally straight dilator devices, so as to engage outer wall tissues adjacent both the nasal valve and the nasal vestibule.

So as not to repeat previous disclosure, FIGS. 47-48 illustrate resilient layer strand configuration, the combining thereof into material laminates, and the positioning of die cut lines in the laminates. Resilient layer strands are produced from webs of resilient layer film and distributed to the material laminates as required. It is understood that the strands maintain their lateral spacing as illustrated when combined into a material laminate, as described hereinbefore, and the material laminates are understood to be completed by way of techniques described herein.

FIG. 47 shows two sets of alternating wider and narrower resilient layer strands 26a and 26a' slit from an elongated web of resilient layer film (or alternatively, from two or more webs of different thickness), similar to that illustrated with respect to FIG. 41. The strands diverge laterally in a continuous repeating pattern. Strands 26a and 26a' may be combined into separate material laminates without first being divided into respective groups of identical strands. Every other pair of adjacent resilient layer strands 26a are combined into material laminate 40. Dashed lines illustrate die cut lines 52 forming adjacent rows of successive finished dilator units, similar in appearance to the dilator of FIG. 26, where the end regions diverge as do the resilient members, giving the finished dilator the appearance of an arcuate shape.

FIG. 48 shows a first plurality of resilient layer strands 26a', separated from strands 26a as seen in FIG. 47. Each strand 26a' is laterally spaced apart by a distance equal to the width of strand 26a formerly therebetween, as represented by dashed lines. A second plurality of strands 26' are intermingled with the first plurality, positioned in the spaces between each strand 26' and corresponding to the same longitudinal centerlines, indicated by a broken line, as strands 26a. Both pluralities of strands 26' are thus laterally spaced as evenly as practicable.

Figure 49:
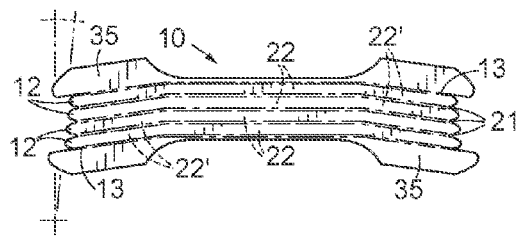
FIG. 49 is a plan view of an alternative form of the nasal dilator of FIGS. 26 and 47, produced from the method described with regard to FIG. 48.

Every other adjacent group 29, comprising four resilient layer strands 26a' each, is combined into material laminate 40. Die cut lines 52 form finished dilator devices, similar to that shown in FIG. 47, where the end regions of the truss correspond to the divergent segments of strands 26a'. As noted previously, strands 26 and 26a' may be formed from webs having different thickness. For example, resilient layer strands of the above referenced second plurality, having a second thickness, may be intermingled with the first plurality of strands having a first thickness. The four band resilient layer structure of the finished device, more particularly illustrated in FIG. 49, would thus have every other resilient member being one thickness or the other.

FIGS. 50a-50c illustrate a seventh form of manufacturing method, in accordance with the present invention, applicable to a variety of medical devices, but particularly suited to arcuate dilator devices. So as not to repeat previous disclosure, FIGS. 50a-50c illustrate resilient layer strand configuration, the combining thereof into material laminates, and the positioning of die cut lines in the laminates. Resilient layer strands are produced from webs of resilient layer film and distributed to the material laminates as required. It is understood that the strands maintain their lateral spacing as illustrated when combined into a material laminate, as described hereinbefore, and the material laminates are understood to be completed by way of techniques described herein.

FIG. 50a shows alternating wider and narrower resilient layer strands 26a and 26a', similar to that illustrated with respect to FIGS. 41 and 47, slit from a web of resilient layer film (or alternatively, from two or more webs of different thickness) as described hereinbefore. Strands 26a and 26a' diverge laterally in a repeating pattern of successive curved segments. Broken lines indicate that strands 26a and 26a' are separated into several material laminates.

FIG. 50a further illustrates the first two of each three consecutive resilient layer strands 26a combined as pairs with material laminate 40, shown in dashed lines. Dashed lines also illustrate where die cut lines 52 form successive, laterally contiguous, rows of arcuate device peripheries on common longitudinal lines. The overall curvature of each periphery substantially follows the curvature of the resilient layer strands. To further facilitate common die cut line formation, every other row of peripheries is flipped laterally so that the lower long edges of one periphery are formed on a common die cut line with the lower long edges of the periphery adjacent thereto, and the upper long edges of one periphery are formed on a common die cut line with the upper long edges of the periphery adjacent thereto. The pattern repeats laterally across the width of laminate 40.

Figure 51:
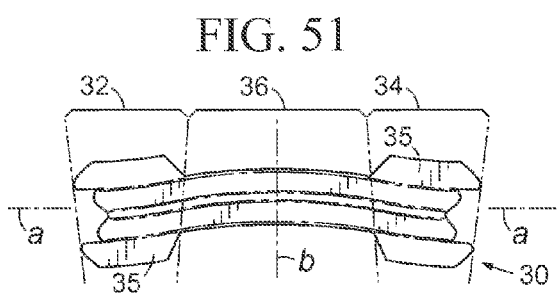

FIG. 51 more particularly illustrates dilator 10 produced from material laminate 40 shown in FIG. 50a. The device is symmetric on each side of lateral centerline b, but asymmetric on each side of longitudinal centerline a. To accommodate the continuous repeating curvature used in the fabrication process, and to form substantial portions of the truss long edges on common lines, upper tab extensions 35 have a slightly dissimilar peripheral shape than lower tab extensions 35. Additionally, as indicated by broken lines and brackets, the upper long edge of intermediate region 36 is shorter than the lower long edge thereof. Also, the upper half of respective end regions 32 and 34 have a greater longitudinal extent than the lower half. To follow the repeating curvature of the resilient layer strands, the long edges of the end regions are formed to have the same radius, but reverse curvature, of the intermediate region: the long edges of upper tab extensions 35 and the lower long edge of intermediate region 36 curve laterally inward, and the long edges of lower tab extensions 35 and upper long edge of the intermediate region 36 curve laterally outward.

Returning now to FIG. 50b, broken lines indicate the third of each three consecutive resilient layer strands 26a from FIG. 50a separated as a first plurality from strands 26a'. The strands are combined into the upper of two material laminates 40 shown in FIG. 50b. The first plurality of strands 26a is followed by a second plurality thereof, intermingled with the first plurality so as to form pairs of strands laterally spaced apart. Every other pair of strands is then combined into material laminate 40. Dashed lines illustrate where die cut lines 52 form rows of finished dilators suitably spaced apart for sealing between packaging webs. The finished dilator device is generally illustrated in FIG. 52.

Additionally, or alternatively, broken lines indicate that the third of each three consecutive resilient layer strands 26a from FIG. 50a may also be combined into the lower of two material laminates 40 shown in FIG. 50b. The strands are combined with strands 26 slit from a separate resilient layer film web, which may optionally be of a different thickness. Each one in four select strands 26, from contiguous groups 29, are combined with strands 26a to form pairs. Each pair comprises a curved strand 26a and a straight strand 26. The pairs of strands are laterally spaced apart, with every other pair combined into material laminate 40. Dashed lines illustrate where die cut lines 52 form rows of finished dilators suitably spaced apart for sealing between packaging webs. The finished dilator device is illustrated in FIG. 53.

As seen in FIG. 50c, broken lines and brackets also indicate where strands 26a' from FIG. 50a are separated as a first plurality from strands 26a, to be combined into material laminate 40. The first plurality of strands 26a' is followed by a second plurality thereof, intermingled with the first plurality so as to form laterally spaced groups of four strands 26a' each. Every other group of four strands is then combined into material laminate 40. Dashed lines illustrate where die cut lines 52 form rows of finished dilators suitably spaced apart for sealing between packaging webs. The finished dilator device is illustrated in FIG. 54.

Figure 52:
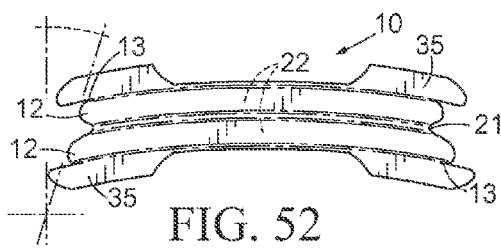
FIG. 52 is a plan view of a sixteenth form of nasal dilator in accordance with the present invention produced from the upper of two material laminates shown in FIG. 50b.

FIG. 52 illustrates a representative example of the arcuate dilator device produced from material laminate 40 seen at the top of FIG. 50b. The long edges of the truss, particularly at the intermediate region, substantially follow the same curvature as two parallel resilient members. The long edges of upper and lower tab extensions 35 may curve in the same or similar manner. The lower resilient member is longer than the upper member, and lower tab extensions 35 extend slightly beyond the upper tab extensions 35. The truss's end edge elements thus angle inward, as indicated by broken lines, to correspond generally to the line where the nose meets the cheek.

Figure 53:
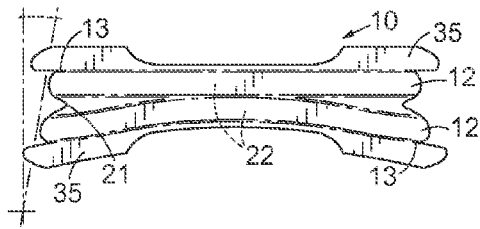
FIG. 53 is a plan view of a variation of the nasal dilator seen in FIG. 28, produced from the lower of two material laminates shown in FIG. 50b.

FIG. 53 illustrates the semi-arcuate dilator device produced from material laminate 40 seen at the bottom of FIG. 50b. The device is particularly similar to the dilator shown to the right in FIG. 28, being horizontally symmetric and laterally asymmetric. Upper tab extensions 35 and upper resilient member 22 are parallel to the longitudinal centerline of the truss, intended to align with the tissues immediately adjacent the nasal valve. The divergent portions of the arcuate resilient member align with the nasal outer wall tissues adjacent the nostrils or nasal vestibule. Lower tab extensions 35 diverge in the same manner, and may extend slightly beyond upper tab extensions 35. The truss's end edge elements thus angle inward, as indicated by broken lines, to correspond generally to the line where the nose meets the cheek.

Figure 54:
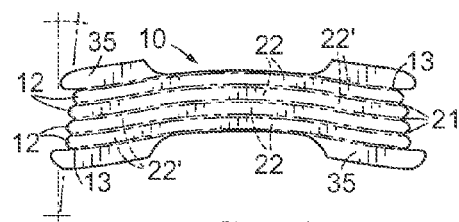
FIG. 54 is a plan view of a four-band version of the nasal dilators seen in FIGS. 51 and 52, produced from the material laminate shown in FIG. 50c.

FIG. 54 illustrates the arcuate dilator device produced from material laminate 40 seen in FIG. 50c. The device is a four-band resilient layer version of the dilator device shown in FIG. 52, and is also similar to the dilator of FIG. 49. The arcuate shape of the truss substantially follows the curvature of the four parallel resilient members. The truss's end edge elements are angled inward, as indicated by broken lines, following the resilient members' progressively shorter length. Spring biasing is thus slightly greater toward the upper part of the device. Terminal end portions 23 correspond to respective protrusions 12, with valleys 21 therebetween, at each end edge of the truss.

The manufacturing method of FIGS. 50a-50c is particularly suitable for continuous rotary die press converting. The skilled converter may note that alternatively, an arcuate device and its constituent elements, members or components could be formed in a circular pattern within a material sheet of fixed size, such as that used in a flat bed press system. Flat bed systems are more suited to successive individual material sheets being fed into the press, as described hereinbefore.

Figure 55:
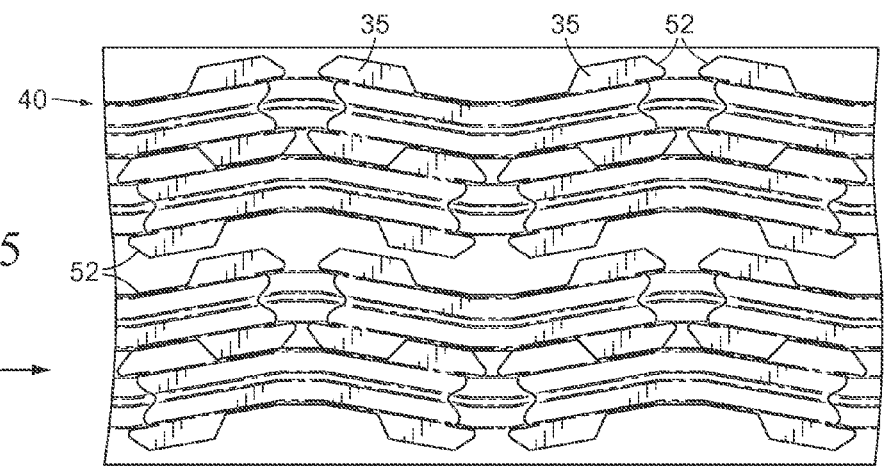
FIG. 55 is a fragmentary plan view illustrating an overview of an eighth form of manufacturing method in accordance with the present invention whereby to produce arcuate-like dilator devices along common lines corresponding to their upper long edges.

In a variation of the manufacturing method shown in FIG. 47, FIG. 55 shows material laminate 40, having pairs of resilient layer strands combined therein. The strands diverge laterally in a continuous repeating pattern and are laterally spaced across the width of material laminate 40. Die cut lines 52 form rows of device peripheries, such that two rows of peripheries are formed substantially on a common die cut line: the upper long edges of the peripheries of one row on a common line with the upper long edges of peripheries of the adjacent row. Each two rows of peripheries align with, and correspond to, two pairs of resilient layer strands. Of necessity, each two rows of peripheries are spaced from the paired rows adjacent thereto, since the device peripheries are configured so as to form only the upper long edges thereof on a common line.

Figure 56:
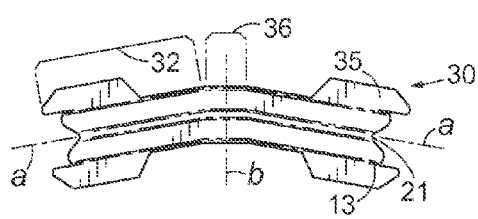
FIG. 56 is a plan view of a seventeenth form of nasal dilator in accordance with the present invention produced from the method described with regard to FIG. 57.

FIG. 55 further illustrates the divergent segments of the strands corresponding to the longitudinal extent of finished dilator device end regions, while a comparatively shorter longitudinal segment corresponds to the shorter intermediate region 36 (more particularly illustrated in FIG. 56). Another shorter longitudinal segment corresponds to the space between successive die cut line peripheries. To facilitate common die cut lines, the truss is configured so that the long edges of two opposing end regions of two successive dilator peripheries fit into the space between the lateral edges of the upper tab extensions, and the upper long edge of the truss between the tab extensions, of the adjacent periphery. FIG. 56 more particularly illustrates the finished device, where the truss is symmetric on both sides of lateral centerline b, and each end region, by itself, is symmetric on each side of its longitudinal centerline a.

Figure 57:
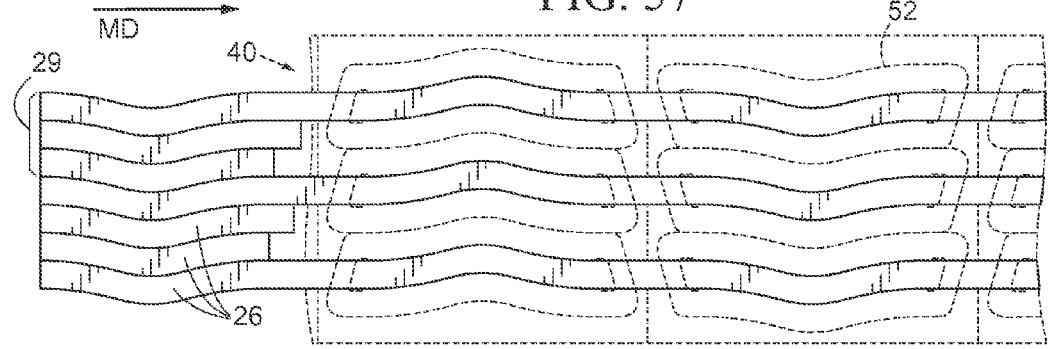
FIG. 57 is a fragmentary plan view illustrating a variation of the manufacturing methods shown in FIGS. 5b-5c and 50a, whereby to produce arcuately shaped dilator devices on common longitudinal lines.

FIG. 57 illustrates a variation of the manufacturing method shown in FIG. 50a. Resilient layer strands 26 have both straight and curved segments, the former corresponding to finished dilator end regions and the latter corresponding to the intermediate region. Resilient layer strand 26 curves laterally from a horizontal segment to form a comparatively short radial protrusion, then curves laterally in the reverse direction back to a longitudinally straight segment. Straight segments also correspond the space between successive dilator peripheries formed by die cut lines 52. Adjacent groups 29 each comprise three laterally contiguous resilient layer strands 26. As described hereinbefore, the widths of group 29 and device peripheries are each configured to suitable design parameters and so that one strand 26 from each consecutive group 29 aligns with each row of die cut line peripheries.

Die cut lines 52 form dilator peripheries having identical opposing long edges, which also conform to the long edges of strands 26. Finished devices are die cut entirely on common longitudinal lines. Accordingly, the finished device does not have end edge elements such as tab extensions or material separations. Rather, the long edges of the truss extend from one end region through the intermediate region to opposite end region on an unbroken line. Similarly, the truss end edges extend in a straight line from the upper outside corner to the lower outside corner thereof. Dashed lines illustrate that material laminate 40 may be bisected between successive finished devices to segment and encapsulate finished devices between packaging webs, as illustrated previously with respect to FIGS. 9e and 10.

As illustrated and described in examples of the preferred embodiments, the present invention provides methods of manufacturing medical devices, particularly devices for dilating external tissue, including a wide range of diverse and complex nasal dilator devices.

I claim:

1. A plurality of nasal dilators comprising:
an engagement element and a resilient layer laminated together; the engagement element at least substantially defining a dilator periphery, the dilator periphery defining opposite dilator end regions, the end regions being wider than an intermediate region interposed therebetween;
the dilator periphery further being symmetric on opposite sides of at least a lateral centerline such that the dilator periphery on opposite sides thereof are a mirror image; and
the lateral centerline and a longitudinal centerline dividing the dilator into four quadrants arranged in a 2×2 array, each quadrant having an associated diagonal quadrant disposed diagonally across an intersection point between the lateral centerline and the longitudinal centerline, long edges of each quadrant extending from near the lateral centerline to at least near an end edge of the dilator, the long edges of diagonal quadrants being translationally identical, and wherein
a combined length of the opposite wider dilator end regions is not greater than a length of the intermediate region, and further wherein the plurality of nasal dilators are laterally nested along at least portions of long edges thereof, such that
upper left and lower right quadrants of each dilator are nested along a common line such that the upper left and the lower right quadrants of the laterally nested dilators are adjacent each other, or
lower left and upper right quadrants of each dilator are nested along a common line such that the lower left and the upper right quadrants of the laterally nested dilators are immediately adjacent each other.

2. The dilator of claim 1 wherein the dilator periphery is symmetric on opposite sides of the lateral and longitudinal centerlines, the dilator periphery on opposite sides of either centerline being a mirror image.

3. The nasal dilator of claim 1, wherein the resilient layer comprises at least one resilient member extending fully between opposite end edges of the dilator.

4. The nasal dilator of claim 1 wherein the resilient layer comprises from two to three discrete, substantially rectangular, spaced apart, laterally adjacent, parallel resilient members, at least one resilient member extending fully between opposite end edges of the dilator.

5. The nasal dilator of claim 1 wherein the resilient layer comprises from four to six discrete, substantially rectangular, spaced apart, laterally adjacent, parallel resilient members, at least one resilient member extending fully between opposite end edges of the dilator.

6. The nasal dilator of claim 1 wherein the resilient layer comprises at least one resilient member having a first length, a first width, and a first thickness; and at least one additional resilient member has a thickness exceeding said first thickness, a width at least equal to said first width, and a length at least equal to said first length.

7. The nasal dilator of claim 1 wherein the engagement element comprises a thin, supple plastic film, the resilient layer secured to a flat surface side thereof.

8. The nasal dilator of claim 1, further comprising a protective release liner having a periphery extending outward from at least a portion of the dilator periphery, the release liner periphery including a lip thereat for grasping by a user preliminary to using the dilator.

9. The nasal dilator of claim 1 wherein the intermediate region has opposing long edges extending substantially parallel to the longitudinal centerline of the dilator; and
a substantial portion of a long edge of each end region is substantially parallel to the dilator longitudinal centerline, said long edge portion extending from at least near the intermediate region to at least near the dilator end edge.

10. The nasal dilator of claim 1 wherein the engagement element comprises a base layer secured to at least a portion of one flat surface side of the resilient layer, and a cover layer secured to at least a portion of an opposite flat surface side of the resilient layer.

11. The nasal dilator of claim 10 wherein the base layer has a peripheral surface area equal to or greater than a peripheral surface area of the resilient layer, the base layer peripheral area substantially contained within, and being lesser than, a periphery of the cover layer.

12. A plurality of nasal dilators comprising:
an engagement element and a resilient layer laminated together; the engagement element at least substantially defining a dilator periphery, the dilator periphery defining opposite dilator end regions, the end regions being wider than an intermediate region interposed therebetween;
the dilator periphery further being symmetric on opposite sides of at least a lateral centerline such that the dilator periphery on opposite sides thereof are a mirror image; and
the lateral centerline and a longitudinal centerline dividing the dilator into four quadrants arranged in a 2×2 array, each quadrant having an associated diagonal quadrant disposed diagonally across an intersection point between the lateral centerline and the longitudinal centerline, long edges of each quadrant extending from near the lateral centerline to at least near an end edge of the dilator, the long edges of diagonal quadrants being translationally identical, and wherein
the dilator periphery is configured so that a first end region of a first dilator and a second end region of a second dilator are nested along a common long edge with a third dilator laterally adjacent thereto;
wherein the first and second dilator end regions conform to a substantial portion of the long edges of adjacent quadrants between opposite end edges of the third dilator, the lateral centerlines of the first and second dilators being positioned near the opposite end edges, respectively, of the third dilator; and
one end edge of the first and second dilators, respectively, thus positioned near the lateral centerline of the third dilator.

13. The nasal dilator of claim 12 wherein first and second rows of successive end to end nasal dilators are nested laterally adjacent each other such that the long edges of upper quadrants of the dilators in the first row are nested along the long edges of the upper quadrants of the dilators in the second row.

14. The nasal dilator of claim 12 wherein a portion of the long edge of each quadrant extends in a straight line.

15. The nasal dilator of claim 14 wherein the straight line starts from near the lateral centerline of the dilator and extends obliquely away from the longitudinal centerline.

16. The nasal dilator of claim 12 wherein the intermediate region has opposing long edges extending substantially parallel to the longitudinal centerline of the dilator; and
   a substantial portion of a long edge of each end region diverges obliquely from the dilator longitudinal centerline, said long edge portion extending from the intermediate region to at least near the dilator end edge.

17. The nasal dilator of claim 12 wherein the intermediate region and the end region share an oblique long edge, said oblique long edge extending in an uninterrupted straight line from near the lateral centerline of the dilator to near the end edge of the dilator.

18. Two complementary elongated laminate strands and two nasal dilators, comprising:
   at least one continuous resilient layer strand extending a length of each elongated laminate strand; and
   at least one continuous flexible material layer extending the length of each elongated laminate strand, said continuous resilient layer strand and said continuous flexible material layer laminated together into each respective elongated laminate strand, wherein:
   each elongated laminate strand varies periodically in width across the elongated laminate strand, along the length of the elongated laminate strand, such variations forming wider and narrower portions of the elongated laminate strand between long edges of the elongated laminate strand; and
   a first long edge of a first of the two elongated laminate strands exactly complements a second long edge of a second of the two elongated laminate strands if the strands are placed adjacent each other in a first longitudinal relation, and
   the first long edge of the first of the two elongated laminate strands exactly matches a different long edge of the second elongated laminate strand if the strands are placed adjacent in a second longitudinal relation displaced from the first longitudinal relation by one-half of a period of the variation in width along the length of the two elongated laminate strands, and further comprising:
   two laminated nasal dilators formed by severing an end of both of the two elongated laminate strands from one long edge thereof, across the laminate to another long edge thereof, wherein
   a length of the laminated two nasal dilators is no longer than the period of the variation in width.

\* \* \* \* \*